US012730377B2

(12) United States Patent
Kori et al.

(10) Patent No.: US 12,730,377 B2
(45) Date of Patent: Sep. 8, 2026

(54) COMPOSITION FOR FORMING ORGANIC FILM, PATTERNING PROCESS, AND COMPOUND AND POLYMER FOR FORMING ORGANIC FILM

(71) Applicant: SHIN-ETSU CHEMICAL CO., LTD., Tokyo (JP)

(72) Inventors: Daisuke Kori, Joetsu (JP); Naoki Kobayashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 812 days.

(21) Appl. No.: 17/987,463

(22) Filed: Nov. 15, 2022

(65) Prior Publication Data

US 2023/0161251 A1 May 25, 2023

(30) Foreign Application Priority Data

Nov. 17, 2021 (JP) ................................ 2021-187102

(51) Int. Cl.
*G03F 7/039* (2006.01)
*C07D 209/34* (2006.01)
(Continued)

(52) U.S. Cl.
CPC .......... *G03F 7/039* (2013.01); *C07D 209/34* (2013.01); *C07D 491/107* (2013.01);
(Continued)

(58) Field of Classification Search
None
See application file for complete search history.

(56) References Cited

U.S. PATENT DOCUMENTS

2002/0106909 A1 8/2002 Kato et al.
2005/0255712 A1 11/2005 Kato et al.
(Continued)

FOREIGN PATENT DOCUMENTS

JP H07301916 A * 11/1995
JP 2002-334869 A 11/2002
(Continued)

OTHER PUBLICATIONS

Hernandez et al (Novel, Metal-Free Superacid-Catalyzed "Click" Reactions of Isatins with Linear, Nonactivated, Multiring Aromatic Hydrocarbons, Macromolecules 2010, 43, 6969-6979) (Year: 2010).*
(Continued)

*Primary Examiner* — Sally A Merkling
*Assistant Examiner* — Andrew Preston Traywick
(74) *Attorney, Agent, or Firm* — Oliff PLC

(57) ABSTRACT

An organic film forming composition, containing: a material shown by formula (I) and/or (II); and an organic solvent, where $R_1$ and $R_4$ each represent a hydrogen atom, an allyl or propargyl group, $R_2$ and $R_5$ each represent a substituent, $R_3$ and $R_6$ represents a hydrogen atom, an alkyl group having 1 to 4 carbon atoms, an alkynyl group having 2 to 4 carbon atoms, or an alkenyl group having 2 to 4 carbon atoms. "m" and "i" represent 0 or 1, "k" and "q" represent an integer of 0 to 2, "n" represent 1 or 2, "h", and "j" represent an integer of 0 to 2 and satisfy the relationship $1 \leq h+j \leq 4$, and "l" and "r" represent 0 or 1. W represents a single bond or divalent group shown by formulae (3). Each V independently represents a hydrogen atom or linking moiety.
(Continued)

(I)

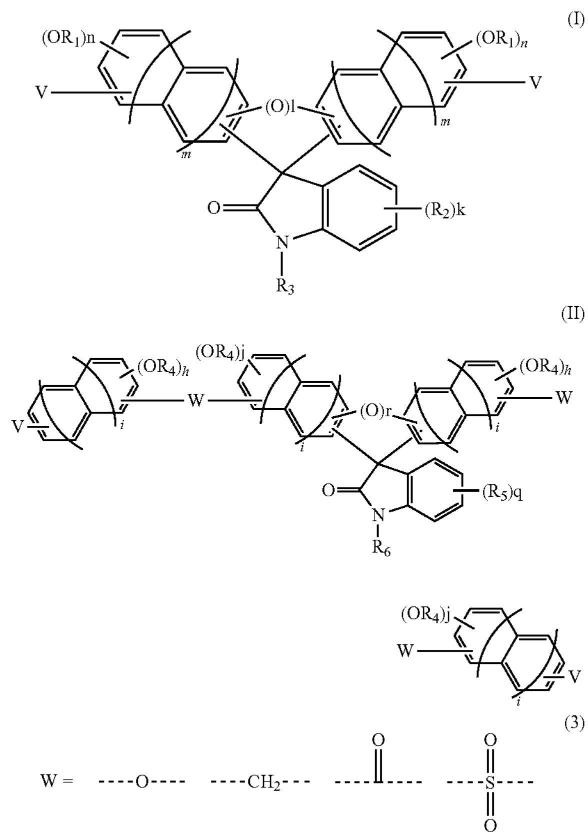

(II)

(3)

21 Claims, 4 Drawing Sheets

(51) Int. Cl.

| | |
|---|---|
| ***C07D 491/107*** | (2006.01) |
| ***C08G 61/12*** | (2006.01) |
| ***G03F 7/075*** | (2006.01) |
| ***G03F 7/09*** | (2006.01) |
| ***H10P 50/00*** | (2026.01) |
| ***H10P 76/20*** | (2026.01) |

(52) U.S. Cl.

CPC ......... *C08G 61/124* (2013.01); *G03F 7/0757* (2013.01); *G03F 7/094* (2013.01); *H10P 50/692* (2026.01); *H10P 76/202* (2026.01); *C08G 2261/11* (2013.01); *C08G 2261/1422* (2013.01); *C08G 2261/1424* (2013.01); *C08G 2261/148* (2013.01); *C08G 2261/149* (2013.01); *C08G 2261/18* (2013.01); *C08G 2261/228* (2013.01); *C08G 2261/312* (2013.01)

(56) References Cited

U.S. PATENT DOCUMENTS

| | | | | |
|---|---|---|---|---|
| 2006/0019195 | A1 | 1/2006 | Hatakeyama et al. | |
| 2006/0204891 | A1 | 9/2006 | Hatakeyama | |
| 2009/0274978 | A1 | 11/2009 | Ohashi et al. | |
| 2010/0099044 | A1 | 4/2010 | Hatakeyama et al. | |
| 2011/0311920 | A1* | 12/2011 | Kinsho | C07C 43/275 430/323 |
| 2013/0302990 | A1 | 11/2013 | Watanabe et al. | |
| 2016/0090449 | A1* | 3/2016 | Nam | C08G 73/0672 524/317 |
| 2017/0184968 | A1* | 6/2017 | Kori | G03F 7/094 |
| 2019/0048129 | A1* | 2/2019 | Nakasugi | C08G 61/02 |
| 2020/0308398 | A1* | 10/2020 | Van Der Mee | G02B 1/041 |
| 2021/0116814 | A1 | 4/2021 | Tokunaga et al. | |
| 2021/0198472 | A1 | 7/2021 | Kori et al. | |
| 2023/0333469 | A1 | 10/2023 | Sato et al. | |

FOREIGN PATENT DOCUMENTS

| | | | |
|---|---|---|---|
| JP | 2004-205685 | A | 7/2004 |
| JP | 2005-128509 | A | 5/2005 |
| JP | 2005-250434 | A | 9/2005 |
| JP | 2006-227391 | A | 8/2006 |
| JP | 2006-285095 | A | 10/2006 |
| JP | 2006-293298 | A | 10/2006 |
| JP | 2007-199653 | A | 8/2007 |
| JP | 2008-158002 | A | 7/2008 |
| JP | 2009-269953 | A | 11/2009 |
| JP | 2010-122656 | A | 6/2010 |
| JP | 2012-247762 | A | 12/2012 |
| JP | 2013-253227 | A | 12/2013 |
| JP | 2016-218140 | A | 12/2016 |
| JP | 2019-506482 | A | 3/2019 |
| KR | 10-2021-0083180 | A | 7/2021 |
| WO | 2004/066377 | A1 | 8/2004 |
| WO | 2019/225615 | A1 | 11/2019 |
| WO | 2022/009948 | A1 | 1/2022 |

OTHER PUBLICATIONS

Translated Description of Kawada (Year: 1995).*

Hernadnez et al (Macromolecules 2010, 43, pp. 6969-6979) (Year: 2010).*

Translation of Kawada et al (Year: 1995).*

Mar. 13, 2025 Office Action issued in European Patent Application No. 22207812.3.

Hernandez, M. Carmen G. et al., "Novel, Metal-Free,Superacid-Catalyzed 'Click' Reactions of lsatins with Linear, Nonactivated, Multiring Aromatic Hydrocarbons," MACROMOLECULES, vol. 43, No. 17, Sep. 14, 2010, pp. 968-6979.

Apr. 24, 2023 extended Search Report issued in European Patent Application No. 22207812.3.

Feb. 6, 2024 Office Action issued in Korean Patent Application No. 10-2022-0152257.

Sep. 3, 2024 Office Action issued in Japanese Patent Application No. 2021-187102.

Nov. 15, 2024 European Office Action issued in European Patent Application No. 22207812.3.

* cited by examiner

[FIG. 1]
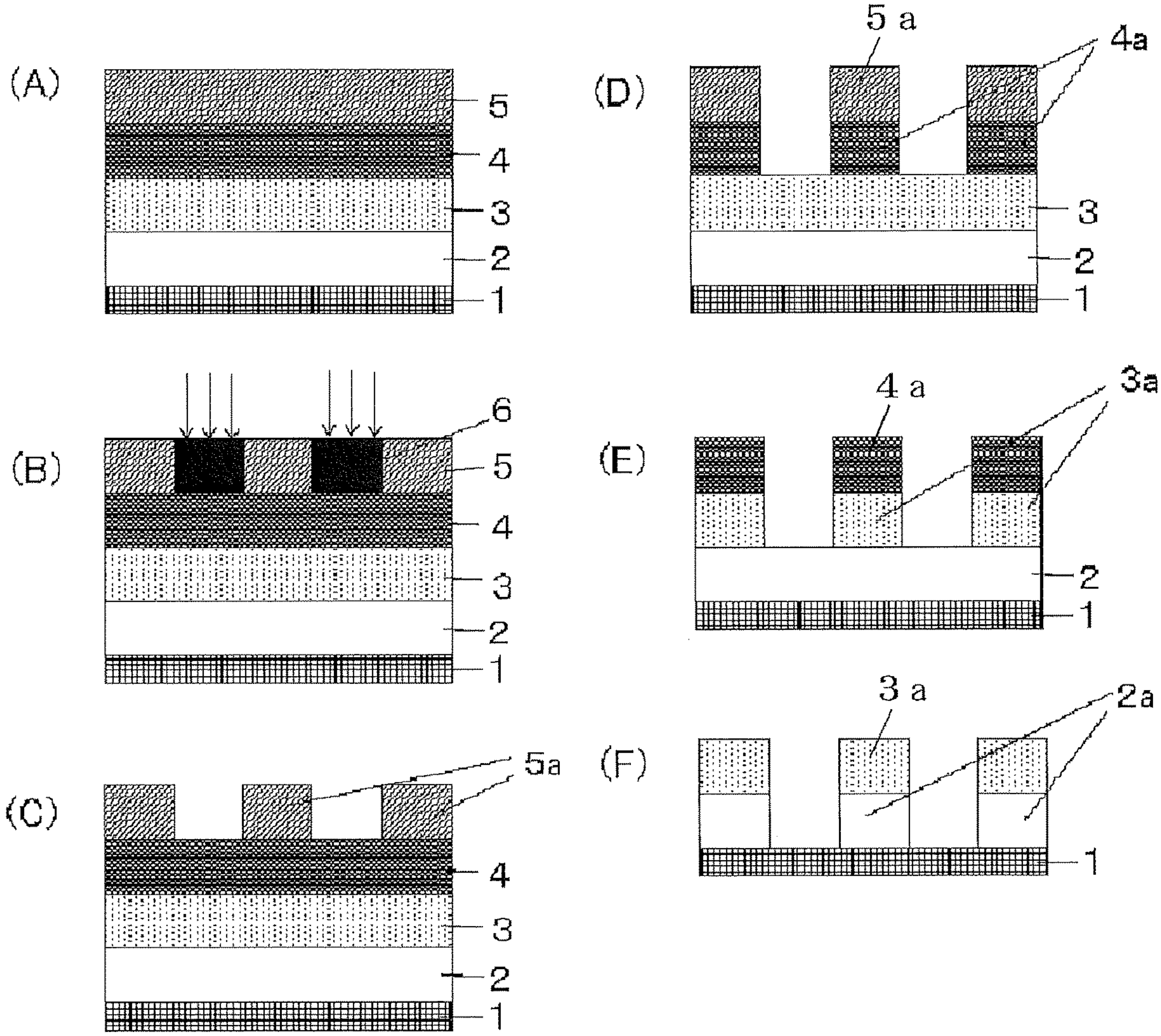

[FIG. 2]
(G)
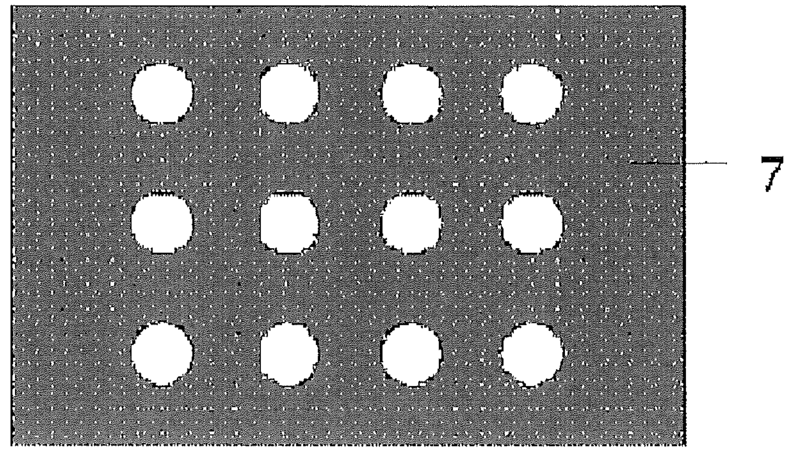
(H)
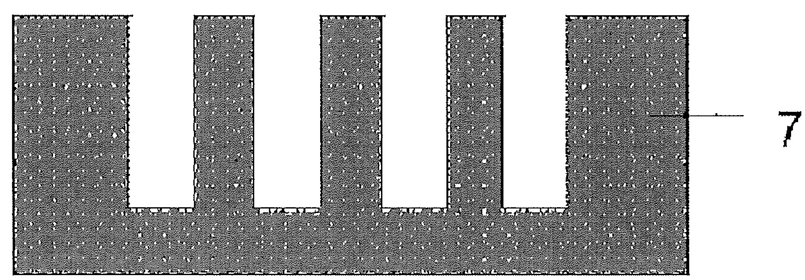
(I)
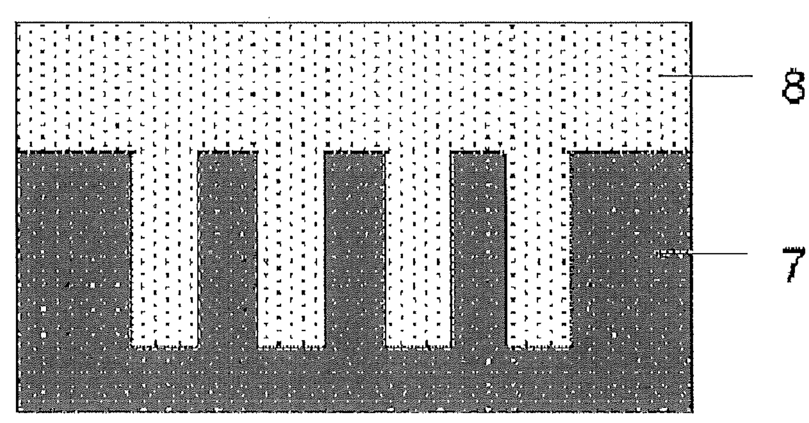

[FIG. 3]
(J)
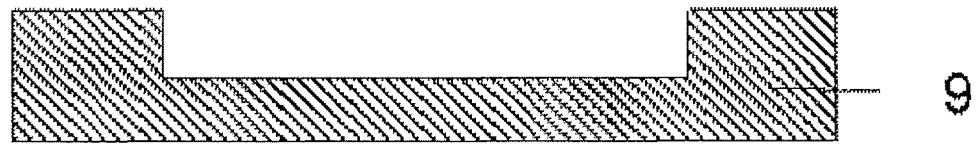
(K)
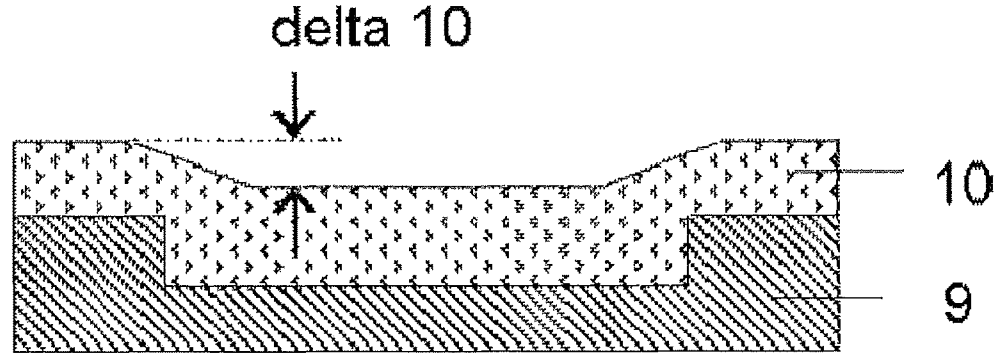

[FIG. 4]
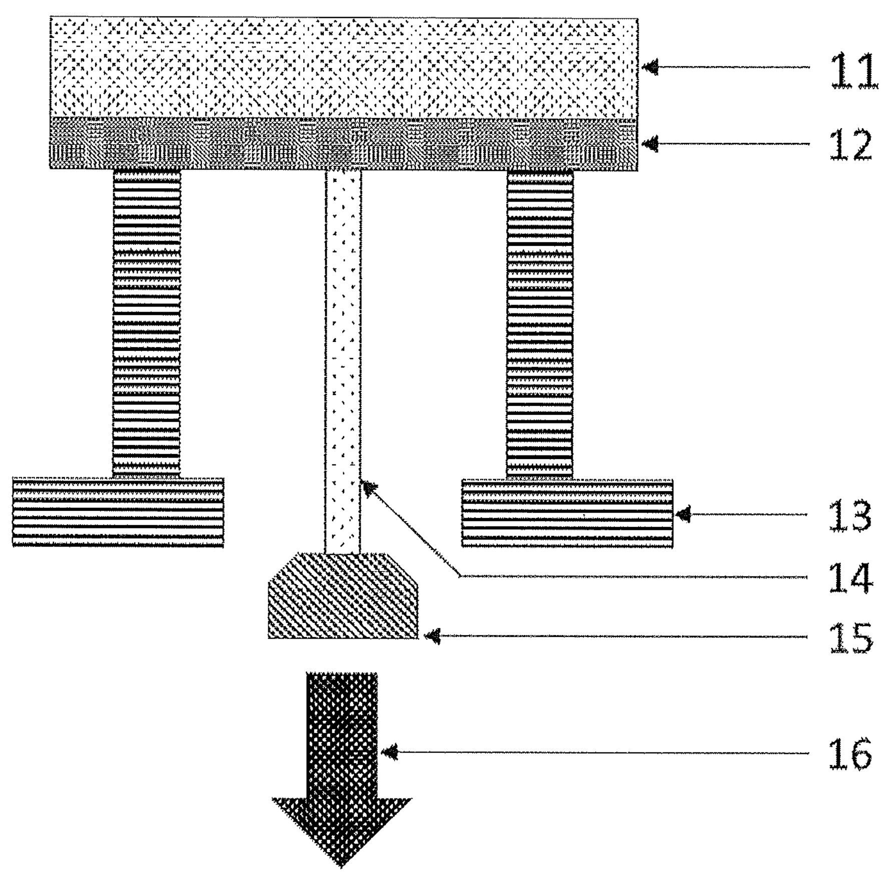

COMPOSITION FOR FORMING ORGANIC FILM, PATTERNING PROCESS, AND COMPOUND AND POLYMER FOR FORMING ORGANIC FILM

TECHNICAL FIELD

The present invention relates to: a composition for forming an organic film used in fine patterning by a multilayer resist method in a semiconductor device manufacturing process; a patterning process using the composition; and a compound and polymer contained in a composition for forming an organic film.

BACKGROUND ART

As LSI advances toward high integration and high processing speed, miniaturization of pattern size is progressing rapidly. Along with the miniaturization, lithography technology has achieved a fine patterning by shortening the wavelength of a light source and selecting an appropriate resist composition accordingly. The composition mainly used is a positive photoresist composition for monolayer. The monolayer positive photoresist composition not only allows a resist resin to have a skeleton having etching resistance against dry etching with chlorine- or fluorine-based gas plasma, but also provides a switching mechanism that makes an exposed part soluble, thereby dissolving the exposed part to form a pattern and processing a body to be processed (substrate to be processed) by dry etching while using the remaining resist pattern as an etching mask.

However, there arises a problem that when the pattern becomes finer, that is, the pattern width is reduced without changing the thickness of the photoresist film to be used, resolution performance of the photoresist film is lowered. In addition, pattern development of the photoresist film with a developer excessively increases a so-called aspect ratio of the pattern, resulting in pattern collapse. Therefore, the photoresist film has been thinned along with the miniaturization of the pattern.

On the other hand, a substrate to be processed has been generally processed by dry etching while using a pattern-formed photoresist film as an etching mask. In practice, however, there is no dry etching method capable of providing an absolute etching selectivity between the photoresist film and the substrate to be processed. There has been a problem that the resist film is thus damaged and collapses during processing of the substrate, and the resist pattern cannot be precisely transferred to the substrate to be processed. Accordingly, higher dry etching resistance has been required in a resist composition along with the miniaturization of the pattern. However, on the other hand, resins used for photoresist compositions have been required to have low absorbance at the wavelength to be used for the exposure in order to achieve a higher resolution. Accordingly, as the exposure light shifts from i-beam to KrF and to ArF to have a shorter wavelength, the resin also shifts to novolak resins, polyhydroxystyrene, and resins having an aliphatic polycyclic skeleton. This shift actually accelerates an etching rate under the dry etching conditions during substrate processing, and recent photoresist compositions having high resolution tend to have low etching resistance.

As a result, a substrate to be processed has to be dry-etched with a thinner photoresist film having lower etching resistance. It is important to provide a material for this process and the process itself.

A multilayer resist method is one solution for these problems. This method is as follows: a middle layer film having a different etching selectivity from a photoresist film (i.e., a resist upper layer film) is placed between the resist upper layer film and a substrate to be processed; a pattern is formed in the resist upper layer film; then, the pattern is transferred to the middle layer film by dry etching while using the resist upper layer film pattern as a dry etching mask; and the pattern is further transferred to the substrate to be processed by dry etching while using the middle layer film as a dry etching mask.

One of the multilayer resist methods is a 3-layer resist method, which can be performed with a typical resist composition used in the monolayer resist method. For example, this 3-layer resist method includes the following steps: an organic film containing a novolak resin or the like is formed on a substrate to be processed; a silicon-containing film is formed thereon as a resist middle layer film; and a usual organic photoresist film is formed thereon as a resist upper layer film. Since the organic resist upper layer film exhibits a favorable etching selectivity ratio relative to the silicon-containing resist middle layer film when dry etching is performed with fluorine-based gas plasma, the resist upper layer film pattern can be transferred to the silicon-containing resist middle layer film by dry etching with fluorine-based gas plasma. According to this process, even when using a resist composition which is difficult to form a pattern in so that the pattern has a sufficient film thickness for directly processing the substrate to be processed or a resist composition which does not have sufficient dry etching resistance for processing the substrate, a pattern can be transferred to a silicon-containing film (resist middle layer film). In addition, by subsequently transferring the pattern by dry etching using an oxygen- or hydrogen-based gas plasma, it is possible to obtain a pattern of an organic film (resist underlayer film) containing a novolak resin or the like having a sufficient dry etching resistance for processing the substrate. As such an organic film, many are already known, such as those disclosed in Patent Document 1, for example.

Meanwhile, in recent years, consideration of the production of semiconductor devices having a new structure such as a multigate structure has become active. In response, demands are rising for an organic film having better planarizing property and filling property than before. For example, when an underlying substrate to be processed has a fine pattern structure such as a hole, a trench, or a fin, it is necessary to have filling (gap-filling) property for filling in the pattern with a film without any voids by using an organic film. In addition, when the underlying substrate to be processed has a step(s), or when a pattern-dense region and a pattern-free region exist on the same wafer, it is necessary to planarize the film surface with the organic film. By planarizing the surface of the organic film, fluctuation in the film thickness of a resist middle layer film or a resist upper layer film formed thereon is controlled, whereby a focus margin in lithography or a margin in the subsequent processing step of the substrate to be processed can be suppressed from decreasing.

Moreover, the organic film material excellent in filling and planarizing properties is not limited to the underlayer film for a multilayer resist, and is also widely usable as a planarizing material for manufacturing a semiconductor device, e.g., for planarizing a substrate prior to patterning by nanoimprinting. Furthermore, for global planarizing in the semiconductor device manufacturing process, a CMP process is now generally used. However, the CMP process is costly, so that this material is also expected to be used for the global planarizing method, instead of CMP.

For forming a flat film for planarizing an uneven semiconductor substrate, an organic film material containing a polymer obtained by a reaction between an aromatic compound and a compound having a carbon-oxygen double bond such as a carbonyl group is proposed (Patent Document 2). However, planarizing performance etc. of the material in wide trench portions in the substrate are insufficient to meet the demands in cutting-edge devices, and an organic film material excellent in flatness on a wider range of substrate structures has come to be required.

In addition, the structures of substrates to be processed are becoming complex as described above. Furthermore, for the surface of a substrate to be processed, the following materials are also being examined: novel materials having high electron mobility using strained silicon, gallium arsenic, and so forth; ultrathin polysilicon controlled in units of angstrom; and the like. Thus, films are expected to be formed on surfaces of substrates to be processed having various shapes and qualities. Therefore, in order to ensure a process margin, not only excellent filling and planarizing properties, but also being able to form a film without dependence on the quality or shape of the substrate to be processed is an important feature.

CITATION LIST

Patent Literature

Patent Document 1: JP 2004-205685 A
Patent Document 2: WO 2019/225615 A1

SUMMARY OF INVENTION

Technical Problem

The present invention has been made in view of the above circumstances. An object of the present invention is to provide: a compound and a polymer which allow the formation of an organic film having not only excellent heat resistance and properties of filling and planarizing a pattern formed on a substrate, but also favorable film-formability and adhesiveness to a substrate; and a composition for forming an organic film containing the compound and/or polymer. Another object of the present invention is to provide a patterning process using the composition.

Solution to Problem

To achieve the object, the present invention provides a composition for forming an organic film, comprising: a material for forming an organic film shown by the following general formula (I) and/or general formula (II); and an organic solvent, (I)

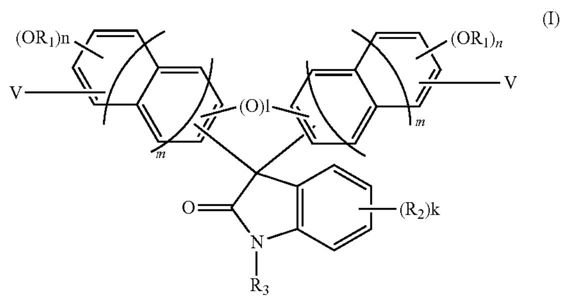

wherein $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents a hydrogen atom, an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, "k" represents an integer of 0 to 2, and each V independently represents a hydrogen atom or a linking moiety, (II)

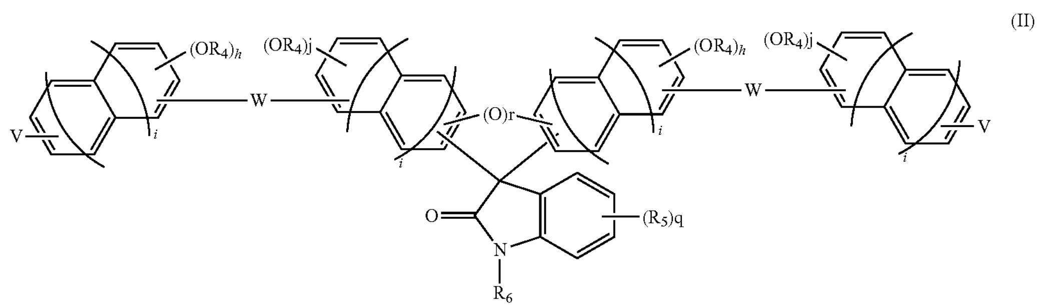

wherein $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents a hydrogen atom, an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship $1 \leq h+j \leq 4$, "r" represents 0 or 1, aromatic rings forming a cyclic ether structure with one another when r=1, W represents a single bond or any divalent group shown by the following formulae (3), and each V independently represents a hydrogen atom or a linking moiety, (3)

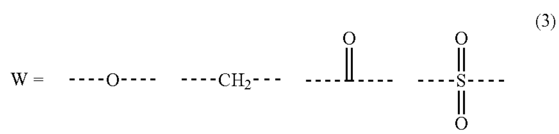

wherein a broken line represents an attachment point.

Such a composition for forming an organic film is capable of forming an organic film that is not only excellent in heat resistance and filling and planarizing properties of a pattern formed in a substrate, but also has favorable film-formability and adhesiveness to a substrate.

In this case, the material for forming an organic film can be a compound shown by the following general formula (1) and/or (2), (1)

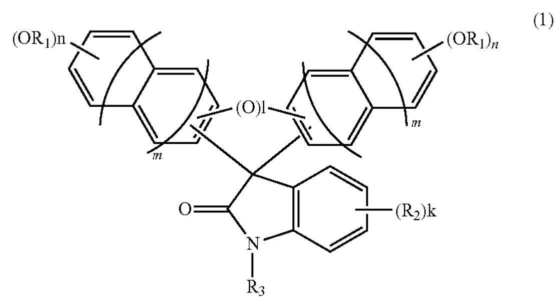

wherein $R_1$, $R_2$, $R_3$, "m", "n", "l", and "k" are as defined above, (2)

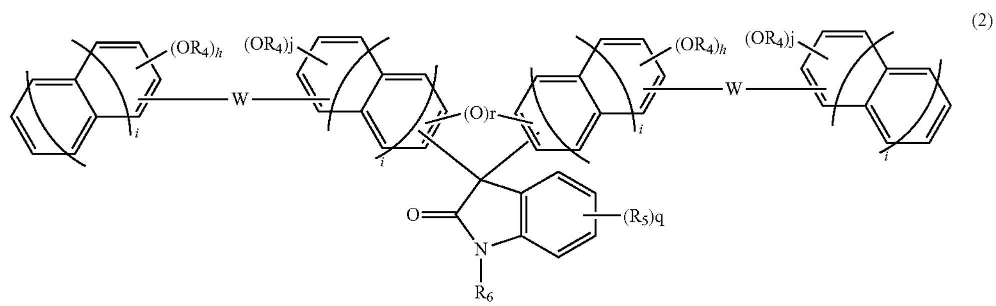

wherein $R_4$, $R_5$, $R_6$, "i", "q", "h", "j", "r", and W are as defined above.

The inventive compound shown by the general formula (1) and/or (2) is excellent in heat resistance, and therefore, can form an organic film material as a simple compound. In addition, since the compound has better thermal flowability than polymers, when the compound is used for an organic film, the organic film is also excellent in filling and planarizing properties to a patterned substrate. Furthermore, since the compound has a cyclic amide structure in the molecule, adhesiveness and film-formability to a substrate and so forth can also be improved without losing heat resistance.

In addition, the compound shown by the general formula (1) and/or (2) preferably satisfies $1.00 \leq Mw/Mn \leq 1.10$, where Mw is a weight-average molecular weight and Mn is a number-average molecular weight measured by gel permeation chromatography in terms of polystyrene.

By controlling the Mw/Mn of the compound for forming an organic film within such a range, an organic film excellent in filling property and flatness can be formed.

Furthermore, in the present invention, the material for forming an organic film can be a polymer having a repeating unit shown by the following general formula (4) and/or (5), (4)

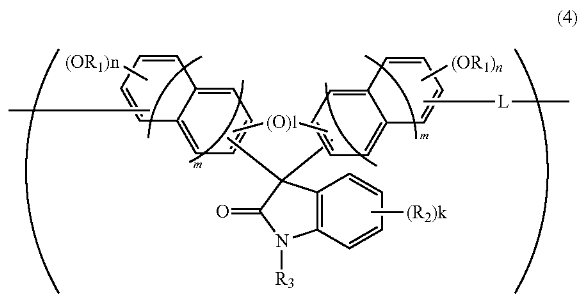

wherein $R_1$, $R_2$, $R_3$, "m", "n", "l", and "k" are as defined above, and L represents a divalent organic group having 1 to 40 carbon atoms, (5)

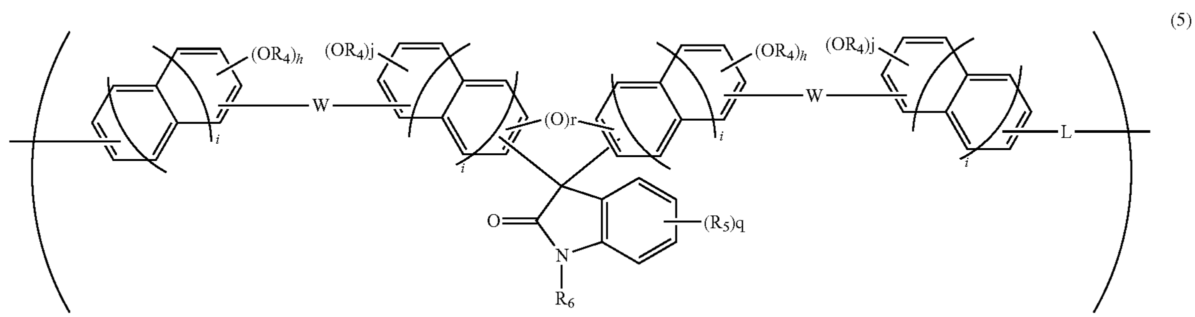

wherein $R_4$, $R_5$, $R_6$, W, L, "h", "i", "j", "q", and "r" are as defined above.

When a polymer having such a repeating unit is used, it is possible to achieve a composition for forming an organic film that has no degradation of etching resistance, can form a dense organic film by increasing curability, and furthermore, is excellent in film formability with no dependence on the quality or shape of the substrate.

In this case, the L is preferably a divalent organic group shown by the following general formula (6), (6)

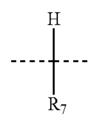

wherein $R_7$ represents a hydrogen atom or an aromatic ring-containing organic group having 1 to 20 carbon atoms, and a broken line represents an attachment point.

Properties such as curability and etching resistance can be improved by including such a linking group L in the repeating unit.

Furthermore, the polymer preferably has a weight-average molecular weight of 1000 to 5000 measured by gel permeation chromatography in terms of polystyrene.

When the composition for forming an organic film contains a polymer having a weight-average molecular weight within such a range, outgas during baking can be suppressed without losing solubility to an organic solvent.

Furthermore, in the present invention, the material for forming an organic film can contain one or more compounds selected from a compound shown by the following general formula (1) and/or (2) and one or more polymers selected from a polymer having a repeating unit shown by the following general formula (4) and/or (5), (1)
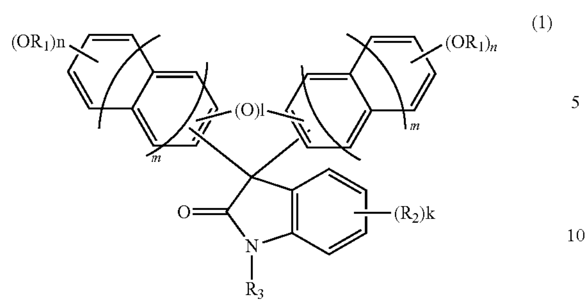
wherein $R_1$, $R_2$, $R_3$, "m", "n", "l", and "k" are as defined above,
(2)
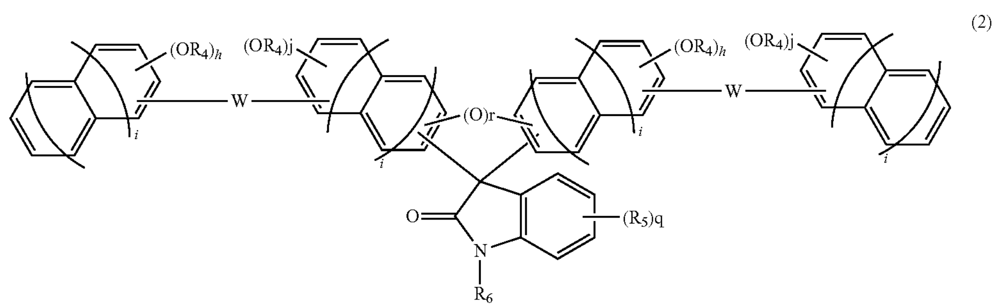
wherein $R_4$, $R_5$, $R_6$, "i", "q", "h", "j", "r", and W are as defined above,
(4)
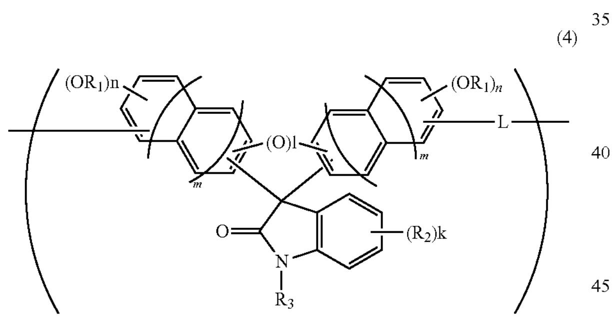
wherein $R_1$, $R_2$, $R_3$, "m", "n", "l", and "k" are as defined above, and L represents a divalent organic group having 1 to 40 carbon atoms,
(5)
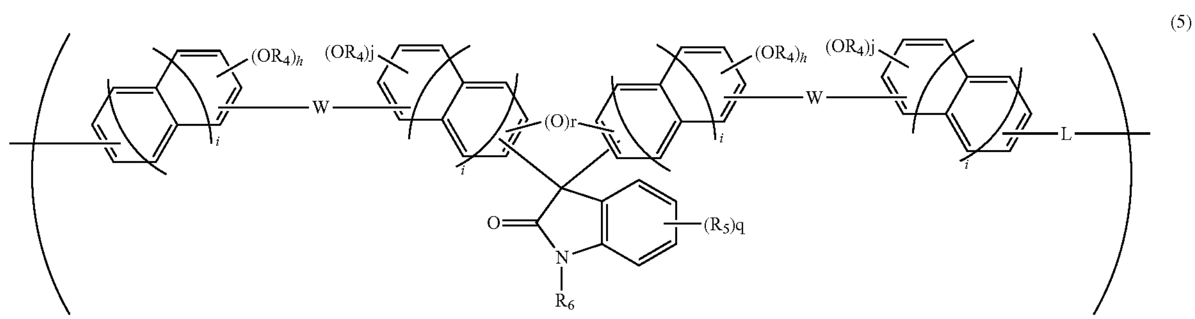

wherein $R_4$, $R_5$, $R_6$, W, L, "h", "i", "j", "q", and "r" are as defined above.

Using such a mixture, it is possible to adjust, within an appropriate range, various physical properties required when using the mixture for forming an organic film, for example, filling and planarizing properties and outgas caused by sublimation products.

In addition, the organic solvent is preferably a mixture of one or more kinds of organic solvent having a boiling point of lower than 180° C. and one or more kinds of organic solvent having a boiling point of 180° C. or higher.

When the organic solvent is the above mixture, the organic film is provided with thermal flowability by adding the high-boiling-point solvent to the compound and/or polymer, so that the composition for forming an organic film is provided with both high filling and planarizing properties.

The composition for forming an organic film preferably further comprises at least one of a surfactant and a plasticizer.

The composition for forming an organic film containing such additives has more excellent coating property and filling and planarizing properties.

In addition, the present invention provides a patterning process comprising:

forming an organic film by using the above-described composition for forming an organic film on a body to be processed;

forming a silicon-containing resist middle layer film by using a silicon-containing resist middle layer film material on the organic film;

forming a resist upper layer film by using a photoresist composition on the silicon-containing resist middle layer film;

forming a circuit pattern in the resist upper layer film;

transferring the pattern to the silicon-containing resist middle layer film by etching while using the resist upper layer film having the formed pattern as a mask;

transferring the pattern to the organic film by etching while using the silicon-containing resist middle layer film having the transferred pattern as a mask; and further forming the pattern in the body to be processed by etching while using the organic film having the transferred pattern as a mask.

A fine pattern can be formed in the body to be processed (substrate to be processed) with high precision by the patterning process according to the 3-layer resist process.

In addition, the present invention provides a patterning process comprising:

forming an organic film by using the above-described composition for forming an organic film on a body to be processed;

forming a silicon-containing resist middle layer film by using a silicon-containing resist middle layer film material on the organic film;

forming an organic antireflective coating on the silicon-containing resist middle layer film;

forming a resist upper layer film by using a photoresist composition on the organic antireflective coating, so that a 4-layered film structure is constructed;

forming a circuit pattern in the resist upper layer film;

transferring the pattern to the organic antireflective coating and the silicon-containing resist middle layer film by etching while using the resist upper layer film having the formed pattern as a mask;

transferring the pattern to the organic film by etching while using the silicon-containing resist middle layer film having the transferred pattern as a mask; and further forming the pattern in the body to be processed by etching the body to be processed while using the organic film having the transferred pattern as a mask.

A fine pattern can be formed in the body to be processed with even higher precision by the patterning process according to the 4-layer resist process.

In addition, the present invention provides a patterning process comprising:

forming an organic film by using the above-described composition for forming an organic film on a body to be processed;

forming an inorganic hard mask selected from a silicon oxide film, a silicon nitride film, and a silicon oxynitride film on the organic film;

forming a resist upper layer film by using a photoresist composition on the inorganic hard mask;

forming a circuit pattern in the resist upper layer film;

etching the inorganic hard mask while using the resist upper layer film having the formed pattern as a mask;

etching the organic film while using the inorganic hard mask having the formed pattern as a mask; and further forming the pattern in the body to be processed by etching the body to be processed while using the organic film having the formed pattern as a mask.

A fine pattern can be formed on the body to be processed with high precision by the patterning process according to the 3-layer resist process.

In addition, the present invention provides a patterning process comprising:

forming an organic film by using the above-described composition for forming an organic film on a body to be processed;

forming an inorganic hard mask selected from a silicon oxide film, a silicon nitride film, and a silicon oxynitride film on the organic film;

forming an organic antireflective coating on the inorganic hard mask;

forming a resist upper layer film by using a photoresist composition on the organic antireflective coating, so that a 4-layered film structure is constructed;

forming a circuit pattern in the resist upper layer film;

etching the organic antireflective coating and the inorganic hard mask while using the resist upper layer film having the formed pattern as a mask;

etching the organic film while using the inorganic hard mask having the formed pattern as a mask; and further forming the pattern in the body to be processed by etching the body to be processed while using the organic film having the formed pattern as a mask.

A fine pattern can be formed on the body to be processed with higher precision by the patterning process according to this 4-layer resist process.

In this case, the inorganic hard mask is preferably formed by a CVD method or an ALD method.

When the inorganic hard mask is formed by a CVD method or an ALD method, a fine pattern can be formed in the body to be processed with higher precision.

Furthermore, the pattern in the resist upper layer film is preferably formed by a lithography using light with a wavelength of 10 nm or more to 300 nm or less, a direct drawing with electron beam, nanoimprinting, or a combination thereof.

When the circuit pattern is formed in the resist upper layer film by such methods, a fine pattern can be formed in the body to be processed with higher precision.

Furthermore, exposure and development are preferably performed to form the circuit pattern in the resist upper layer film in the patterning process, and the development is preferably alkali development or development with an organic solvent.

When alkali development or development with an organic solvent is employed as the development method, a fine pattern can be formed in the body to be processed with higher precision.

Furthermore, as the body to be processed, a semiconductor device substrate, a metal film, a metal carbide film, a metal oxide film, a metal nitride film, a metal oxycarbide film, or a metal oxynitride film is preferably used.

In the present invention, those given above can be used, for example, as the body to be processed.

In this case, the metal is preferably silicon, titanium, tungsten, hafnium, zirconium, chromium, germanium, cobalt, copper, silver, gold, aluminum, indium, gallium, arsenic, palladium, iron, tantalum, iridium, manganese, molybdenum, ruthenium, or an alloy thereof.

These metals can be used as the metal. When a pattern is formed using the inventive composition for forming an organic film as described, the pattern of the upper layer photoresist can be transferred to and formed in the body to be processed with higher precision.

The present invention also provides a compound shown by the following general formula (1), (1)

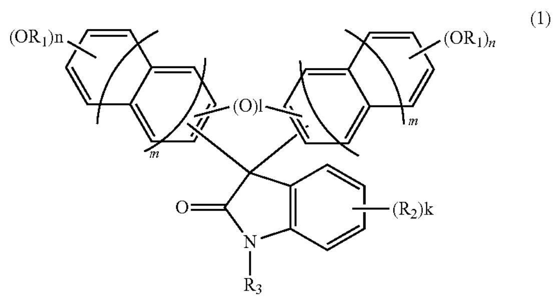

wherein $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents a hydrogen atom, an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, and "k" represents an integer of 0 to 2.

The present invention also provides a compound shown by the following general formula (2), (2)

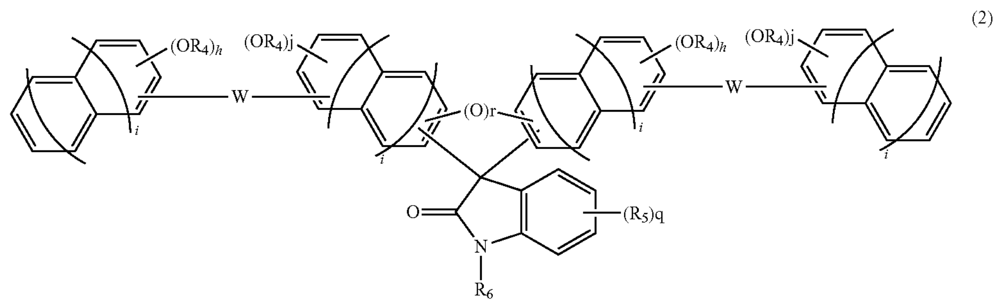

wherein $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents a hydrogen atom, an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship $1 \le h+j \le 4$, "r" represents 0 or 1, aromatic rings forming a cyclic ether structure with one another when r=1, and W represents a single bond or any divalent group shown by the following formulae (3), (3)

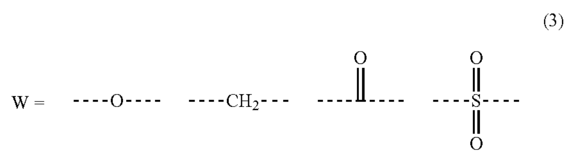

wherein a broken line represents an attachment point.

The compound shown by the general formula (1) or (2) is a compound used in the composition for forming an organic film that makes it possible to form an organic film excellent in heat resistance, filling and planarizing properties, and film-formability.

In addition, the present invention provides a polymer having a repeating unit shown by the following general formula (4), (4)

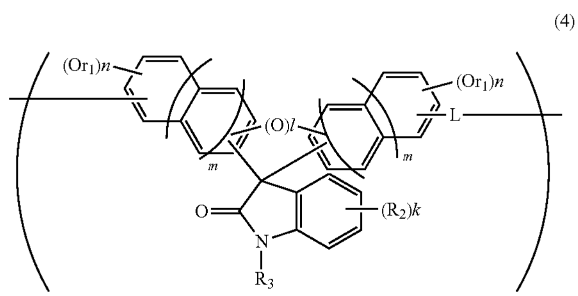

wherein $R_1$, $R_2$, $R_3$, "m", "n", "l", and "k" are as defined above, and L represents a divalent organic group having 1 to 40 carbon atoms.

The present invention also provides a polymer having a repeating unit shown by the following general formula (5), (5)

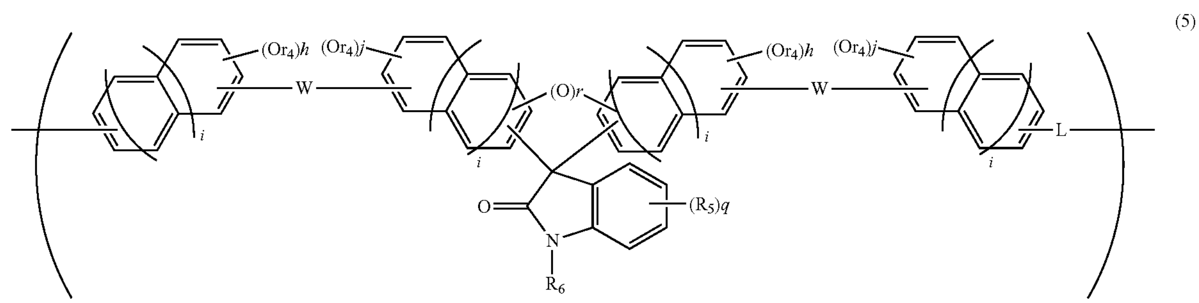

wherein $R_4$, $R_5$, $R_6$, "i", "q", "h", "j", "r", W, and L are as defined above.

The polymers shown by the general formulae (4) and (5) are polymers used in a composition for forming an organic film that makes it possible to form an organic film excellent in curability.

In this case, the L is preferably a divalent organic group shown by the following general formula (6), (6)

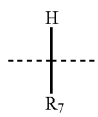

wherein $R_7$ represents a hydrogen atom or an aromatic ring-containing organic group having 1 to 20 carbon atoms, and a broken line represents an attachment point.

By introducing such a linking group L, various physical properties of the polymer such as curability and etching resistance can be improved.

Advantageous Effects of Invention

As described above, the inventive compound or polymer is useful for forming an organic film excellent in heat resistance and excellent in filling and planarizing performances, film-formability, and adhesiveness. In addition, a composition for forming an organic film containing the compound and/or polymer has various properties such as heat resistance and filling and planarizing properties, and is a material useful for forming an organic film that can be formed with no dependence on the substrate to be processed and that is also excellent in adhesiveness. Therefore, the composition is extremely useful as a composition for forming an organic film in a multilayer resist process such as a 2-layer resist process, a 3-layer resist process using a silicon-containing resist middle layer film, or a 4-layer resist process using a silicon-containing resist middle layer film and an organic antireflective coating, or as a planarizing material for manufacturing a semiconductor device, for example. Furthermore, according to the inventive patterning process, a fine pattern can be formed in a body to be processed with high precision in a multilayer resist process.

BRIEF DESCRIPTION OF DRAWINGS

FIG. 1 is an explanatory diagram of an example of an inventive patterning process according to a 3-layer resist process.

FIG. 2 is an explanatory diagram of a method for evaluating the filling property in Examples and Comparative Examples.

FIG. 3 is an explanatory diagram of a method for evaluating the planarizing property in Examples and Comparative Examples.

FIG. 4 is an explanatory diagram showing a method for measuring the adhesiveness in Examples and Comparative Examples.

DESCRIPTION OF EMBODIMENTS

As described above, the following have been desired: a composition for forming an organic film in a fine patterning process by a multilayer resist method in a semiconductor device manufacturing process, where the composition makes it possible to form an organic film excellent in film-formability and flatness even on a body to be processed (substrate to be processed) having portions that are particularly difficult to planarize such as a wide trench structure; a patterning process in which the composition is used; and a compound and polymer suitable for such a composition for forming an organic film.

The present inventors have earnestly studied the above problems and found out that the inventive compound or polymer forming the main skeleton with a specific hetero ring structure is useful for forming an organic film excellent in filling and planarizing properties, and completed the present invention.

That is, the present invention is a composition for forming an organic film, comprising: a material for forming an organic film shown by the following general formula (I) and/or general formula (II); and an organic solvent, (I)

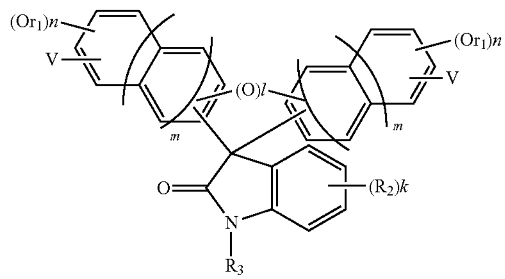

wherein $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents a hydrogen atom, an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, "k" represents an integer of 0 to 2, and each V independently represents a hydrogen atom or a linking moiety, (II)

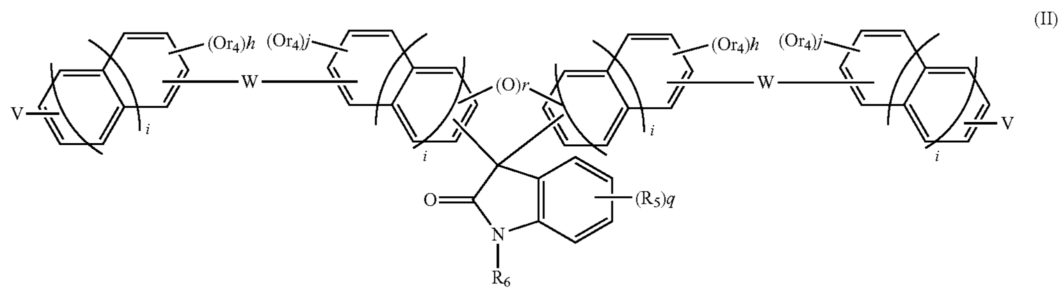

wherein $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents a hydrogen atom, an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship $1 \leq h+j \leq 4$, "r" represents 0 or 1, aromatic rings forming a cyclic ether structure with one another when r=1, W represents a single bond or any divalent group shown by the following formulae (3), and each V independently represents a hydrogen atom or a linking moiety, (3)

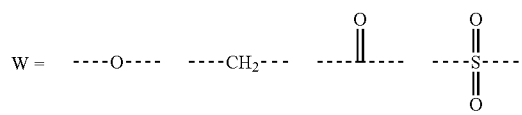

wherein a broken line represents an attachment point.

Hereinafter, the present invention will be described in detail, but the present invention is not limited thereto.

[Composition for Forming Organic Film]

The inventive composition for forming an organic film contains: a material for forming an organic film shown by a specific general formula described below; and an organic solvent.

The composition for forming an organic film can be any composition as long as the material for forming an organic film shown by the general formula and an organic solvent are contained, and may contain additives such as a surfactant or a plasticizer as necessary. In the following, the components contained in the inventive composition will be described.

[Material for Forming Organic Film]

The inventive composition for forming an organic film contains a material for forming an organic film shown by the following general formula (I) and/or (II).

(I)

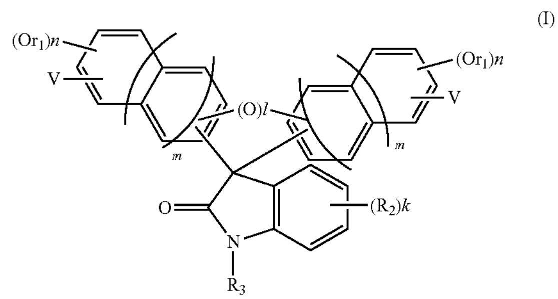

In the general formula (I), $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents a hydrogen atom, an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, "k" represents an integer of 0 to 2, and each V independently represents a hydrogen atom or a linking moiety.

(II)

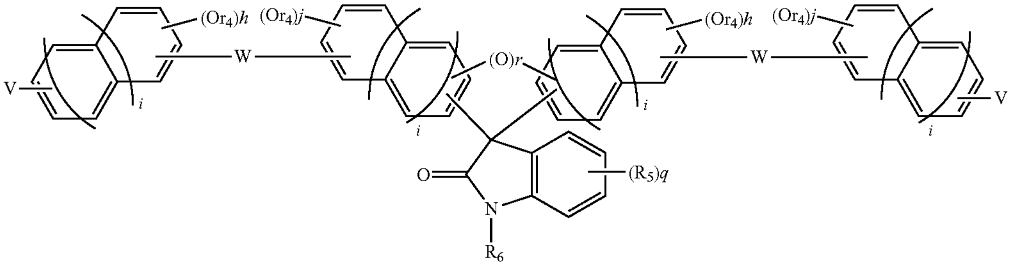

In the general formula (II), $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents a hydrogen atom, an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship $1 \leq h+j \leq 4$, "r" represents 0 or 1, aromatic rings forming a cyclic ether structure with one another when r=1, W represents a single bond or any divalent group shown by the following formulae (3), and each V independently represents a hydrogen atom or a linking moiety.

(3)

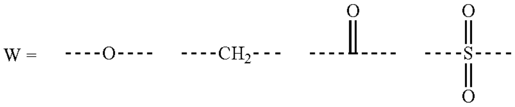

A broken line represents an attachment point.

The $R_1$ in the general formula (I) represents a hydrogen atom, an allyl group, or a propargyl group. In view of thermosetting property, a hydrogen atom or a propargyl group is preferable, and from the viewpoint of providing thermal flowability, a propargyl group is particularly preferable. Furthermore, as $R_1$, hydrogen atoms, allyl groups, and propargyl groups can also be used in combination at any proportion. In this case, when the proportion of hydrogen atoms is a % and the proportion of allyl groups and propargyl group is b %, the constitution ratio of $R_1$ satisfies the relationship a+b=100(%). When it is desired to improve film-formability or the adhesiveness of the film to the substrate, the proportion "a" of hydrogen atoms can be increased, that is, a>b can be satisfied, and when it is desired to improve curability, heat resistance, and flatness, the proportion of allyl groups or propargyl groups can satisfy a<b. These can be adjusted to any proportions in accordance with the required performance.

$R_2$ in the general formula represents a nitro group, a halogen atom, such as a fluorine atom or a chlorine atom, a hydroxy group, an alkyloxy group having 1 to 4 carbon atoms, such as a methoxy group or an ethoxy group, an alkynyloxy group having 2 to 4 carbon atoms, such as a propargyloxy group, an alkenyloxy group having 2 to 4 carbon atoms, such as an allyloxy group, a linear, branched, or cyclic alkyl group having 1 to 6 carbon atoms, such as a methyl group, an isobutyl group, or a cyclohexyl group, a trifluoromethyl group, or a trifluoromethyloxy group.

$R_3$ in the general formula represents a hydrogen atom, an alkyl group having 1 to 4 carbon atoms, an alkynyl group having 2 to 4 carbon atoms, or an alkenyl group having 2 to 4 carbon atoms. Specifically, examples include the following. In particular, an alkynyl group or an alkenyl group is preferable from the viewpoints of easy availability of raw materials and providing thermosetting property, and an allyl group and a propargyl group are more preferable since these are easily synthesized. Furthermore, in $R_3$, hydrogen atoms, alkyl groups, alkynyl groups, and alkenyl groups can also be used in combination at any proportion. In this case, when the proportion of hydrogen atoms is A % and the proportion of allyl groups and propargyl groups is B %, the constitution ratio of $R_3$ satisfies the relationship A+B=100(%). When it is desired to improve film-formability or the adhesiveness of the film to the substrate, the proportion A of hydrogen atoms can be increased, that is, A>B can be satisfied, and when it is desired to improve curability, heat resistance, and flatness, the proportion B of allyl groups or propargyl groups can be increased, that is, A<B can be satisfied. These can be adjusted to any proportions in accordance with the required performance.

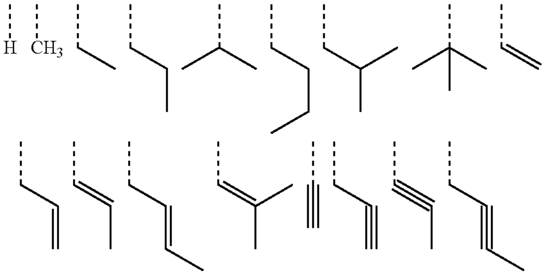

A broken line represents an attachment point.

"m" represents 0 or 1, "n" represents an integer of 1 or 2, and "l" represents 0 or 1. When 1=1, it means that aromatic rings form a cyclic ether structure with one another. Furthermore, "n" and "l" can satisfy the relationship $1 \leq n+l \leq 3$. "k" represents an integer of 0 to 2. "m" is preferably 0, "l" is preferably 0, and "k" is preferably 0.

The W in the general formula (II) represents a single bond or the general formula (3). In particular, W is preferably an ether bond from the viewpoint of providing thermal flowability. In the case of an ether bond, thermal flowability can be provided without losing heat resistance.

The $R_4$ in the general formula (II) represents a hydrogen atom, an allyl group, or a propargyl group. From the viewpoint of thermosetting property, a hydrogen atom and a propargyl group are preferable, and from the viewpoint of providing thermal flowability, a propargyl group is particularly preferable. In the same manner as the $R_1$ in the general formula (I), hydrogen atoms, allyl groups, and propargyl groups can also be used in combination at any proportion in accordance with the required performance in $R_4$.

$R_5$ in the general formula (II) represents a nitro group, a halogen atom, such as a fluorine atom or a chlorine atom, a hydroxy group, an alkyloxy group having 1 to 4 carbon atoms, such as a methoxy group or an ethoxy group, an alkynyloxy group having 2 to 4 carbon atoms, such as a propargyloxy group, an alkenyloxy group having 2 to 4 carbon atoms, such as an allyloxy group, a linear, branched, or cyclic alkyl group having 1 to 6 carbon atoms, such as a methyl group, an isobutyl group, or a cyclohexyl group, a trifluoromethyl group, or a trifluoromethyloxy group.

$R_6$ in the general formula (II) represents a hydrogen atom, an alkyl group having 1 to 4 carbon atoms, an alkynyl group having 2 to 4 carbon atoms, or an alkenyl group having 2 to 4 carbon atoms, and specific examples include the same examples as the $R_3$ of the general formula (I). In view of thermosetting property and easy synthesis, an allyl group and a propargyl group are more preferable. Furthermore, in $R_6$, too, hydrogen atoms, alkyl groups, alkynyl groups, and alkenyl groups can be used in combination at any proportion in accordance with the required performance in the same manner as the $R_3$ in the general formula (I) as described above.

Each V in the general formulae (I) and (II) independently represents a hydrogen atom or a linking moiety. When all Vs are hydrogen atoms (there are no linking moieties), the materials for forming an organic film shown by the general formulae are monomolecular compounds, and correspond to the compounds shown by the general formulae (1) and (2) described below. When V is a linking moiety, the materials for forming an organic film are polymers. The linking moiety is a moiety that links the structures shown by the general formulae with each other, and can be, for example, a single bond, or those given as linking groups L described below. That is, the polymers encompass the polymers having the repeating units shown by the general formulae (4) and (5) described below.

"i" represents 0 or 1, "q" represents an integer of 0 to 2, and "h" and "j" each independently represent an integer of 0 to 2 and satisfy the relationship $1 \leq h+j \leq 4$. "r" represents 0 or 1, and when r=1, it means that aromatic rings form a cyclic ether structure with one another. Furthermore, "h", "j", and "l" can satisfy the relationships $1 \leq h+l \leq 3$ and $1 \leq j+l \leq 3$. "i" is preferably 0, "q" is preferably 0, and "r" is preferably 0.

The material for forming an organic film can be the compound shown by the following general formula (1) or the compound shown by the general formula (2) (hereinafter, these compounds are also referred to as "compounds used in a composition for forming an organic film"), and can also be the polymer having the repeating unit shown by the following general formula (4) or the polymer having the repeating unit shown by the general formula (5) (hereinafter, these polymers are also referred to as "polymers used in a composition for forming an organic film"). In addition, the material for forming an organic film can also contain one or more compounds selected from the compound shown by the general formula (1) and/or (2) and one or more polymers selected from the polymer having the repeating unit shown by the general formula (4) and/or (5). Below, the material (compound and polymer) for forming an organic film will be described further.

<Compound Used in Composition for Forming Organic Film>

The compound used in the inventive composition for forming an organic film can be the compound shown by the following general formula (1) and/or (2).

(1)

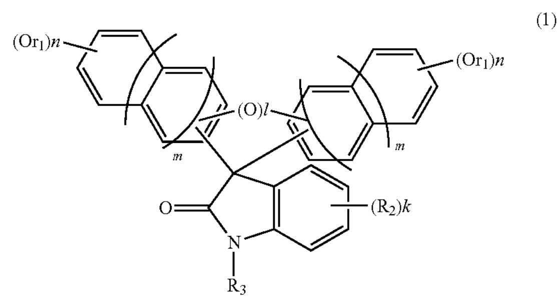

In the general formula (1), $R_1$, $R_2$, $R_3$, "m", "n", "l", and "k" are as defined above.

(2)

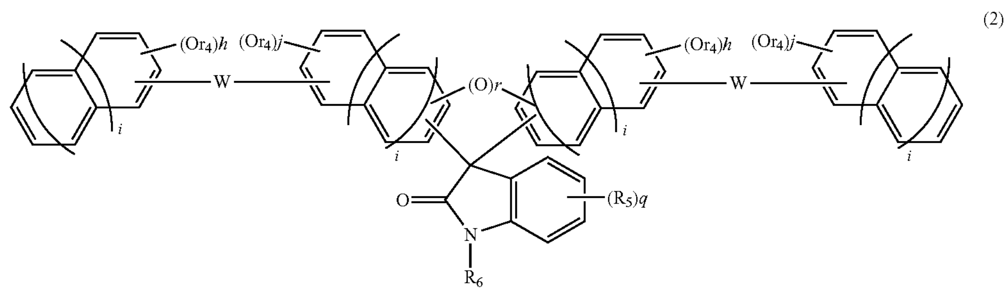

In the general formula (2), $R_4$, $R_5$, $R_6$, "i", "q", "h", "j", and "r" are as defined above, and W represents a single bond or one of the divalent groups shown by the following formulae (3).

(3)

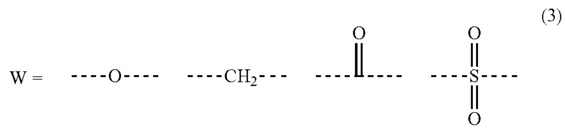

A broken line represents an attachment point.

$R_1$ to $R_6$, "k", "l", "m", "n", "h", "i", "j", "q", and "r" in the general formulae (1) and (2) are as described in the description of the general formulae (I) and (II).

Specific examples of the monomolecular compound shown by the general formula (1) include the following. $R_1$, $R_2$, $R_3$, and "k" are as defined above. In particular, structures that satisfy k=0, l=0, and m=0 in the general formula (1) are preferable from the viewpoint of improving filling and flatness.

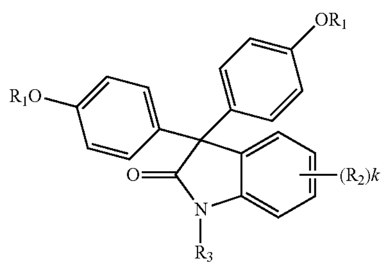

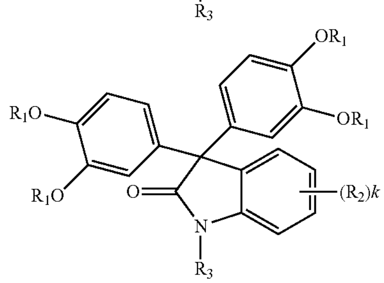

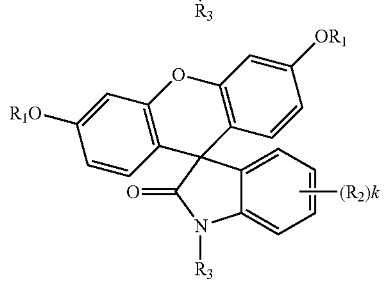

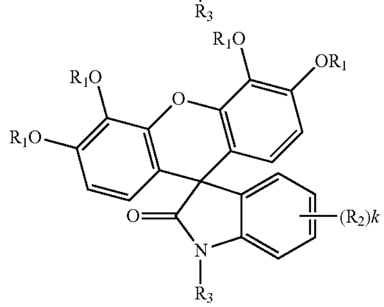

-continued

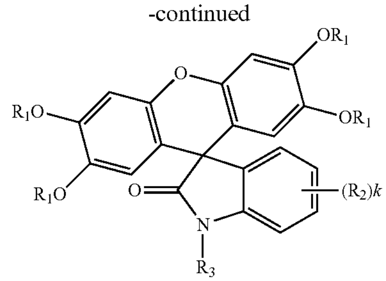

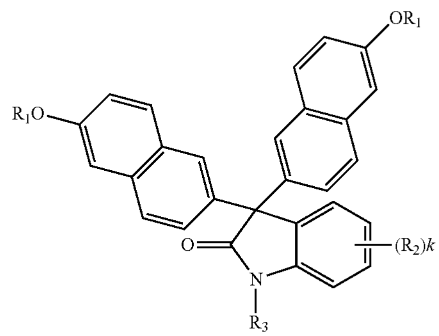

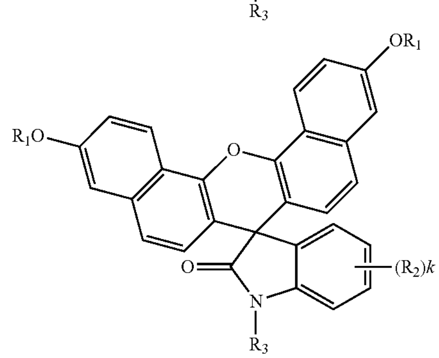

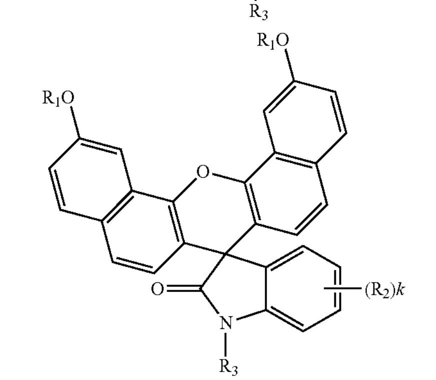

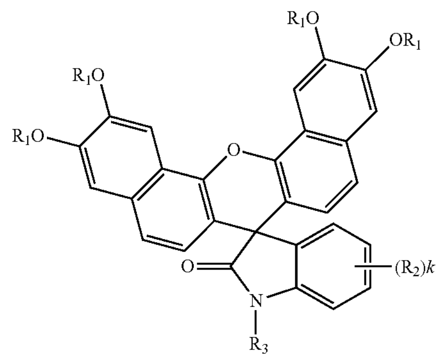

-continued
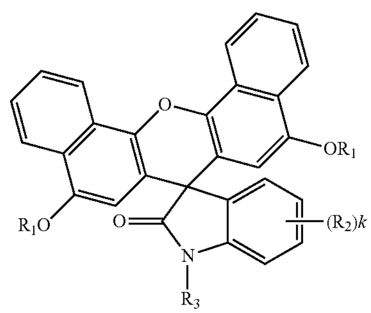
Specific examples of the monomolecular compound shown by the general formula (2) include the following. $R_4$, $R_5$, $R_6$, and "q" are as defined above. In particular, structures that satisfy i=0, q=0, r=0 in the general formula (2) are preferable from the viewpoint of improving filling and flatness.
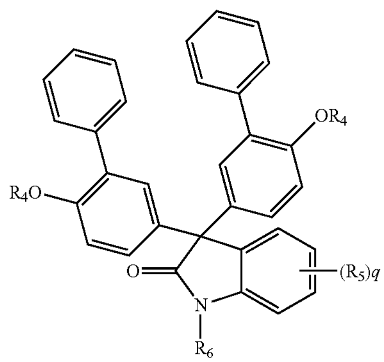
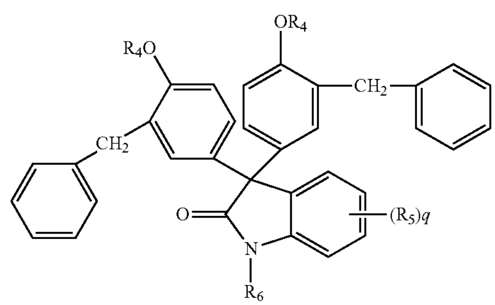
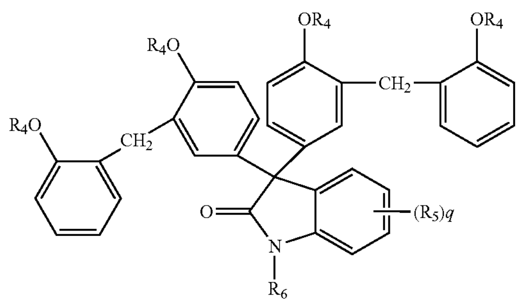
-continued
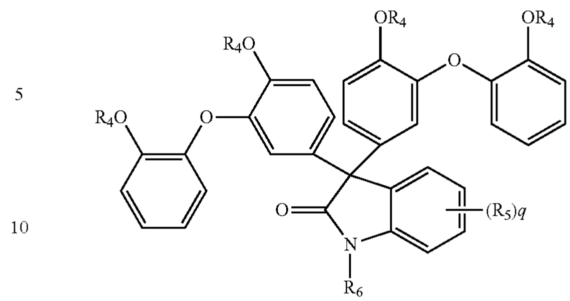
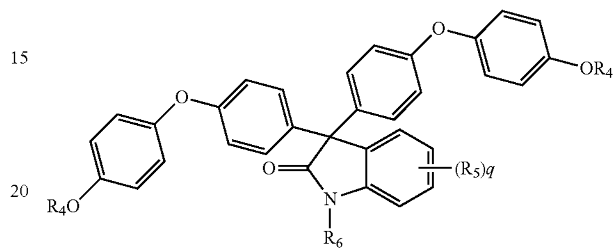
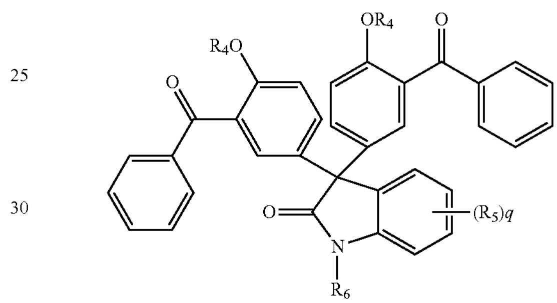
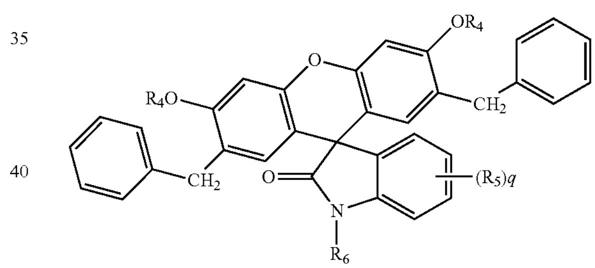
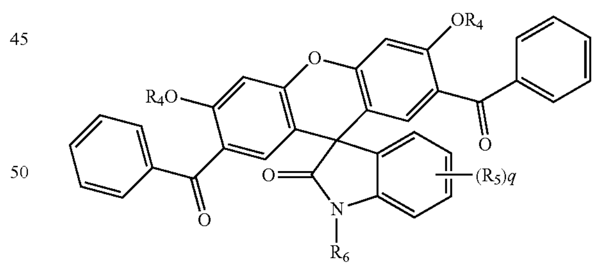
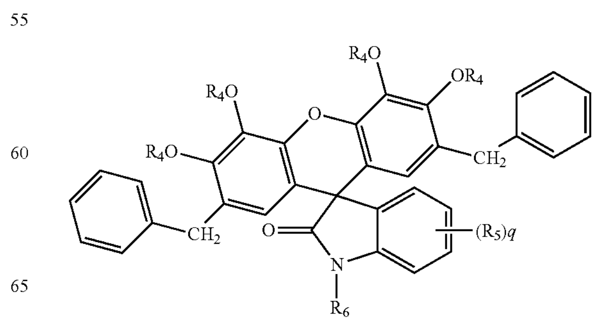

-continued

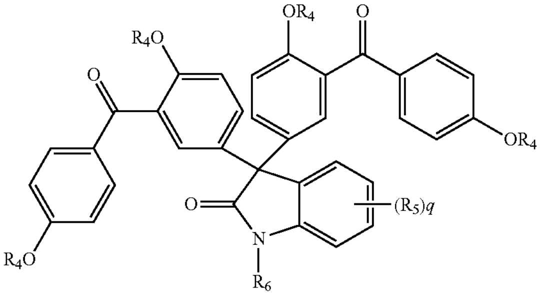

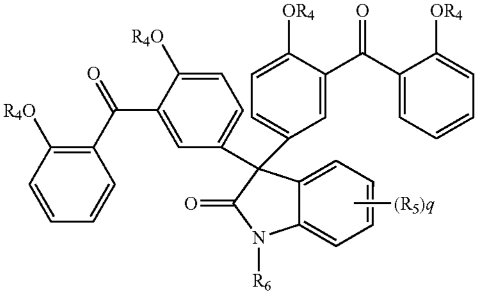

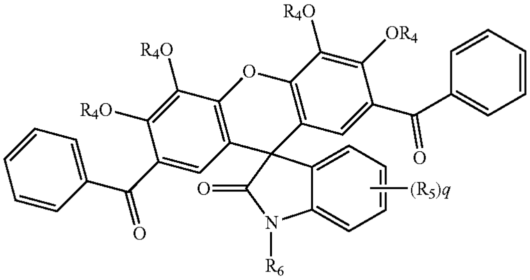

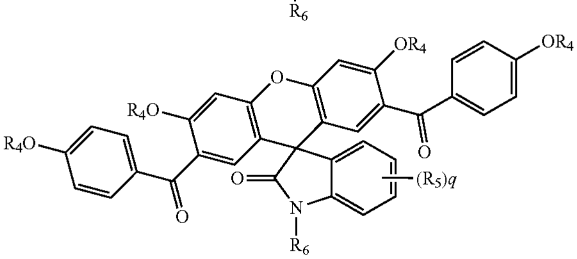

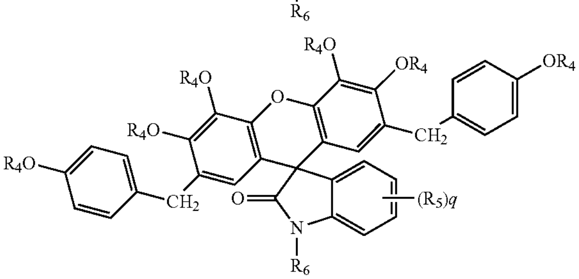

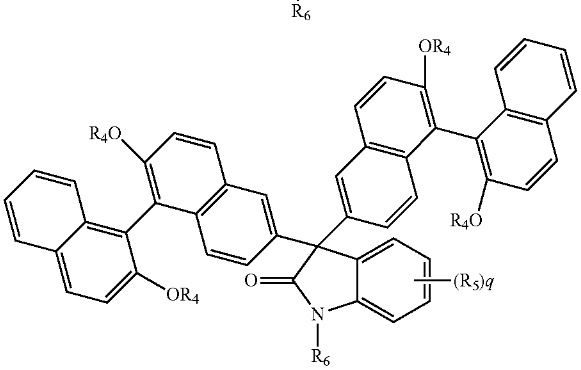

-continued

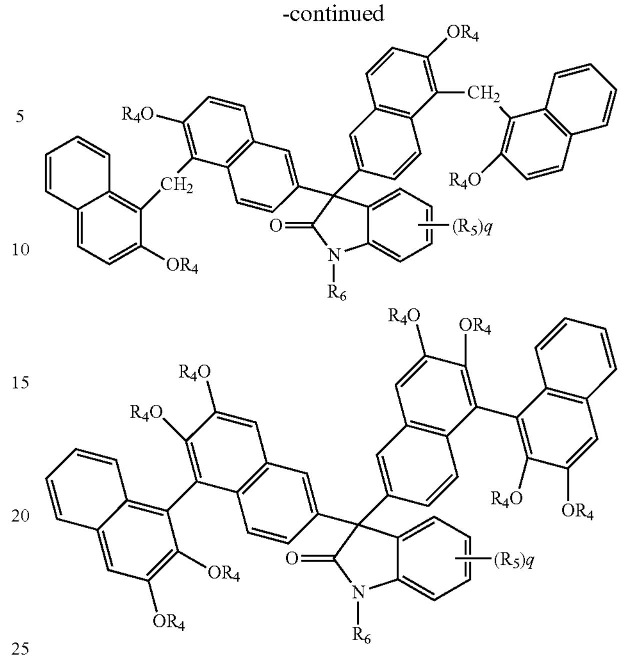

In addition, the compound shown by the above-described general formula (1) or/and (2) preferably satisfies 1.00≤Mw/Mn≤1.10, where Mw is a weight-average molecular weight and Mn is a number-average molecular weight measured by gel permeation chromatography (GPC) in terms of polystyrene. From the definition, Mw/Mn is 1.00 when the compound is a monomolecular compound. However, for reasons of separability in GPC, the measured value exceeds 1.00 in some cases. Generally, it is extremely difficult to bring Mw/Mn close to 1.00 in a polymer having a repeating unit unless a special polymerization method is used, there is a molecular weight distribution, and Mw/Mn becomes a value greater than 1. In the present invention, 1.00≤Mw/Mn≤1.10 has been defined as an index indicating monomerism in order to distinguish between a monomolecular compound and a polymer.

By controlling the Mw/Mn of the compound used in the composition for forming an organic film within such a range, an organic film excellent in filling property and flatness can be formed.

The inventive compound has a structure containing many aromatic rings, and therefore, has excellent heat resistance and etching resistance. Furthermore, the compound can contain a combination of various substituents for providing flowability and curability and various heterocyclic structures for providing film-formability and adhesiveness, and is useful as a compound used in a composition for forming an organic film.

[Method for Manufacturing Compound]

Examples of methods for manufacturing the inventive compounds shown by the general formulae (1) and (2) include a method of obtaining the compound by a dehydration condensation reaction as shown below between an indole-2,3-dione and an aromatic compound having $OR_1$ or $OR_4$ as a substituent while using an acid catalyst. Here, when aromatic rings form a cyclic ether structure with one another, that is l=1 or r=1 in the general formulae (1) and (2), an ether bond is formed by the aromatic compound having a hydroxy group in a specific substitution position.

(In the Case of General Formula (1))

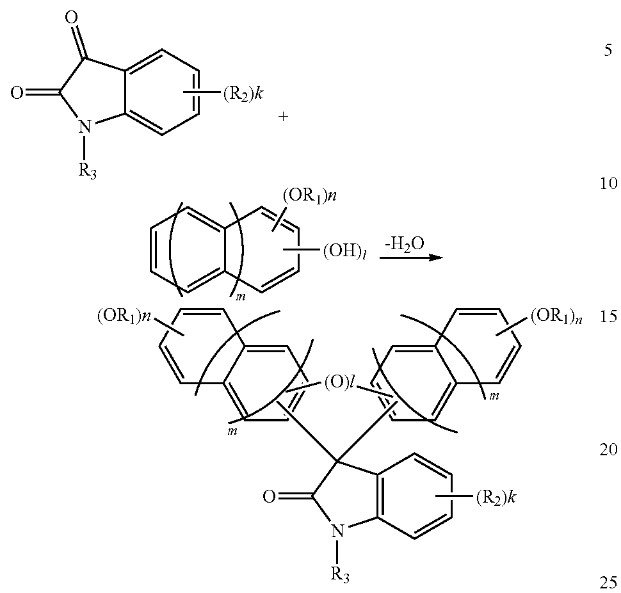

(In the Case of General Formula (2))

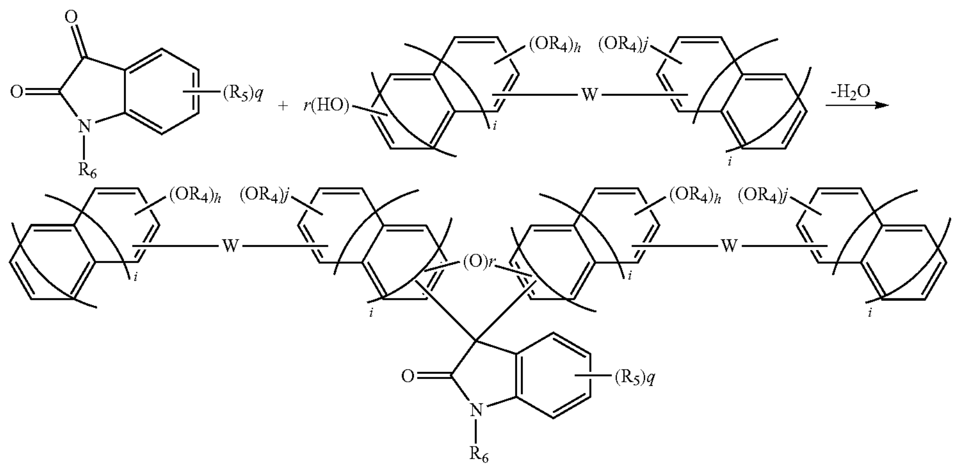

pyl alcohol, butanol, ethylene glycol, propylene glycol, diethylene glycol, glycerol, ethylene glycol monomethyl ether, and propylene glycol monomethyl ether; ethers, such as diethyl ether, dibutyl ether, diethylene glycol diethyl ether, diethylene glycol dimethyl ether, tetrahydrofuran, and 1,4-dioxane; chlorinated solvents, such as methylene chloride, chloroform, dichloroethane, and trichloroethylene; hydrocarbons, such as hexane, heptane, benzene, toluene, xylene, and cumene; nitriles, such as acetonitrile; ketones, such as acetone, ethyl methyl ketone, and isobutyl methyl ketone; esters, such as ethyl acetate, n-butyl acetate, and propylene glycol methyl ether acetate; aprotic polar solvents, such as dimethylsulfoxide, N,N-dimethylformamide, and hexamethylphosphoric triamide; and the like. One of these can be used, or two or more thereof can be used in mixture. These solvents can be used in a range of 0 to 2000 parts by mass based on 100 parts by mass of the reactants. The reaction temperature is preferably −50° C. to approximately the boiling point of the solvent, and room temperature to 150° C. is even more preferable. Reaction time is appropriately selected from 0.1 to 100 hours.

Reaction methods include: a method of charging the indole-2,3-dione and the aromatic compound at once with the acid catalyst, being a catalyst; a method of dispersing or dissolving the indole-2,3-dione and the aromatic compound, then adding the catalyst at once or separately or diluting the catalyst with a solvent and adding dropwise; and a method of dispersing or dissolving the catalyst, then adding each of the indole-2,3-dione and the aromatic compound at once or separately, or diluting the indole-2,3-dione and the aromatic compound with a solvent and adding dropwise. In this event, 2 mol or more of the aromatic compound is preferably used relative to 1 mol of the indole-2,3-dione, although this also depends on the reactivity of the aromatic compound. After completion of the reaction, the reaction product can be diluted with an organic solvent, then liquid-liquid separation and washing can be performed to collect the target compound in order to remove the catalyst used in the reaction.

The organic solvent used in this event is not particularly limited, as long as the organic solvent is capable of dissolving the target compounds and is separated into two layers even when mixed with water. Examples of the organic solvent include hydrocarbons, such as hexane, heptane, benzene, toluene, and xylene; esters, such as ethyl acetate, n-butyl acetate, and propylene glycol methyl ether acetate;

As the acid catalyst used in the above-described dehydration condensation reaction, the following can be used: inorganic acids, such as hydrochloric acid, hydrobromic acid, sulfuric acid, nitric acid, phosphoric acid, and heteropoly acid; organic acids, such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide. The amount of the catalyst to be used is in the range of 0.1 to 20 mol, preferably 0.2 to 10 mol based on the number of moles of the intermediate indole-2,3-dione.

The solvent used is not particularly limited, and examples thereof include: alcohols, such as methanol, ethanol, isoproketones, such as methyl ethyl ketone, methyl amyl ketone, cyclohexanone, and methyl isobutyl ketone; ethers, such as diethyl ether, diisopropyl ether, methyl-t-butyl ether, and ethylcyclopentylmethyl ether; chlorinated solvents, such as methylene chloride, chloroform, dichloroethane, and trichloroethylene; mixtures thereof; etc. As washing water used in this event, generally, what is called deionized water or ultrapure water may be used. The washing may be performed one or more times, preferably approximately one to five times because washing ten times or more does not always produce the full washing effects thereof.

In the liquid-liquid separation and washing, the washing may be performed with a basic aqueous solution to remove the acidic components in the system or to remove remaining aromatic compounds. The base specifically includes hydroxides of alkaline metals, carbonates of alkaline metals, hydroxides of alkali earth metals, carbonates of alkali earth metals, ammonia, organic ammonium, etc.

Further, in the liquid-liquid separation and washing, the washing may be performed with an acidic aqueous solution to remove the metal impurities or basic components in the system. The acid specifically includes inorganic acids, such as hydrochloric acid, hydrobromic acid, sulfuric acid, nitric acid, phosphoric acid, and heteropoly acid; organic acids, such as oxalic acid, fumaric acid, maleic acid, trifluoroacetic acid, methanesulfonic acid, benzenesulfonic acid, p-toluenesulfonic acid, and trifluoromethanesulfonic acid; etc.

The liquid-liquid separation and washing may be performed with either one of the basic aqueous solution and the acidic aqueous solution, or can be performed with a combination of the two. The liquid-liquid separation and washing is preferably performed with the basic aqueous solution and the acidic aqueous solution in this order from the viewpoint of removing the metal impurities.

After the liquid-liquid separation and washing with the basic aqueous solution and the acidic aqueous solution, washing with neutral water may be successively performed. The washing may be performed one or more times, preferably approximately one to five times. As the neutral water, deionized water, ultrapure water, or the like as mentioned above may be used. The washing may be performed one or more times, but if the washing is not performed sufficiently, the basic components and acidic components cannot be removed in some cases. The washing is preferably performed approximately one to five times because washing ten times or more does not always produce the full washing effects thereof.

Further, the reaction product after the liquid-liquid separation can also be collected as a powder by concentrating and drying up the solvent or crystallizing the reaction product under reduced pressure or normal pressure. Alternatively, the reaction product can also be retained in the state of solution with an appropriate concentration to improve the workability in preparing the composition for forming an organic film. The concentration in this event is preferably 0.1 to 50 mass %, more preferably 0.5 to 30 mass %. With such a concentration, the viscosity is hardly increased, making it possible to prevent degradation of the workability; in addition, since the amount of the solvent is not excessive, it is economical.

The solvent in this event is not particularly limited, as long as the solvent is capable of dissolving the compound. Specific examples of the solvent include ketones, such as cyclohexanone and methyl-2-amyl ketone; alcohols, such as 3-methoxybutanol, 3-methyl-3-methoxybutanol, 1-methoxy-2-propanol, and 1-ethoxy-2-propanol; ethers, such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. One of these or a mixture of two or more thereof can be used.

<Polymer Used in Composition for Forming Organic Film>

The inventive polymer used in a composition for forming an organic film can be a polymer having a repeating unit shown by the following general formula (4) or/and (5).

(4)

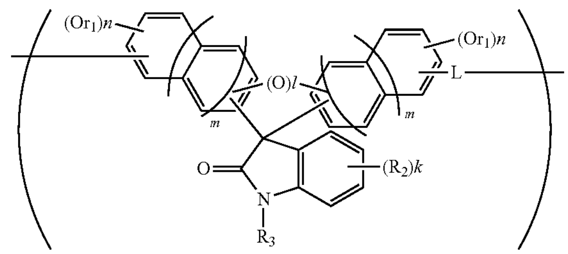

In the general formula (4), $R_1$, $R_2$, $R_3$, "n", "m", "l", and "k" are as defined above, and L represents a divalent organic group having 1 to 40 carbon atoms.

(5)

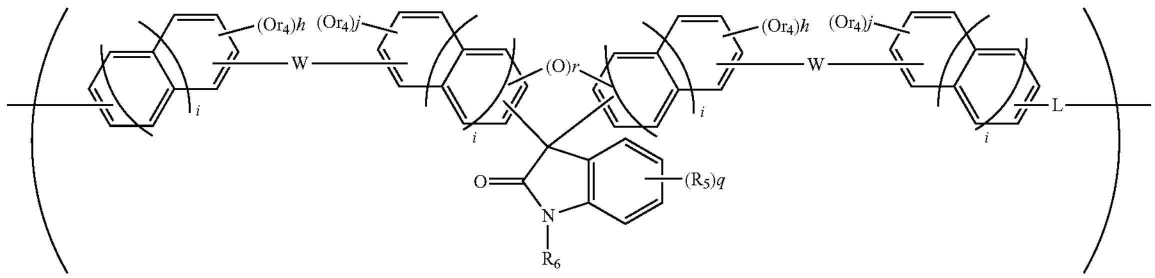

In the general formula (4), $R_4$, $R_5$, $R_6$, W, L, "h", "i", "j", "q", and "r" are as defined above.

These polymers are obtained using the compounds shown by the general formulae (1) and (2), and since the above-described compounds are used, have excellent heat resistance, flatness, and thermosetting property. Furthermore, since these are polymers having a repeating unit rather than a monomer, the amount of outgas components is small. In addition, since the polymer has a molecular weight distribution, crystallinity is eased, so that improvement of film-formability can also be expected.

The linking group L constituting the repeating units of the general formulae (4) and (5) is a divalent organic group having 1 to 40 carbon atoms, and specific examples include the following or the like.

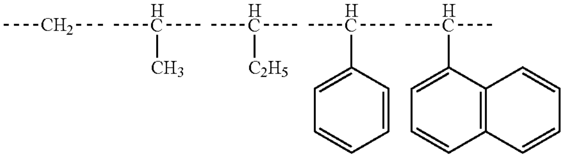

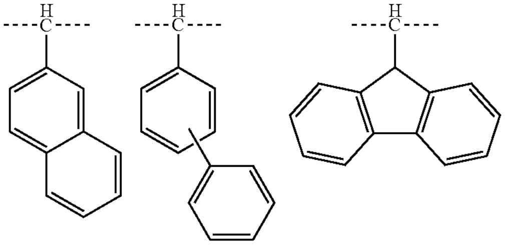

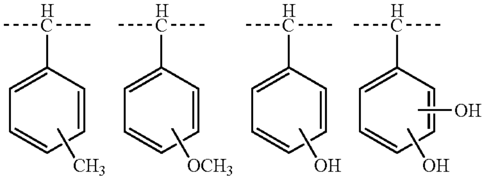

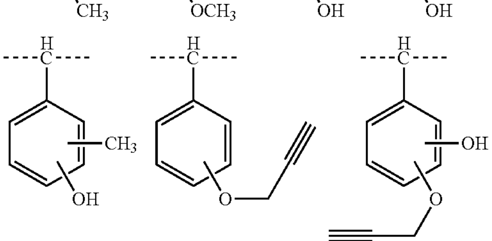

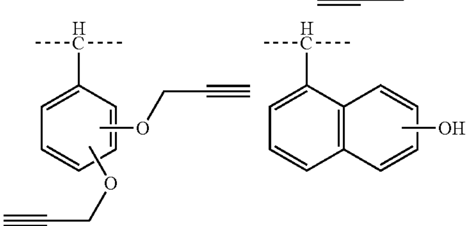

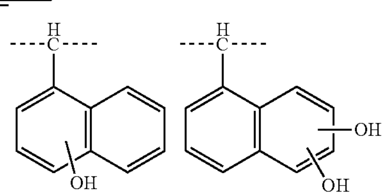

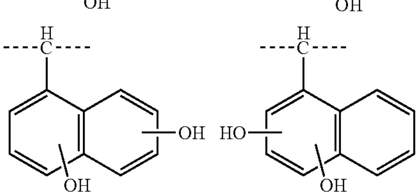

-continued

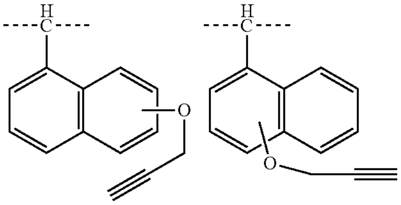

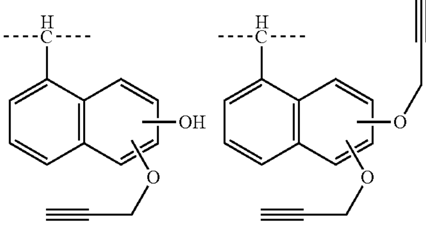

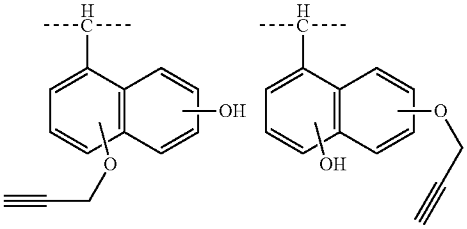

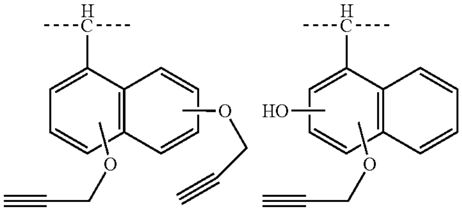

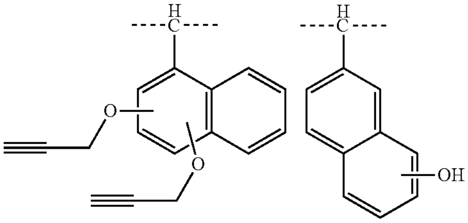

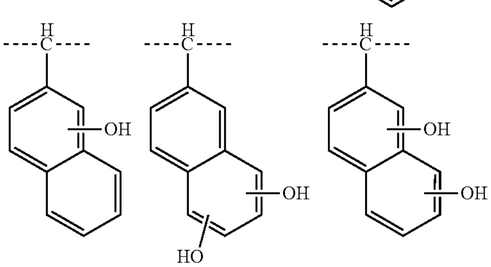

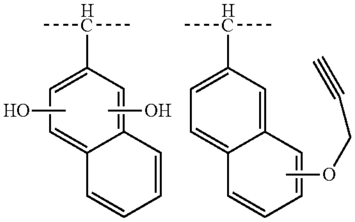

-continued
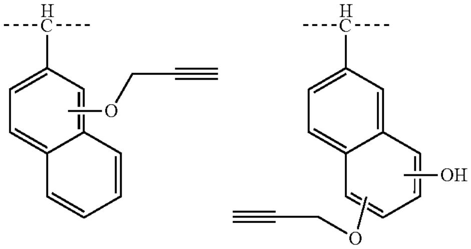
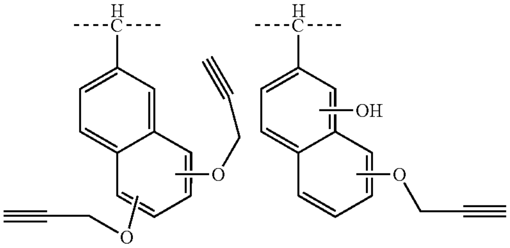
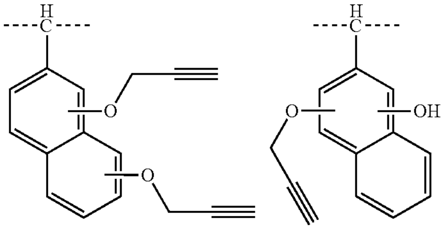
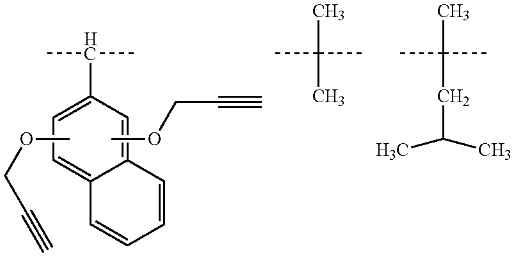
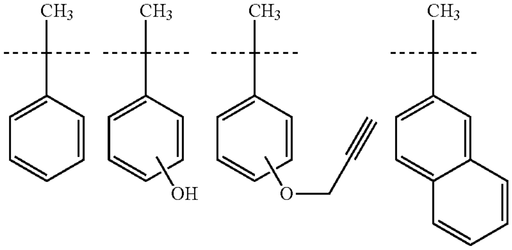
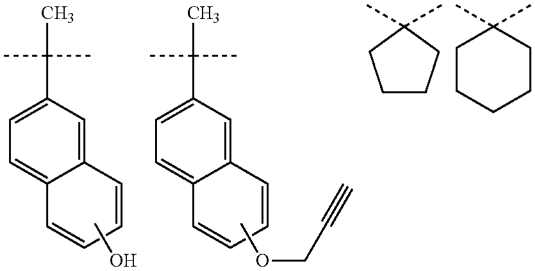
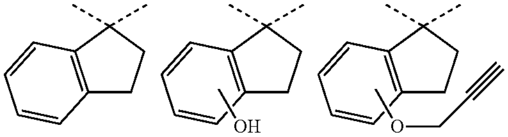
-continued
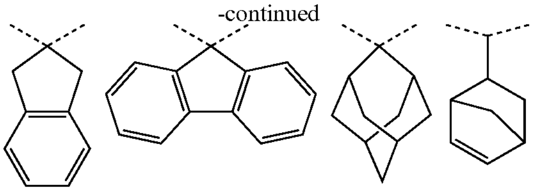
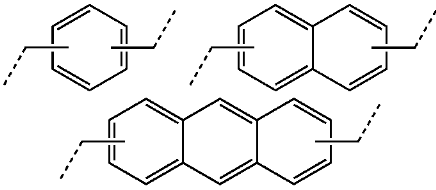
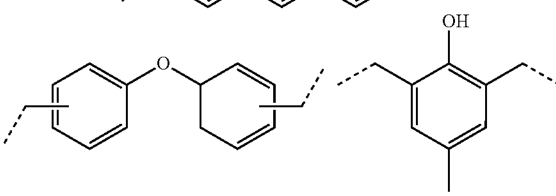
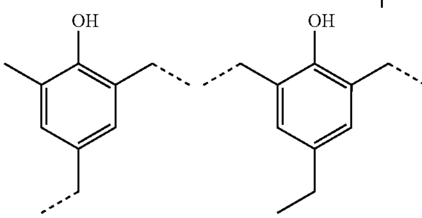
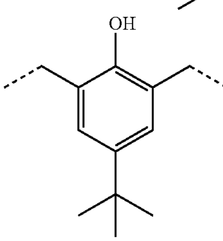
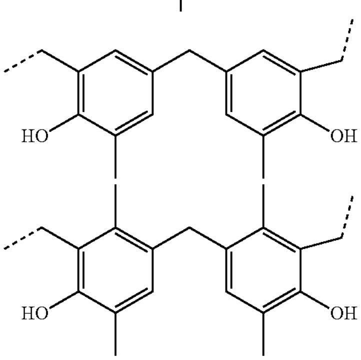
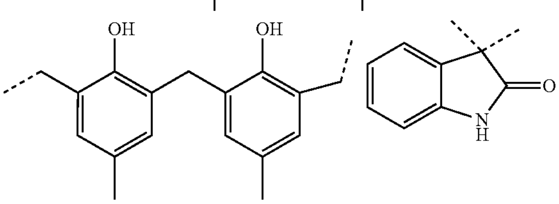
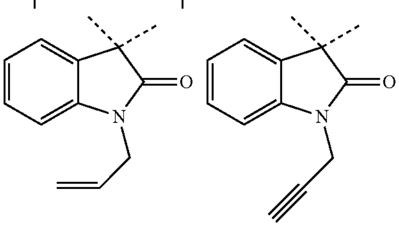

-continued

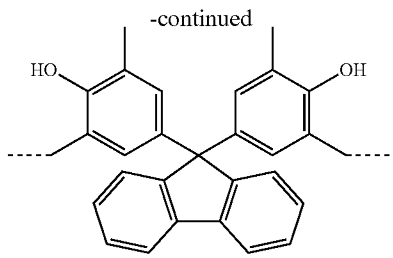

Furthermore, the linking group L of the above-described polymers is preferably the following general formula (6).

(6)

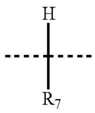

In the general formula, $R_7$ represents a hydrogen atom or an aromatic ring-containing organic group having 1 to 20 carbon atoms, and a broken line represents an attachment point.

Specific examples of the general formula (6) include the following. In particular, in view of the availability of raw materials, a methylene group is preferable. That is, $R_7$ is preferably a hydrogen atom.

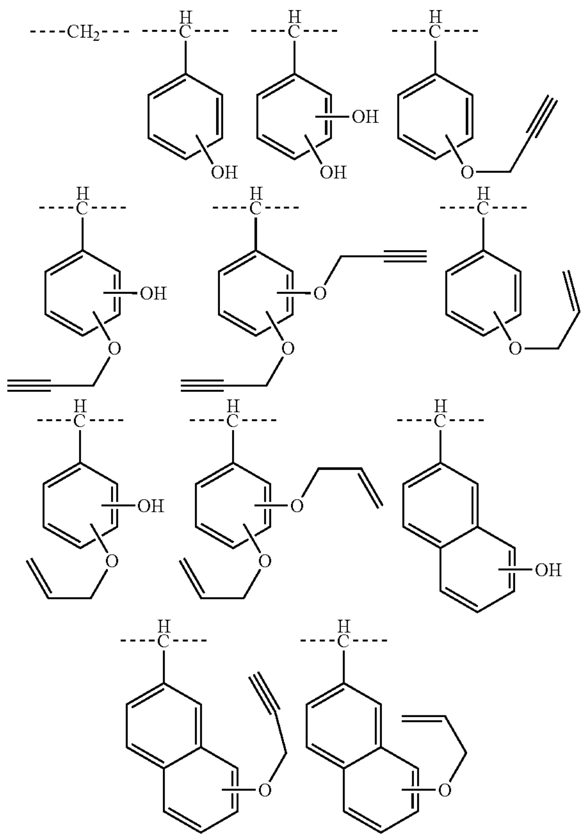

Furthermore, the Mw (weight-average molecular weight) of the above-described polymer is preferably 1000 to 5000, and the Mw is further preferably 1000 to 4000. Note that the molecular weight can be determined as a weight-average molecular weight (Mw) measured by gel permeation chromatography (GPC) using tetrahydrofuran as an eluent in terms of polystyrene.

When the molecular weight is within such a range, solubility in organic solvents can be ensured, and sublimation products that are generated when baking can be suppressed. In addition, the thermal flowability of the polymer used in a composition for forming an organic film becomes favorable. Therefore, when blended in a material, the polymer can not only favorably fill a fine structure formed on a substrate, but also form an organic film having the entire substrate planarized.

[Method for Manufacturing Polymer]

As a means for obtaining the polymer used in the inventive composition for forming an organic film, the polymer can be obtained by a polycondensation reaction between the compound shown by the general formula (1) or (2) and an aldehyde or a ketone or a benzyl alcohol while using an acid catalyst. The $R_1$, $R_2$, $R_3$, $R_4$, $R_5$, $R_6$, "h", "i", "j", "n", "m", "l", "k", "q", "r", W, and L in the following formulae are as defined above and $R_8$ and $R_9$ represent a hydrogen atom or a monovalent organic group. When one or both of $R_8$ and $R_9$ are hydrogen atoms, an aldehyde is indicated, otherwise, a ketone is indicated, and polycondensation with the compound shown by the general formula (1) or (2) is indicated. $R_8$ preferably represents a hydrogen atom, and $R_9$ preferably represents a hydrogen atom or an aromatic ring-containing organic group having 1 to 20 carbon atoms. AR represents an aromatic compound such as benzene and naphthalene, and the substituent represented by $—CH_2—OH$ is a substituent of the aromatic ring.

(In the Case of General Formula (4))

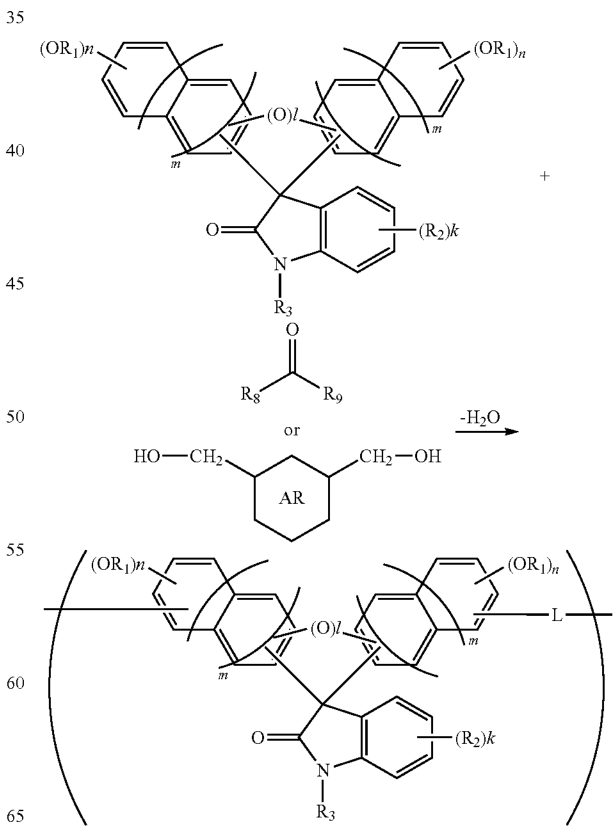

(In the Case of General Formula (5))

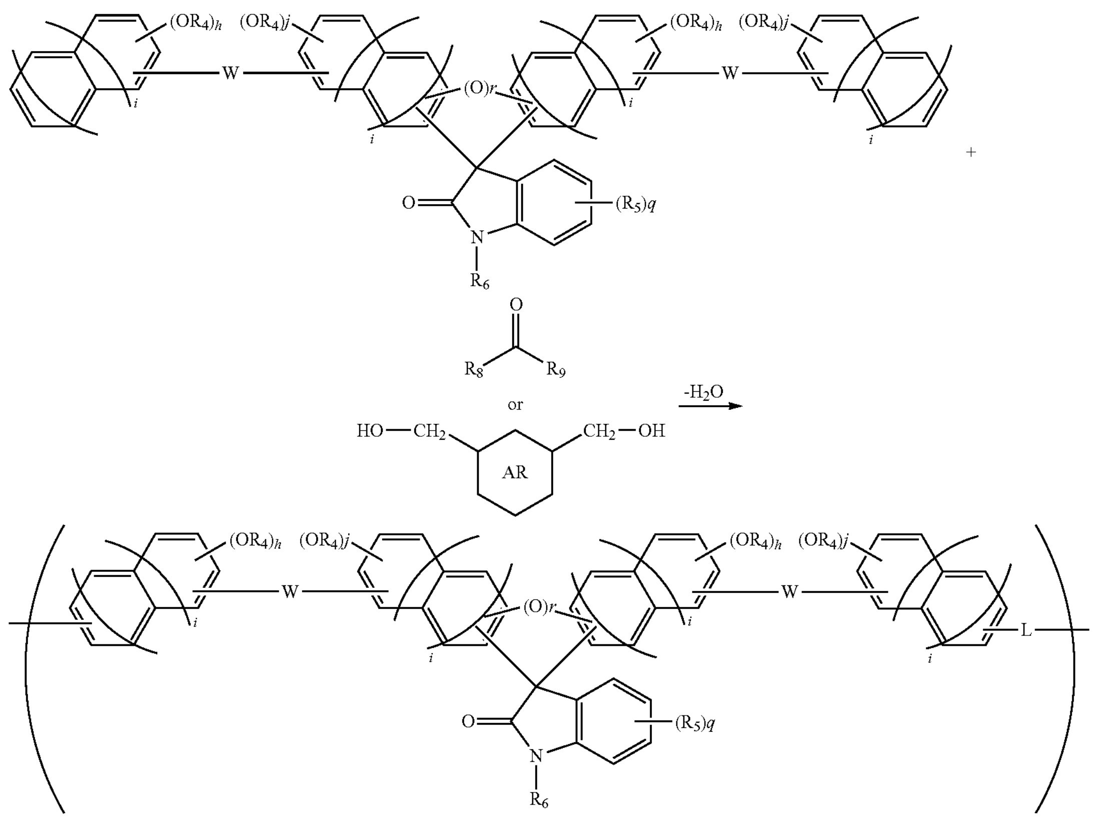

The above-described polycondensation reaction can generally be achieved in an organic solvent in the presence of an acid catalyst at room temperature or under cooling or heating as necessary. As the acid catalyst used, the following can be used: inorganic acids, such as hydrochloric acid, hydrobromic acid, sulfuric acid, nitric acid, phosphoric acid, and heteropoly acid; organic acids, such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

Examples of the solvent used include: alcohols, such as methanol, ethanol, isopropyl alcohol, butanol, ethylene glycol, propylene glycol, diethylene glycol, glycerol, ethylene glycol monomethyl ether, and propylene glycol monomethyl ether; ethers, such as diethyl ether, dibutyl ether, diethylene glycol diethyl ether, diethylene glycol dimethyl ether, tetrahydrofuran, and 1,4-dioxane; chlorinated solvents, such as methylene chloride, chloroform, dichloroethane, and trichloroethylene; hydrocarbons, such as hexane, heptane, benzene, toluene, xylene, and cumene; nitriles, such as acetonitrile; ketones, such as acetone, ethyl methyl ketone, and isobutyl methyl ketone; esters, such as ethyl acetate, n-butyl acetate, and propylene glycol methyl ether acetate; aprotic polar solvents, such as dimethylsulfoxide, N,N-dimethylformamide, and hexamethylphosphoric triamide; and the like. One of these can be used, or two or more thereof can be used in mixture.

Regarding methods for performing the reaction and methods for collecting the polymer, the methods described in the method for manufacturing the compounds shown by the general formulae (1) and (2) can be performed.

[Different Method for Manufacturing Compound and Polymer]

When the $R_1$ and $R_4$ in the compounds shown by the general formulae (1) and (2) or the polymers shown by the general formulae (4) and (5) used in the inventive composition for forming an organic film are not hydrogen atoms, examples of a different manufacturing method include a method including the steps of: obtaining an intermediate by a dehydration condensation reaction by using, as raw materials, an indole-2,3-dione shown below, an aromatic compound having a hydroxy group, a so-called phenol or naphthol, and using an acid catalyst (STEP 1); and performing a substitution reaction between a hydroxy group of the obtained aromatic compound and a raw material having a leaving group X shown by $R_1$—X or $R_4$—X while using a base catalyst (STEP 2-1). Alternatively, the polymer can be obtained by performing a polycondensation reaction (STEP 2-2) by using the compound obtained in (STEP 1), and then, a hydroxy group can be converted to $OR_1$ by a method including performing a substitution reaction (STEP 3) where a compound having a leaving group X shown by $R_1$—X or $R_4$—X is used as a raw material while using a base catalyst. Thus, the polymer can be obtained. In this case, one kind of the $R_1$—X or $R_4$—X can be used or two or more kinds thereof can be used, and by further controlling the reaction rate, the ratio of hydroxy groups to $OR_1$ or $OR_4$ can also be controlled. By partly introducing a polar structure such as a hydroxy group, film-formability and adhesion of the film to a substrate can also be controlled. When the $R_1$ and $R_3$ in the compound shown by the general formula (1) and the $R_1$ and $R_3$ in the polymer shown by the general formula (4) are identical and when the $R_4$ and $R_6$ in the compound shown by the general formula (2) and the $R_4$ and $R_6$ in the polymer shown by the general formula (5) are identical, only examples of the general formula (1) will be given. Furthermore, it is also possible to use a raw material in which the $R_1$ of the indole-2,3-dione is a hydrogen atom, convert the hydroxy groups in the aromatic compound by the method shown by (STEP 2-1) to introduce $R_1$, and at the same time, introduce $R_3$. A similar method can also be applied to the compound of the general formula (2) and the polymers of the general formulae (4) and (5). $R_1$, $R_2$, $R_3$, $R_4$, $R_5$, $R_6$, $R_8$, $R_9$, "h", "i", "j", "n", "m", "l", "k", "q", "r", W, L, and AR are as defined above.

In the case of general formula (1) and general formula (4)

(STEP 1)

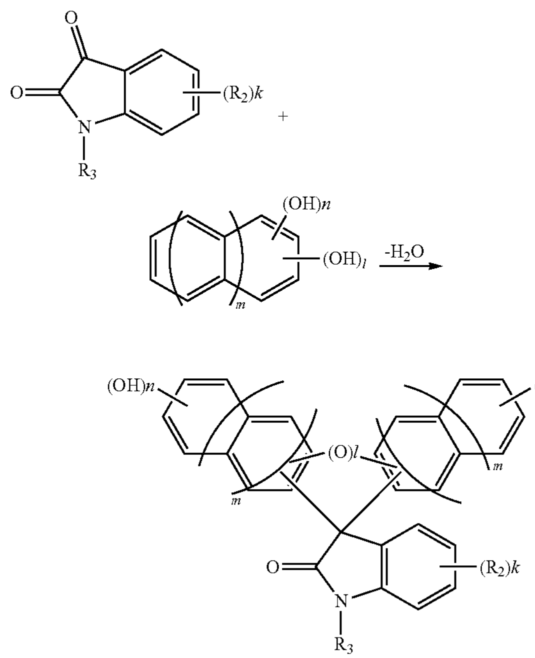

(STEP 2-1)

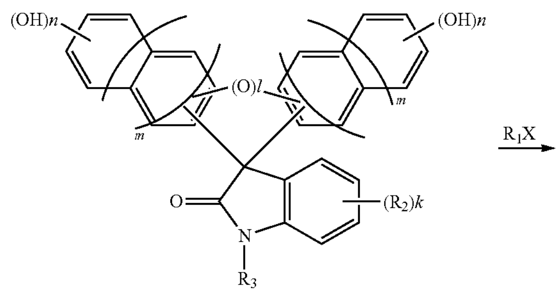

-continued

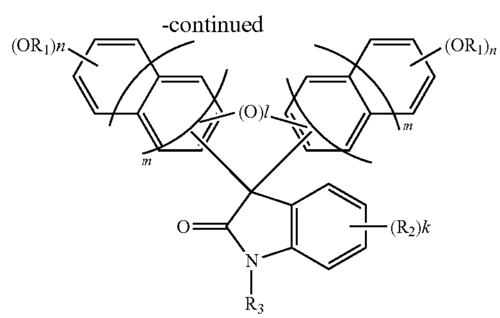

(STEP 2-2)

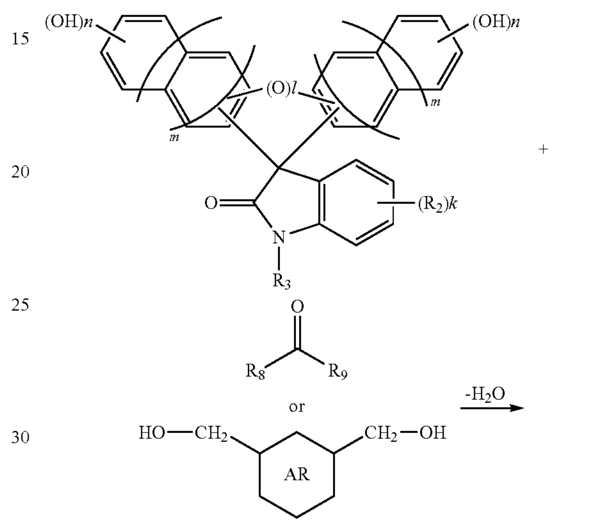

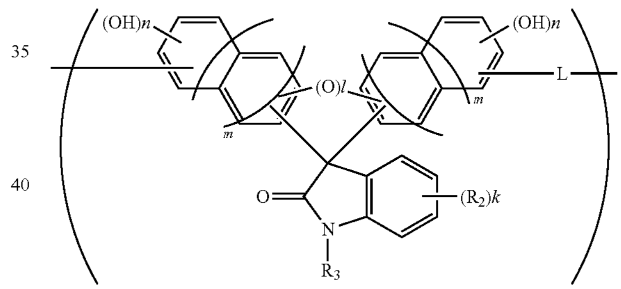

(STEP 3)

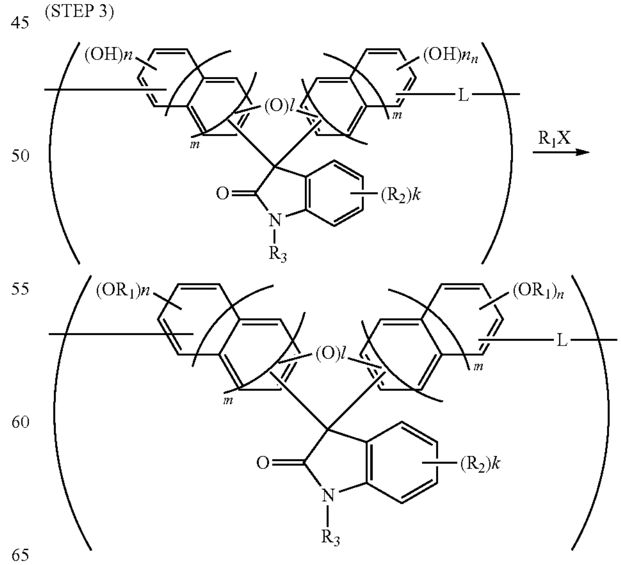

In the case of general formula (2) and general formula (5)
(STEP 1)
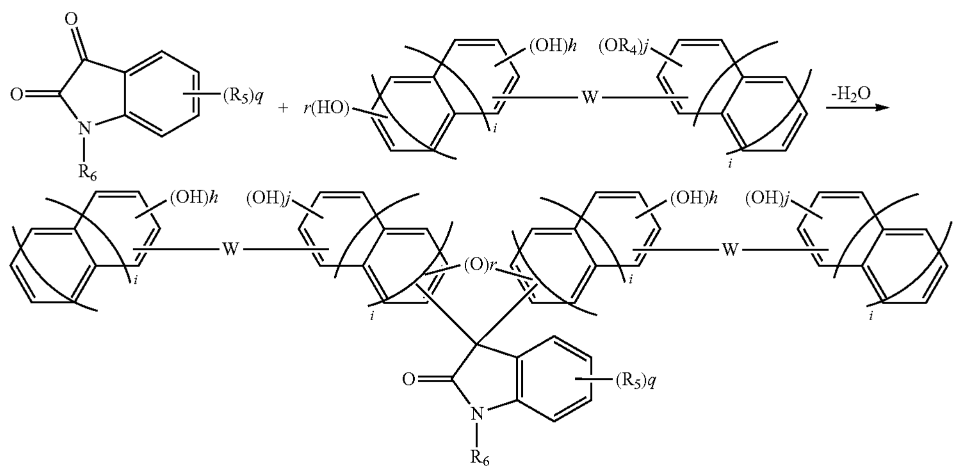
(STEP 2-1)
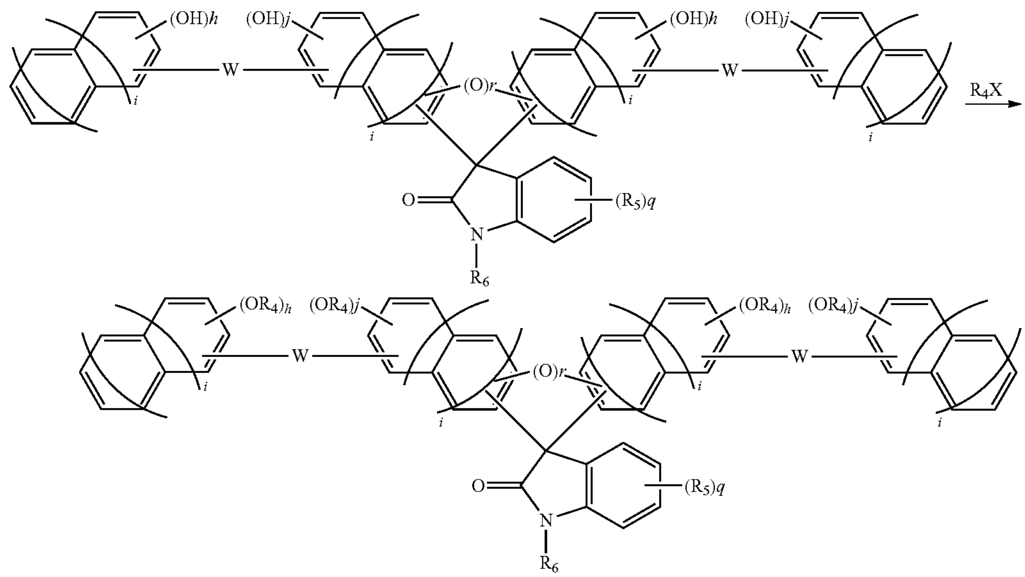
(STEP 2-2)
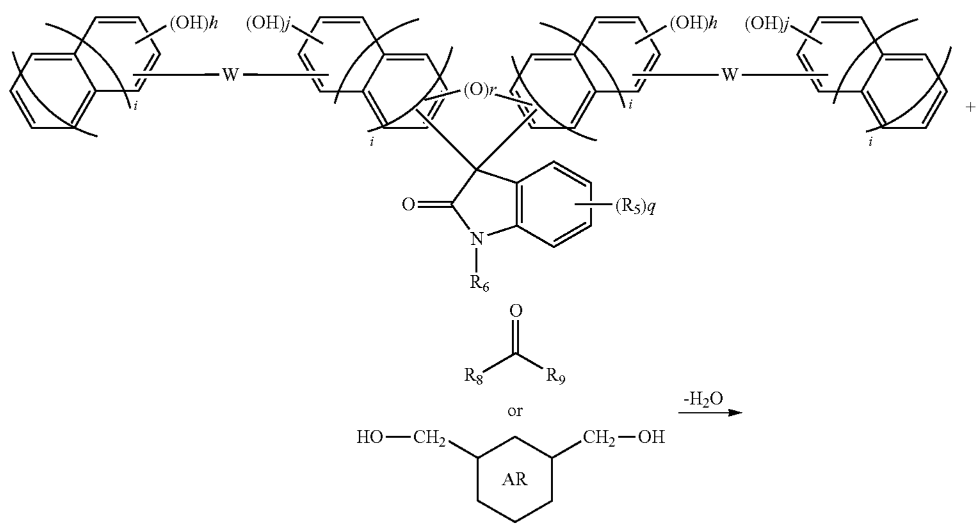

-continued
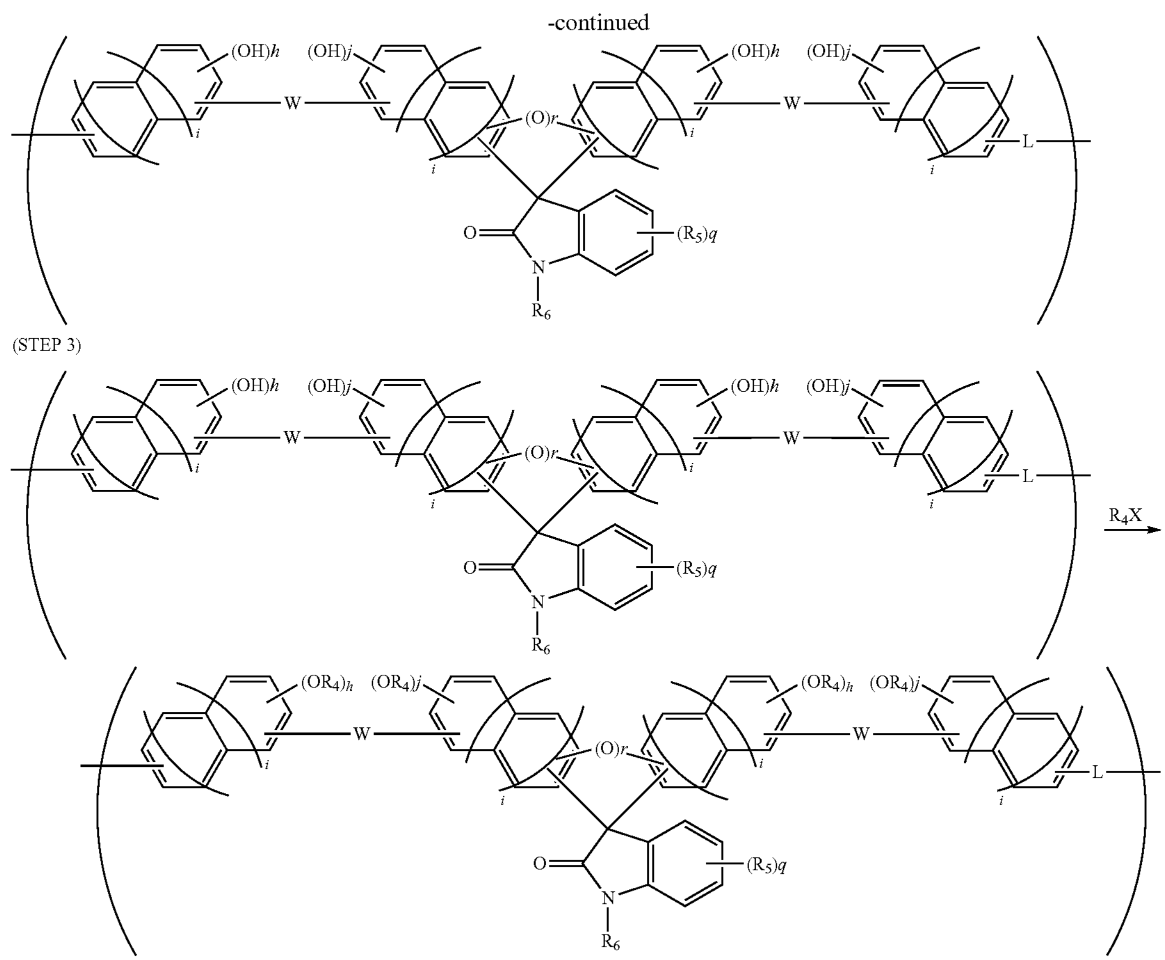
When $R_1$=$R_3$ in general formula (1)
(STEP 1)
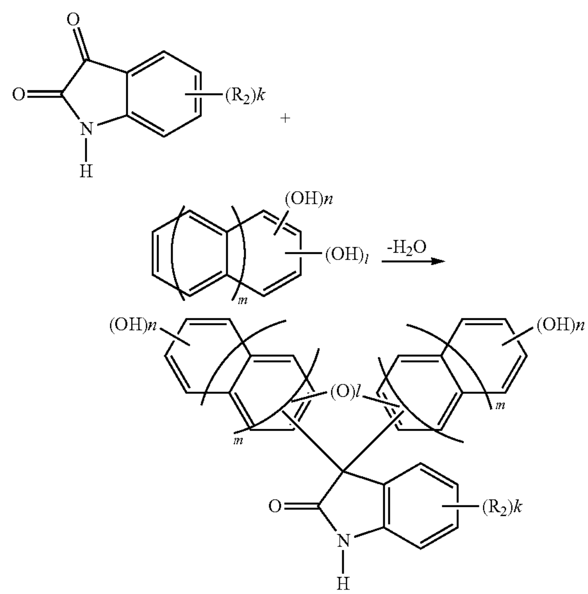
-continued
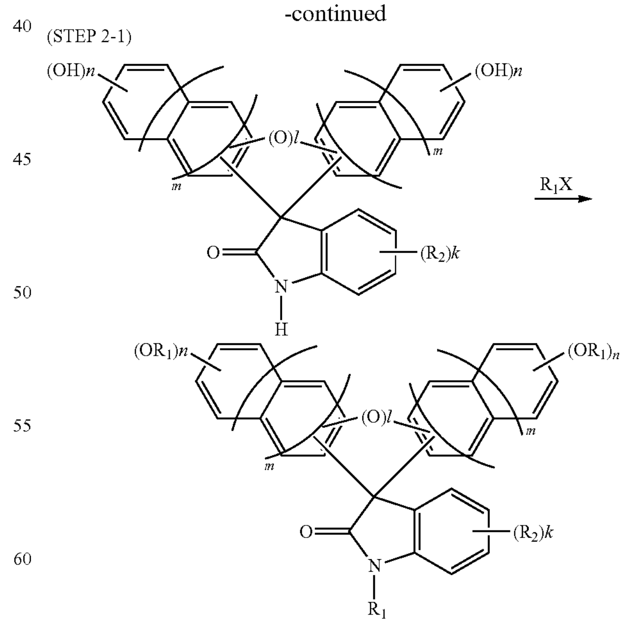
The dehydration condensation reaction of (STEP 1) and the polycondensation reaction of (STEP 2-2) can be performed by the methods described in the methods for manufacturing the compounds of the general formulae (1) and (2) and the polymers of the general formulae (4) and (5) respectively. The reaction method and the method for collecting the compound or polymer can be performed by the methods described in the methods for manufacturing the compounds shown by the general formulae (1) and (2).

Examples of the base catalyst used in the substitution reaction in (STEP 2-1) and (STEP 3) include inorganic base compounds, such as sodium hydrogen carbonate, sodium carbonate, potassium carbonate, calcium carbonate, cesium carbonate, sodium hydroxide, potassium hydroxide, sodium hydride, and potassium phosphate; organic amine compounds, such as triethyl amine, pyridine, and N-methylmorpholine; and the like. One of these may be used, or two or more thereof may be used in combination.

The solvent used in this event is not particularly limited, as long as the solvent is inert in the above reaction. Examples of the solvent include ether-based solvents, such as diethyl ether, tetrahydrofuran, and dioxane; aromatic solvents, such as benzene, toluene, and xylene; acetonitrile, dimethylsulfoxide, N,N-dimethylformamide, N-methylpyrrolidone, water, and the like. One of these or a mixture of two or more thereof can be used.

The method for performing the substitution reaction and the method for collecting the compound or polymer can be performed by the methods described in the methods for manufacturing the compounds shown by the general formulae (1) and (2).

To prepare the compound or polymer used in the composition for forming an organic film obtained by this method, one of various halides, tosylates, and mesylates can be used or the combination of two or more thereof can be used according to the required performance. For example, those having a side chain structure that contributes to improvement of planarizing property, a rigid aromatic ring structure that contributes to etching resistance and heat resistance, and so forth can be combined at any proportion. Therefore, a composition for forming an organic film using these compounds and polymers can achieve both higher filling and planarizing properties and etching resistance.

As described above, the inventive compound or polymer used in a composition for forming an organic film gives a composition for forming an organic film that is excellent in film-formability and filling and planarizing properties.

<Composition for Forming Organic Film>

In addition, the present invention provides a composition for forming an organic film, containing: the above-described inventive compound and/or polymer used in a composition for forming an organic film; and an organic solvent.

[Compound and/or Polymer Used in Composition for Forming Organic Film]

As a material for forming an organic film, one or a combination of two or more of the compound or polymer used in a composition for forming an organic film can be used in the inventive composition for forming an organic film containing the above-described compound and/or polymer used in a composition for forming an organic film and an organic solvent.

Furthermore, in the present invention, one or more compounds selected from the above-described compounds used in a composition for forming an organic film and one or more polymers selected from the above-described polymers used in a composition for forming an organic film are preferably contained. Specifically, the material for forming an organic film preferably contains one or more compounds selected from the compounds shown by the general formula (1) and/or (2) and one or more polymers selected from the polymers having a repeating unit shown by the general formula (4) and/or (5).

In such a mixture, it is possible to adjust, within an appropriate range, various physical properties such as filling and planarizing properties and outgas caused by sublimation products required when using an organic film. That is, the material for forming an organic film may include (i) one or more compounds used in a composition for forming an organic film, (ii) one or more polymers used in a composition for forming an organic film, or (iii) a mixture of one or more compounds selected from the compounds used in a composition for forming an organic film and one or more polymers selected from the polymers used in a composition for forming an organic film. Any combination is possible, and in this manner, it is possible to give an organic film having the desired properties. When only compounds are blended or only polymers are blended, preparation is easy, and when a mixture of compounds and polymers is blended, the degree of freedom for controlling the workability of the composition and the physical properties of the organic film is increased.

[Organic Solvent]

The organic solvent that can be used in the inventive composition for forming an organic film is not particularly limited as long as the solvent can dissolve the compound and/or polymer (base polymer), and when contained, the surfactant, plasticizer, acid generator, crosslinking agent, and other additives described below. Specifically, solvents with a boiling point of lower than 180° C. can be used, such as those disclosed in paragraphs [0091] and [0092] of JP 2007-199653 A. Above all, propylene glycol monomethyl ether acetate, propylene glycol monomethyl ether, 2-heptanone, cyclopentanone, cyclohexanone, and a mixture of two or more thereof are preferably used. The organic solvent is contained in an amount of preferably 200 to 10,000 parts, more preferably 300 to 5,000 parts, based on 100 parts of the compound and/or polymer (A).

Such a composition for forming an organic film can be applied by spin-coating, and has heat resistance and high filling and planarizing properties because the inventive compound and/or polymer used in a composition for forming an organic film as described above is incorporated.

Further, the inventive composition for forming an organic film may use the organic solvent in which a high-boiling-point solvent having a boiling point of 180° C. or higher is added to the aforementioned solvent having a boiling point of lower than 180° C. (a mixture of a solvent having a boiling point of lower than 180° C. and a solvent having a boiling point of 180° C. or higher). The high-boiling point organic solvent is not particularly limited to hydrocarbons, alcohols, ketones, esters, ethers, chlorinated solvents, and so forth as long as the high-boiling point organic solvent is capable of dissolving the compound and/or polymer used in a composition for forming an organic film. Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl-n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, dibutyl succinate, dihexyl succinate, dimethyl adipate, diethyl adipate, dibutyl adipate, and the like. One of these or a mixture thereof may be used.

The boiling point of the high-boiling-point solvent may be appropriately selected according to the temperature at which the composition for forming an organic film is heated. The boiling point of the high-boiling-point solvent to be added is preferably 180° C. to 300° C., more preferably 200° C. to 300° C. Such a boiling point prevents the evaporation rate at baking (heating) from becoming excessive, which would otherwise occur if the boiling point is too low. Thus, sufficient thermal flowability can be achieved. Meanwhile, with such a boiling point, the boiling point is not too high, so that the high-boiling-point solvent evaporates after baking and does not remain in the film; thus, the boiling point in these ranges does not adversely affect the film physical properties, such as etching resistance.

When the high-boiling-point solvent is used, the contained amount of the high-boiling-point solvent is preferably 1 to 30 parts by mass based on 100 parts by mass of the solvent having a boiling point of lower than 180° C. When the contained amount is within this range, sufficient thermal flowability can be provided, the high-boiling-point solvent does not remain in the film, and film physical properties such as etching resistance are also excellent.

With such a composition for forming an organic film, the above-described composition for forming an organic film is provided with thermal flowability by the addition of the high-boiling-point solvent, so that the composition for forming an organic film also has high filling and planarizing properties.

[Acid Generator]

In the inventive composition for forming an organic film, an acid generator can be added so as to further promote the curing reaction. The acid generator includes a material that generates an acid by thermal decomposition and a material that generates an acid by light irradiation. Any acid generator can be added. Specifically, materials disclosed in paragraphs [0061] to [0085] of JP 2007-199653 A can be added, but the present invention is not limited thereto.

One of the acid generators or a combination of two or more thereof can be used. When an acid generator is added, the added amount is preferably 0.05 to 50 parts, more preferably 0.1 to 10 parts, based on 100 parts of the above-described compound and/or polymer.

[Surfactant]

To the inventive composition for forming an organic film, a surfactant can be added so as to enhance the coating property in spin-coating. As the surfactant, for example, those disclosed in [0142] to [0147] of JP 2009-269953 A can be used. When a surfactant is added, the added amount is preferably 0.01 to 10 parts, more preferably 0.05 to 5 parts, based on 100 parts of the above-described compound and/or polymer.

In the present invention, the composition for forming an organic film preferably further contains at least one of a surfactant and a plasticizer.

[Crosslinking Agent]

Moreover, to the inventive composition for forming an organic film, a crosslinking agent can also be added so as to increase the curability and to further suppress intermixing with an upper layer film. The crosslinking agent is not particularly limited, and known various types of crosslinking agents can be widely used. Examples thereof include methylol or alkoxymethyl-type crosslinking agents of polynuclear phenols, melamine-based crosslinking agents, glycoluril-based crosslinking agents, benzoguanamine-based crosslinking agents, urea-based crosslinking agents, β-hydroxyalkylamide-based crosslinking agents, isocyanurate-based crosslinking agents, aziridine-based crosslinking agents, oxazoline-based crosslinking agents, and epoxy-based crosslinking agents. When a crosslinking agent is added, the added amount is preferably 1 to 100 parts, more preferably 5 to 50 parts based on 100 parts of the compound and/or polymer.

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the β-hydroxyalkylamide-based crosslinking agents includes N,N,N',N'-tetra(2-hydroxyethyl)adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]. Specific examples of the oxazoline-based crosslinking agents include 2,2'-isopropylidene bis(4-benzyl-2-oxazoline), 2,2'-isopropylidene bis(4-phenyl oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

Specific examples of the polynuclear-phenol-based cross-linking agents include compounds shown by the following general formula (7).

(7)

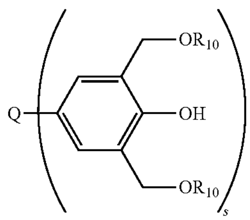

In the formula, Q represents a single bond or a hydrocarbon group with a valency of "s" having 1 to 20 carbon atoms. $R_{10}$ represents a hydrogen atom or an alkyl group having 1 to 20 carbon atoms. "s" represents an integer of 1 to 5.

Q represents a single bond or a hydrocarbon group with a valency of "s" having 1 to 20 carbon atoms. "s" represents an integer of 1 to 5, more preferably 2 or 3. Specific examples of Q include groups obtained by removing "s" hydrogen atoms from methane, ethane, propane, butane, isobutane, pentane, cyclopentane, hexane, cyclohexane, methyl pentane, methyl cyclohexane, dimethyl cyclohexane, trimethyl cyclohexane, benzene, toluene, xylene, ethyl benzene, ethyl isopropylbenzene, diisopropylbenzene, methylnaphthalene, ethyl naphthalene, and eicosane. $R_{10}$ represents a hydrogen atom or an alkyl group having 1 to 20 carbon atoms. Specific examples of the alkyl group having 1 to 20 carbon atoms include a methyl group, an ethyl group, a propyl group, an isopropyl group, a butyl group, an isobutyl group, a pentyl group, an isopentyl group, a hexyl group, an octyl group, an ethylhexyl group, a decyl group, and an eicosanyl group. A hydrogen atom or a methyl group is preferable.

Specific examples of the compound shown by the general formula (7) include the following compounds. In particular, in view of enhancing the curability and film thickness uniformity of the organic film, hexamethoxymethylated compounds of triphenolmethane, triphenolethane, 1,1,1-tris(4-hydroxyphenyl)ethane, and tris(4-hydroxyphenyl)-1-ethyl-4-isopropylbenzene are preferable. $R_{10}$ is as defined above.

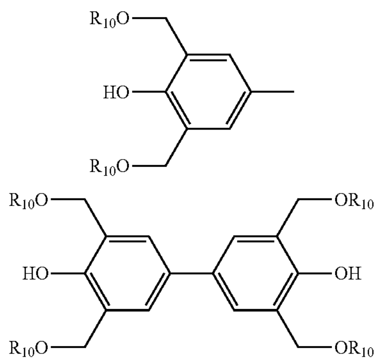

-continued

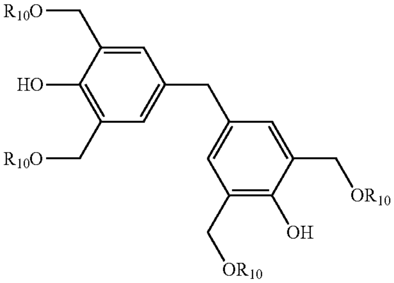

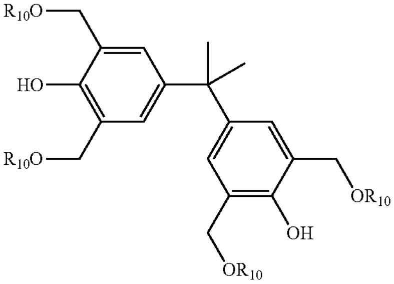

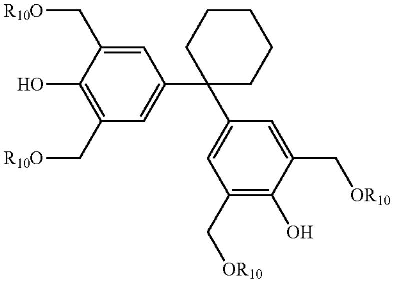

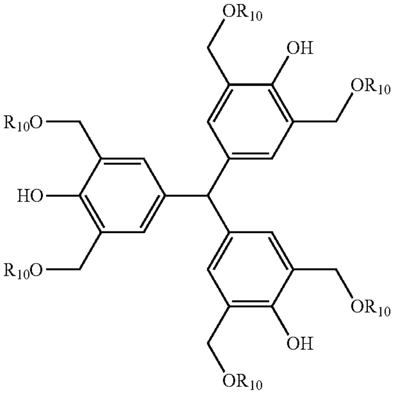

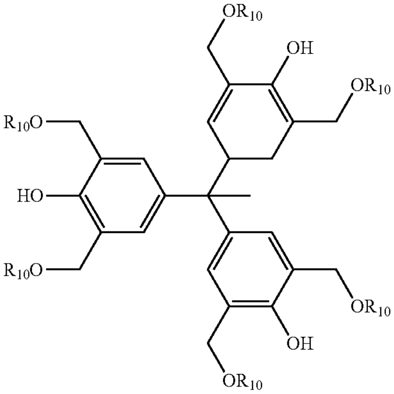

-continued
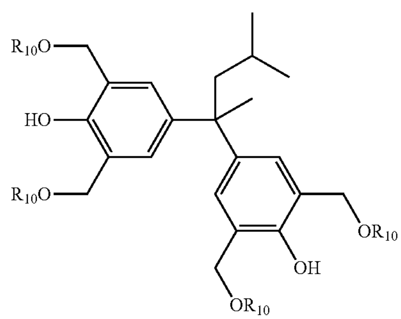
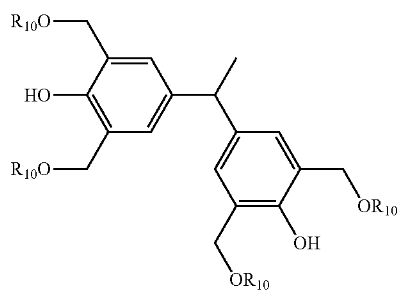
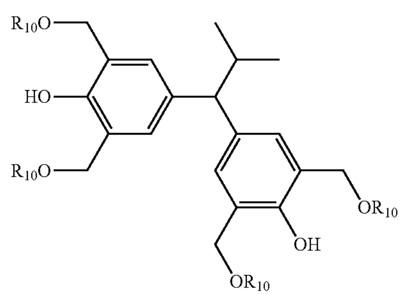
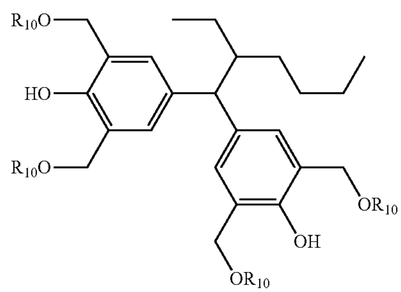
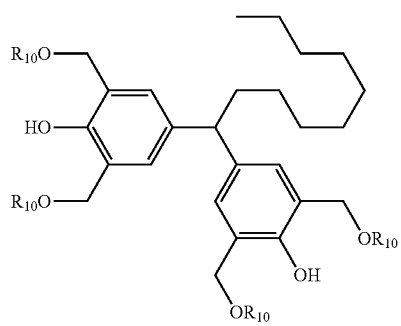
-continued
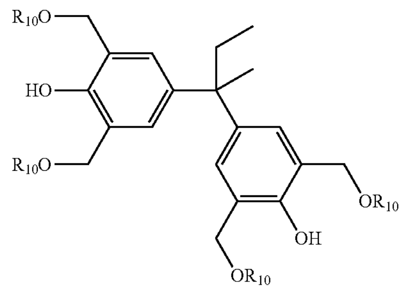
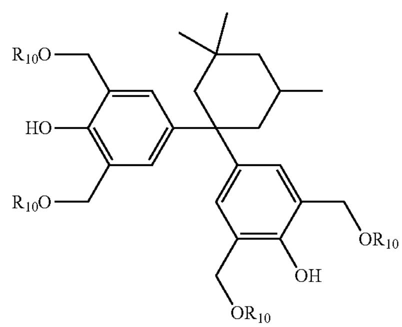
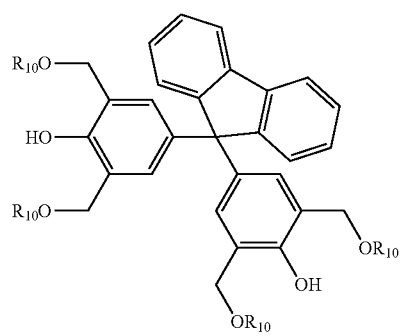
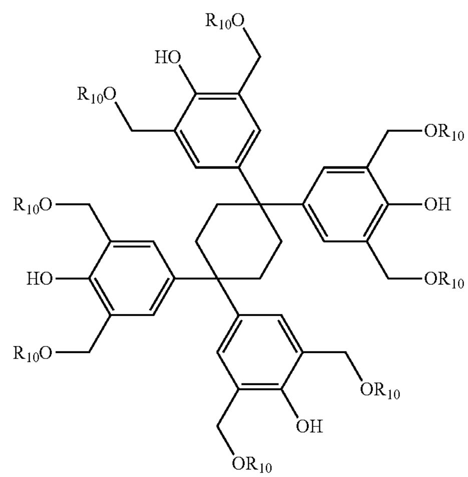

-continued

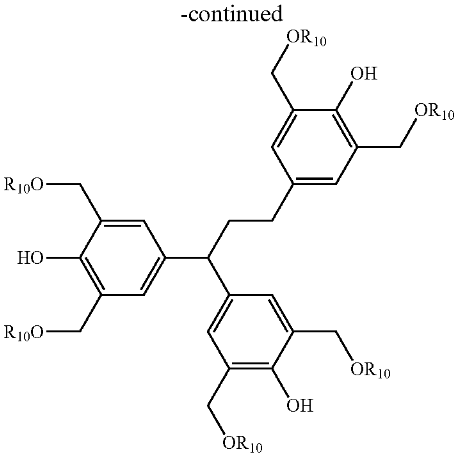

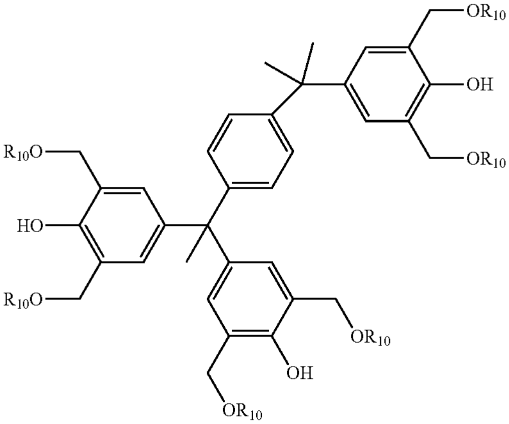

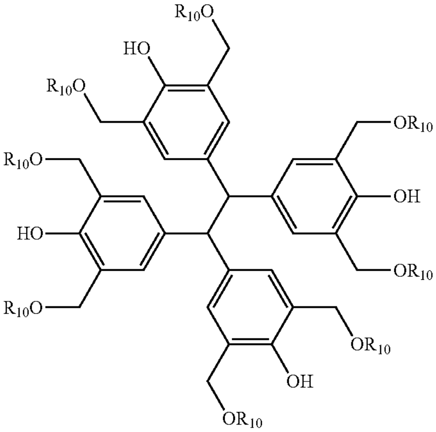

-continued

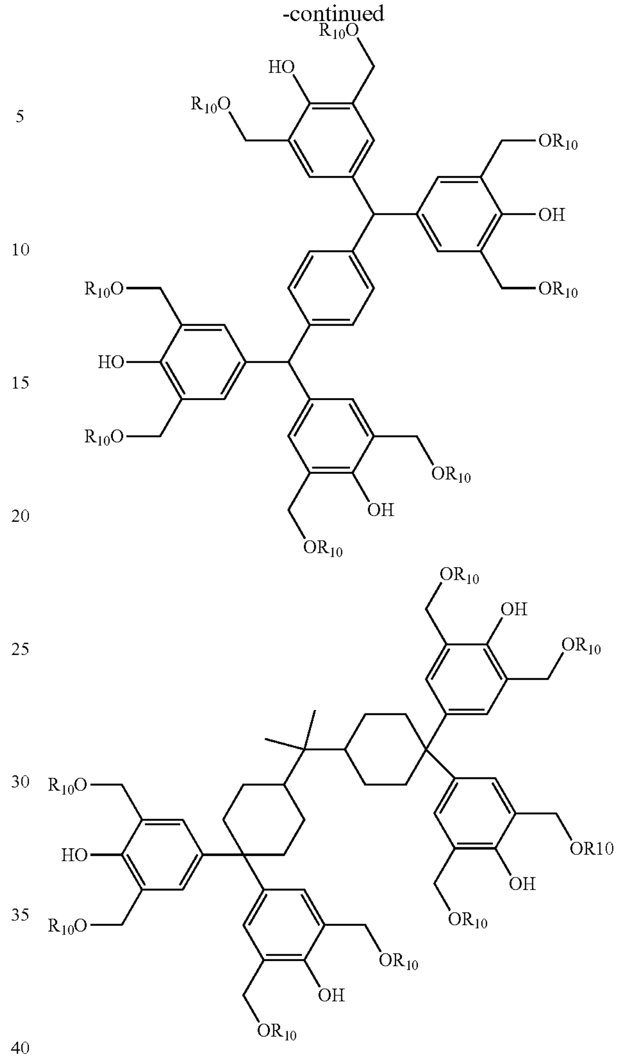

[Plasticizer]

Further, to the inventive composition for forming an organic film, a plasticizer can be added so as to enhance the planarizing and filling properties further. The plasticizer is not particularly limited, and known various types of plasticizers can be widely used. Examples thereof include low-molecular-weight compounds, such as phthalic acid esters, adipic acid esters, phosphoric acid esters, trimellitic acid esters, and citric acid esters; and polymers such as polyethers, polyesters, and polyacetal-based polymers disclosed in JP 2013-253227 A. When a plasticizer is added, the added amount is preferably 1 to 100 parts, more preferably 5 to 30 parts based on 100 parts of the above-described compound and/or polymer.

Furthermore, like the plasticizer, as an additive for providing the inventive composition for forming an organic film with filling and planarizing properties, it is preferable to use, for example, liquid additives having polyethylene glycol or polypropylene glycol structures, or thermo-decomposable polymers having a weight loss ratio between 30° C. and 250° C. of 40 mass % or more and a weight-average molecular weight of 300 to 200,000. The thermo-decomposable polymers preferably contain a repeating unit having an acetal structure shown by the following general formula (DP1) or (DP1a).

(DP1)

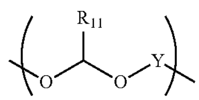

In the formula, $R_{11}$ represents a hydrogen atom or a saturated or unsaturated monovalent organic group having 1 to 30 carbon atoms which may be substituted. Y represents a saturated or unsaturated divalent organic group having 2 to 30 carbon atoms.

(DP1a)

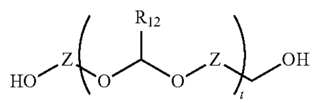

In the formula, $R_{12}$ represents an alkyl group having 1 to 4 carbon atoms. Z represents a saturated or unsaturated divalent hydrocarbon group having 4 to 10 carbon atoms which may have an ether bond. "t" represents an average repeating unit number of 3 to 500.

[Other Components]

The inventive composition for forming an organic film may be further blended with a different compound or polymer. The blend compound or blend polymer mixed with the inventive composition for forming an organic film serves to improve the film-formability with spin-coating and the filling property for a stepped substrate.

Examples of such a material include novolak resins of phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy methylphenol, 2-tert-butyl-5-methylphenol, pyrogallol, thymol, isothymol, 4,4'-(9H-fluorene-9-ylidene)bisphenol, 2,2'dimethyl-4,4'-(9H-fluorene-9-ylidene)bisphenol, 2,2'diallyl-4,4'-(9H-fluorene-9-ylidene)bisphenol, 2,2'difluoro-4,4'-(9H-fluorene-9-ylidene)bisphenol, 2,2'diphenyl-4,4'-(9H-fluorene-9-ylidene)bisphenol, 2,2'dimethoxy-4,4'-(9H-fluorene-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, and 7-methoxy-2-naphthol, dihydroxynaphthalenes such as 1,5-dihydroxynaphthalene, 1,7-dihydroxynaphthalene, and 2,6-dihydroxynaphthalene, methyl 3-hydroxynaphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, limonene, etc.; and polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, poly(meth)acrylate, and copolymers thereof. It is also possible to blend a naphthol dicyclopentadiene copolymer disclosed in JP 2004-205685 A, a fluorene bisphenol novolak resin disclosed in JP 2005-128509 A, an acenaphthylene copolymer disclosed in JP 2005-250434 A, fullerene having a phenol group disclosed in JP 2006-227391 A, a bisphenol compound and a novolak resin thereof disclosed in JP 2006-293298 A, a novolak resin of an adamantane phenol compound disclosed in JP 2006-285095 A, a bisnaphthol compound and a novolak resin thereof disclosed in JP 2010-122656 A, a fullerene resin compound disclosed in JP 2008-158002 A, or the like.

The blended amount of the blend compound or the blend polymer is preferably 0 to 1,000 parts by mass, more preferably 0 to 500 parts by mass based on 100 parts by mass of the inventive composition for forming an organic film.

Note that one kind of the material for forming an organic film of the present invention can be used, or a combination of two or more thereof can be used. The composition for forming an organic film can be used for an organic film material or a planarizing material for manufacturing a semiconductor device.

In addition, the inventive composition for forming an organic film is extremely useful as an organic film material in a multilayer resist process such as a 2-layer resist process, a 3-layer resist process using a silicon-containing middle layer film, or a 4-layer resist process using a silicon-containing inorganic hard mask and an organic antireflective coating.

(Method for Forming Organic Film)

The present invention provides a method for forming an organic film which serves as an organic film in a multilayer resist film used in lithography or a planarizing film for manufacturing a semiconductor by using the above-described composition for forming an organic film.

In the method for forming an organic film by using the inventive composition for forming an organic film, a substrate to be processed is coated with the composition for forming an organic film by a spin-coating method, etc. By employing a method like spin-coating method, favorable filling property can be obtained. After the spin-coating, baking (heating) is performed to evaporate the solvent and to promote the crosslinking reaction, thereby preventing the mixing with a resist upper layer film or a resist middle layer film. The baking is preferably performed at 100° C. or higher to 600° C. or lower for 10 to 600 seconds, more preferably at 200° C. or higher to 500° C. or lower for 10 to 300 seconds. In considering the influences of device damage and wafer deformation, the upper limit of the heating temperature in lithographic wafer process is preferably 600° C. or lower, more preferably 500° C. or lower.

Moreover, in the method for forming an organic film by using the inventive composition for forming an organic film, after a substrate to be processed is coated with the inventive composition for forming an organic film by the spin-coating method or the like as described above, an organic film can be formed by curing the composition for forming an organic film by baking in an atmosphere with an oxygen concentration of 0.1 volume % or more to 21 volume % or less.

The inventive composition for forming an organic film is baked in such an oxygen atmosphere, thereby enabling to obtain a fully cured film. The atmosphere during the baking may be in air. Nevertheless, it is preferable to introduce an inert gas such as $N_2$, Ar, or He to reduce oxygen amount from the viewpoint of preventing oxidation of the organic film. To prevent the oxidation, the oxygen concentration needs to be controlled, and is preferably 1000 ppm or less, more preferably 100 ppm or less (based on volume). Preventing the oxidation of the organic film during baking is preferable because an increase in absorption and a decrease in etching resistance are prevented.

(Patterning Process)

The present invention provides a patterning process according to a 3-layer resist process using the composition for forming an organic film as described above. The patterning process is a method for forming a pattern in a body to be processed, and includes at least the following steps:

forming an organic film by using the inventive composition for forming an organic film on a body to be processed;

forming a silicon-containing resist middle layer film by using a silicon-containing resist middle layer film material on the organic film;

forming a resist upper layer film by using a photoresist composition on the silicon-containing resist middle layer film;

forming a circuit pattern in the resist upper layer film;

transferring the pattern to the silicon-containing resist middle layer film by etching while using the resist upper layer film having the formed pattern as a mask;

transferring the pattern to the organic film by etching while using the silicon-containing resist middle layer film having the transferred pattern as a mask; and further forming the pattern in the body to be processed by etching while using the organic film having the transferred pattern as a mask.

The silicon-containing resist middle layer film in the 3-layer resist process exhibits resistance to etching by an oxygen gas or a hydrogen gas. Thus, when the organic film is dry-etched while using the silicon-containing resist middle layer film as a mask in the 3-layer resist process, the dry etching is preferably performed using an etching gas mainly containing an oxygen gas or a hydrogen gas.

As the silicon-containing resist middle layer film in the 3-layer resist process, a polysiloxane-based middle layer film is also favorably used. The silicon-containing resist middle layer film having an antireflective effect can suppress the reflection. Particularly, for 193-nm light exposure, a material containing many aromatic groups and having high etching selectivity to a substrate is used as an organic film, so that the k-value and thus the substrate reflection are increased. However, the reflection can be suppressed by providing the silicon-containing resist middle layer film with absorption to achieve an appropriate k-value. Thus, the substrate reflection can be reduced to 0.5% or less. As the silicon-containing resist middle layer film having the antireflective effect, a polysiloxane is preferably used, the polysiloxane having anthracene for 248-nm and 157-nm light exposure, or a phenyl group or a light-absorbing group having a silicon-silicon bond for 193-nm light exposure in a pendant structure, and being crosslinked by an acid or heat.

In addition, a 4-layer resist process using an organic antireflective coating is also favorable, and in this case, a semiconductor device circuit pattern can be formed on a substrate by performing at least the following steps:

forming an organic film by using the inventive composition for forming an organic film on a body to be processed;

forming a silicon-containing resist middle layer film by using a silicon-containing resist middle layer film material on the organic film;

forming an organic antireflective coating, bottom antireflective coating (BARC), on the silicon-containing resist middle layer film;

forming a resist upper layer film by using a photoresist composition on the BARC, so that a 4-layered film structure is constructed;

forming a circuit pattern in the resist upper layer film;

transferring the pattern to the BARC and the silicon-containing resist middle layer film by etching while using the resist upper layer film having the formed pattern as a mask;

transferring the pattern to the organic film by etching while using the silicon-containing resist middle layer film having the transferred pattern as a mask; and further forming the pattern in the body to be processed by etching the body to be processed while using the organic film having the transferred pattern as a mask.

In addition, an inorganic hard mask can be formed instead of the silicon-containing resist middle layer film, and in this case, a semiconductor device circuit pattern can be formed in a substrate by performing at least the following steps:

forming an organic film by using the inventive composition for forming an organic film on a body to be processed;

forming an inorganic hard mask selected from a silicon oxide film, a silicon nitride film, and a silicon oxynitride film on the organic film;

forming a resist upper layer film by using a photoresist composition on the inorganic hard mask;

forming a circuit pattern in the resist upper layer film;

etching the inorganic hard mask while using the resist upper layer film having the formed pattern as a mask;

etching the organic film while using the inorganic hard mask having the formed pattern as a mask; and further forming the pattern in the body to be processed by etching the body to be processed while using the organic film having the formed pattern as a mask.

In the case where an inorganic hard mask is formed on the organic film as described above, a silicon oxide film, a silicon nitride film, and a silicon oxynitride film (SiON film) can be formed by a CVD method, an ALD method, or the like. The method for forming the silicon nitride film is disclosed in, for example, JP 2002-334869 A and WO 2004/066377 A1. The film thickness of the inorganic hard mask is preferably 5 to 200 nm, more preferably 10 to 100 nm. As the inorganic hard mask, a SiON film is most preferably used, being effective as an antireflective coating. When the SiON film is formed, the substrate temperature reaches 300 to 500° C. Hence, the organic film needs to withstand the temperature of 300 to 500° C. Since the compositions for forming an organic film used in the present invention have high heat resistance and can withstand high temperatures of 300° C. to 500° C., the combination of the inorganic hard mask formed by a CVD method or an ALD method with the organic film formed by a spin-coating method is possible.

A 4-layer resist process using an organic antireflective coating is also favorable, and in this case, a semiconductor device circuit pattern can be formed in a substrate by performing at least the following steps:

forming an organic film by using the inventive composition for forming an organic film on a body to be processed;

forming an inorganic hard mask selected from a silicon oxide film, a silicon nitride film, and a silicon oxynitride film on the organic film;

forming an organic antireflective coating (BARC) on the inorganic hard mask;

forming a resist upper layer film by using a photoresist composition on the BARC, so that a 4-layered film structure is constructed;

forming a circuit pattern in the resist upper layer film;

etching the BARC and the inorganic hard mask while using the resist upper layer film having the formed pattern as a mask;

etching the organic film while using the inorganic hard mask having the formed pattern as a mask; and further forming the pattern in the body to be processed by etching the body to be processed while using the organic film having the formed pattern as a mask.

The photoresist film may be formed on the inorganic hard mask as a resist upper layer film as described above, or alternatively, it is also possible to form an organic antireflective coating (BARC) on the inorganic hard mask by spin-coating, and then form a photoresist film thereon. In particular, when a SiON film is used as the inorganic hard mask, two antireflective coatings including the SiON film and the BARC make it possible to suppress the reflection even in liquid immersion exposure at a high NA exceeding 1.0. Another advantage of the BARC formation is having an effect of reducing trailing of the photoresist pattern immediately above the SiON film.

The resist upper layer film in the multilayer resist process may be a positive type or a negative type, and any generally-used photoresist composition can be employed. After spin-coating of the photoresist composition, pre-baking is performed, preferably at 60 to 180° C. for 10 to 300 seconds. Then, light exposure, post-exposure baking (PEB), and development are performed according to conventional methods to obtain the resist pattern. Note that the thickness of the resist upper layer film is not particularly limited, but is preferably 30 to 500 nm, and 50 to 400 nm is particularly preferable.

In addition, examples of exposure light include a high-energy beam with a wavelength of 300 nm or less, specifically, excimer laser of 248 nm, 193 nm, and 157 nm, soft X-ray of 3 to 20 nm, electron beam, X-ray, and the like.

The pattern in the resist upper layer film is preferably formed by a lithography using light with a wavelength of 10 nm or more to 300 nm or less, a direct drawing with electron beam, nanoimprinting, or a combination thereof.

Furthermore, the development method in the patterning processes is preferably alkali development or development with an organic solvent.

Next, etching is performed while using the obtained resist pattern as a mask. In the 3-layer resist process, the silicon-containing resist middle layer film and the inorganic hard mask are etched using a fluorocarbon-based gas while using the upper layer resist pattern as a mask. Thereby, a silicon-containing resist middle layer film pattern and an inorganic hard mask pattern are formed.

Next, the organic film is etched while using the obtained silicon-containing resist middle layer film pattern and inorganic hard mask pattern as masks.

Subsequently, the body to be processed can be etched according to a conventional method. For example, the body to be processed made of $SiO_2$, SiN, or silica-based low-dielectric insulating film is etched mainly with a fluorocarbon-based gas; and p-Si, Al, or W is etched mainly with a chlorine- or bromine-based gas. When the substrate is processed by etching with a fluorocarbon-based gas, the silicon-containing resist middle layer film pattern in the 3-layer resist process is removed when the substrate is processed. When the substrate is etched with a chlorine- or bromine-based gas, the silicon-containing resist middle layer film pattern needs to be removed by additional dry etching with a fluorocarbon-based gas after the substrate processing.

An organic film obtained from the inventive composition for forming an organic film has a characteristic of being excellent in etching resistance when etching these bodies to be processed.

Note that the body to be processed (substrate to be processed) is not particularly limited, and examples include: substrates made of Si, α-Si, p-Si, $SiO_2$, SiN, SiON, W, TiN, Al, or the like; the substrate coated with a layer to be processed; etc. Examples of the layer to be processed include: various Low-k films made of Si, $SiO_2$, SiON, SiN, p-Si, α-Si, W, W—Si, Al, Cu, Al—Si, or the like; and stopper films thereof. Generally, the layer can be formed to have a thickness of 50 to 10,000 nm, in particular, 100 to 5,000 nm. Note that when the layer to be processed is formed, the substrate and the layer to be processed are formed from different materials.

As the body to be processed, it is preferable to use a semiconductor device substrate or the semiconductor device substrate coated with any of a metal film, a metal carbide film, a metal oxide film, a metal nitride film, a metal oxycarbide film, or a metal oxynitride film. More specifically, examples of the substrate which may be used include, but are not particularly limited to: substrates made of Si, α-Si, p-Si, $SiO_2$, SiN, SiON, W, TiN, Al, or the like; and these substrates coated with the above-described metal film or the like as a layer to be processed.

Examples of the layer to be processed which may be used include various Low-k films made of Si, $SiO_2$, SiON, SiN, p-Si, α-Si, W, W—Si, Al, Cu, Al—Si, or the like, and stopper films thereof. The layer can be formed to have a thickness of generally 50 to 10,000 nm, particularly 100 to 5,000 nm. Note that when the layer to be processed is formed, the substrate and the layer to be processed are formed from different materials.

Note that the metal constituting the body to be processed is preferably silicon, titanium, tungsten, hafnium, zirconium, chromium, germanium, copper, silver, gold, aluminum, indium, gallium, arsenic, palladium, iron, tantalum, iridium, cobalt, manganese, molybdenum, ruthenium, or an alloy thereof.

Furthermore, as the body to be processed, a body to be processed having a structure or a step with a height of 30 nm or more is preferably used.

Hereinbelow, an example of the 3-layer resist process will be specifically described with reference to FIG. 1. As shown in FIG. 1 (A), in the 3-layer resist process, an organic film 3 is formed by using the inventive composition for forming an organic film on a layer 2 to be processed that has been stacked on a substrate 1. Then, a silicon-containing resist middle layer film 4 is formed, and a resist upper layer film 5 is formed thereon.

Next, as shown in FIG. 1 (B), a predetermined portion 6 of the resist upper layer film 5 is exposed to light, followed by PEB and development to form a resist pattern **5*a* (FIG. 1 (C)). While using the obtained resist pattern 5*a* as a mask, the silicon-containing resist middle layer film 4 is etched with a CF-based gas. Thereby, a silicon-containing resist middle layer film pattern 4*a* is formed (FIG. 1 (D)). After the resist pattern 5*a* is removed, the organic film 3 is etched with oxygen plasma while using the obtained silicon-containing resist middle layer film pattern 4*a* as a mask. Thereby, an organic film pattern 3*a* is formed (FIG. 1 (E)). Further, after the silicon-containing resist middle layer film pattern 4*a* is removed, the layer 2 to be processed is etched while using the organic film pattern 3***a* as a mask. Thus, a pattern 2*a* is formed (FIG. 1 (F)).

When an inorganic hard mask is used, the silicon-containing resist middle layer film 4 is the inorganic hard mask, and when a BARC is formed, the BARC layer is disposed between the silicon-containing resist middle layer film 4 and the resist upper layer film 5. The etching of the BARC may be performed continuously before the etching of the silicon-containing resist middle layer film 4. Alternatively, after the BARC is etched alone, the etching apparatus is changed, for example, and then the etching of the silicon-containing resist middle layer film 4 may be performed.

As described above, the inventive patterning processes make it possible to precisely form a fine pattern in a substrate to be processed in the multilayer resist processes.

Particularly, in the present invention, an organic solvent and, as a material for forming an organic film, a composition for forming an organic film containing (i) a compound shown by the general formula (1) and/or (2) and (ii) a polymer having a repeating unit shown by the general formula (4) and/or (5) are used. Therefore, a fine pattern can be formed in a body to be processed with even higher precision in a multilayer resist process.

EXAMPLE

Hereinafter, the present invention will be more specifically described with reference to Synthesis Examples, Examples, and Comparative Examples. However, the present invention is not limited thereto. Note that, with respect to molecular weight and dispersity, weight-average molecular weight (Mw) and number-average molecular weight (Mn) were measured by gel permeation chromatography (GPC) using tetrahydrofuran as an eluent in terms of polystyrene, and dispersity (Mw/Mn) was calculated therefrom.

Synthesis Example: Synthesis of Compounds and Polymers Used in Compositions for Forming Organic Film Compounds or polymers (A1) to (A13) used in compositions for forming an organic film and polymers (R1) to (R3) used in the Comparative Examples were synthesized using compounds (B1) to (B10) as aromatic compounds shown below, compounds (C1) to (C4) as an indole-2,3-dione and its derivatives, and compounds (D1) to (D3) as an aldehyde or a ketone. Note that as (D1), a 37% aqueous solution was used.

Aromatic Compounds:

(B1)

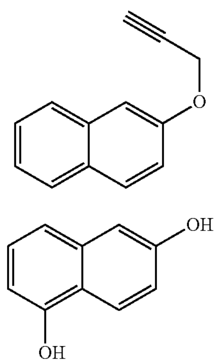

(B2)

-continued (B3)

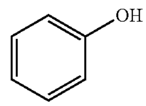

(B4)

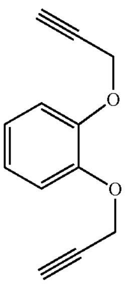

(B5)

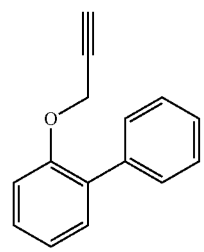

(B6)

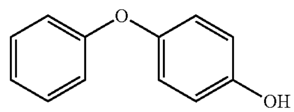

(B7)

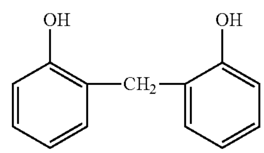

(B8)

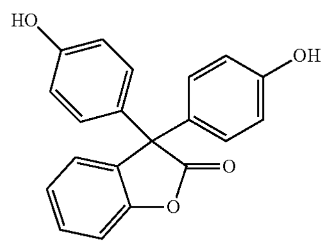

(B9)

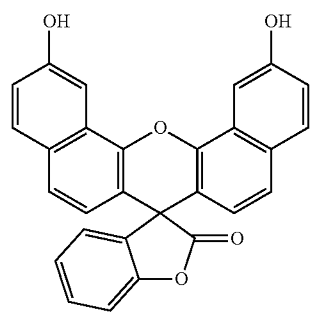

-continued (B10)

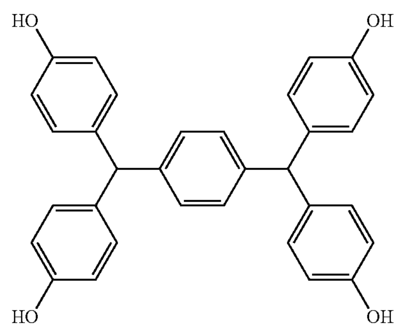

Indole-2,3-diones:

(C1)

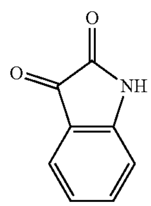

(C2)

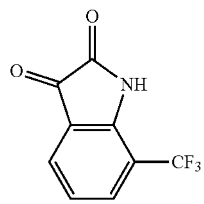

(C3)

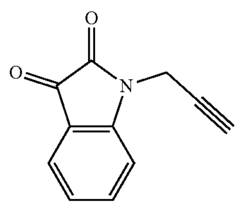

(C4))

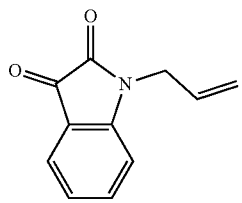

Aldehyde or Ketone:

(D1)

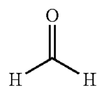

-continued (D2)

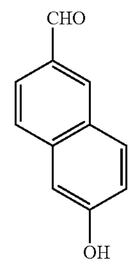

(D3)

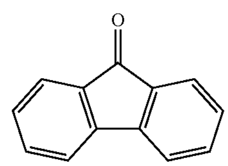

Synthesis Example 1

Synthesis of Compound (A1)

(A1)

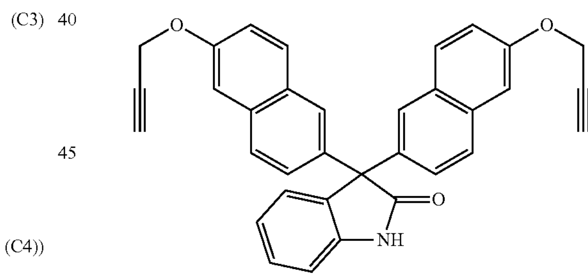

Under a nitrogen atmosphere, 81.7 g of the compound (B1), 30.0 g of the compound (C1), and 450 g of methylene chloride were added to form a homogeneous dispersion at room temperature. Subsequently, 91.8 g of trifluoromethanesulfonic acid was slowly added dropwise, and the reaction was allowed to proceed at room temperature for 8 hours. After completion of the reaction, 1000 ml of MIBK (methyl isobutyl ketone) was added, the resultant was washed six times with 300 ml of pure water, and the organic layer was evaporated under reduced pressure to dry up. To the residue, 240 g of MIBK was added to form a homogeneous solution. Thereafter, a crystal was precipitated in 1200 g of IPE (diisopropyl ether). The precipitated crystal was separated by filtration, washed twice with 400 g of IPE, and collected. The collected crystal was vacuum dried at 70° C. to obtain compound (A1).

When the weight-average molecular weight (Mw) and dispersity (Mw/Mn) were measured by GPC, the following results were obtained.

(A1): Mw=520, Mw/Mn=1.02

Synthesis Example 2

Synthesis of Compound (A2)

(A2)

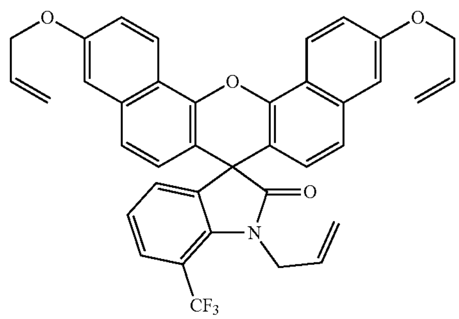

Under a nitrogen atmosphere, 49.1 g of the compound (B2), 30.0 g of the compound (C2), and 240 g of methylene chloride were added to form a homogeneous dispersion at room temperature. Subsequently, 69.6 g of trifluoromethanesulfonic acid was slowly added dropwise, and the reaction was allowed to proceed at room temperature for 8 hours. After completion of the reaction, 1000 ml of MIBK (methyl isobutyl ketone) was added, the resultant was washed six times with 300 ml of pure water, and the organic layer was evaporated under reduced pressure to dry up. To the collected residue, 240 g of DMF (dimethylformamide) and 84.8 g of potassium carbonate were added, and under a nitrogen atmosphere, a homogeneous dispersion was formed at an inner temperature of 50° C. 64.9 g of allyl bromide was added slowly, and the reaction was allowed to proceed at an inner temperature of 50° C. for 16 hours. After completion of the reaction, 600 ml of MIBK was added, the resultant was washed six times with 600 ml of pure water, and the organic layer was evaporated under reduced pressure to dry up. To the residue, 250 g of MIBK was added to form a homogeneous solution. Thereafter, a crystal was precipitated in 1000 g of hexane. The precipitated crystal was separated by filtration, washed twice with 200 g of hexane, and collected. The collected crystal was vacuum dried at 70° C. to obtain compound (A2).

When the weight-average molecular weight (Mw) and dispersity (Mw/Mn) were measured by GPC, the following results were obtained.

(A2): Mw=630, Mw/Mn=1.04

Synthesis Example 3

Synthesis of Compound (A3)

(A3)

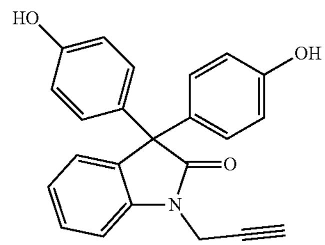

Under a nitrogen atmosphere, 33.5 g of the compound (B3), 30.0 g of the compound (C3), 250 g of methylene chloride, and 46.7 g of methanesulfonic acid were added to form a homogeneous dispersion at room temperature. Subsequently, 1.7 g of 3-mercaptopropionic acid was added, and the reaction was allowed to proceed at room temperature for 8 hours. After completion of the reaction, 600 ml of MIBK (methyl isobutyl ketone) was added, the resultant was washed six times with 200 ml of pure water, and the organic layer was evaporated under reduced pressure to dry up. To the residue, 180 g of MIBK was added to form a homogeneous solution. Thereafter, a crystal was precipitated in 800 g of hexane. The precipitated crystal was separated by filtration, washed twice with 200 g of hexane, and collected. The collected crystal was vacuum dried at 70° C. to obtain compound (A3).

When the weight-average molecular weight (Mw) and dispersity (Mw/Mn) were measured by GPC, the following results were obtained.

(A3): Mw=340, Mw/Mn=1.01

Synthesis Example 4

Synthesis of Compound (A4)

(A4)

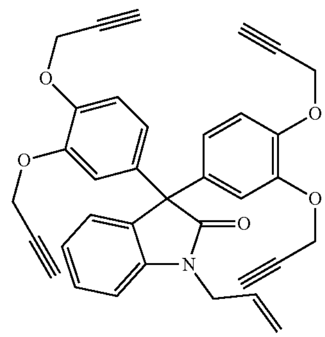

Under a nitrogen atmosphere, 65.7 g of the compound (B4), 30.0 g of the compound (C4), 400 g of methylene chloride, and 46.2 g of methanesulfonic acid were added to form a homogeneous dispersion at room temperature. Subsequently, 1.7 g of 3-mercaptopropionic acid was added, and the reaction was allowed to proceed at room temperature for 8 hours. After completion of the reaction, 800 ml of MIBK (methyl isobutyl ketone) was added, the resultant was washed six times with 300 ml of pure water, and the organic layer was evaporated under reduced pressure to dry up. To the residue, 250 g of MIBK was added to form a homogeneous solution. Thereafter, a crystal was precipitated in 1000 g of hexane. The precipitated crystal was separated by filtration, washed twice with 300 g of hexane, and collected. The collected crystal was vacuum dried at 70° C. to obtain compound (A4).

When the weight-average molecular weight (Mw) and dispersity (Mw/Mn) were measured by GPC, the following results were obtained.

(A4): Mw=590, Mw/Mn=1.03

Synthesis Example 5

Synthesis of compound (A5)

(A5)

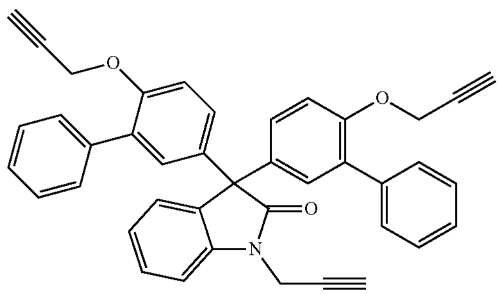

Under a nitrogen atmosphere, 67.5 g of the compound (B5), 30.0 g of the compound (C3), 400 g of methylene chloride, and 46.7 g of methanesulfonic acid were added to form a homogeneous dispersion at room temperature. Subsequently, 1.7 g of 3-mercaptopropionic acid was added, and the reaction was allowed to proceed at room temperature for 8 hours. After completion of the reaction, 800 ml of MIBK (methyl isobutyl ketone) was added, the resultant was washed six times with 300 ml of pure water, and the organic layer was evaporated under reduced pressure to dry up. To the residue, 250 g of MIBK was added to form a homogeneous solution. Thereafter, a crystal was precipitated in 1000 g of hexane. The precipitated crystal was separated by filtration, washed twice with 300 g of hexane, and collected. The collected crystal was vacuum dried at 70° C. to obtain compound (A5).

When the weight-average molecular weight (Mw) and dispersity (Mw/Mn) were measured by GPC, the following results were obtained.

(A5): Mw=590, Mw/Mn=1.02

Synthesis Example 6

Synthesis of Compound (A6)

(A6)

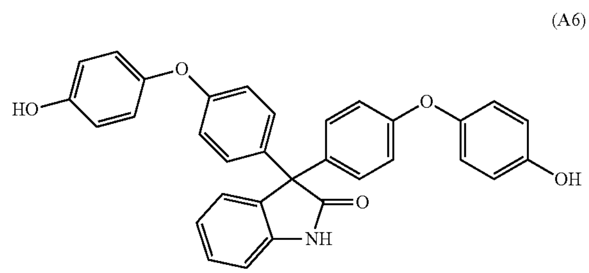 [SMILES: O=C1Nc2ccccc2C1(c1ccc(Oc2ccc(O)cc2)cc1)c1ccc(Oc2ccc(O)cc2)cc1]

Under a nitrogen atmosphere, 226.5 g of the compound (B6), 30.0 g of the compound (C1), 1000 g of methylene chloride, and 58.8 g of methanesulfonic acid were added to form a homogeneous dispersion at room temperature. Subsequently, 2.2 g of 3-mercaptopropionic acid was added, and the reaction was allowed to proceed at room temperature for 8 hours. After completion of the reaction, 300 g of pure water and 1000 ml of toluene were added, and the methylene chloride used in the reaction was distilled off under normal pressure. After that, the aqueous layer was removed, the resultant was washed five times with 600 g of a 3% aqueous solution of sodium hydroxide, twice with 300 g of pure water, twice with 300 g of a 1% aqueous solution of nitric acid, and five times with 300 g of pure water in this order, and the organic layer was evaporated under reduced pressure to dry up. To the residue, 250 g of MIBK was added to form a homogeneous solution. Thereafter, a crystal was precipitated in 1000 g of hexane. The precipitated crystal was separated by filtration, washed twice with 300 g of hexane, and collected. The collected crystal was vacuum dried at 70° C. to obtain compound (A6).

When the weight-average molecular weight (Mw) and dispersity (Mw/Mn) were measured by GPC, the following results were obtained.

(A6): Mw=520, Mw/Mn=1.04

Synthesis Example 7

Synthesis of Compound (A7)

(A7)

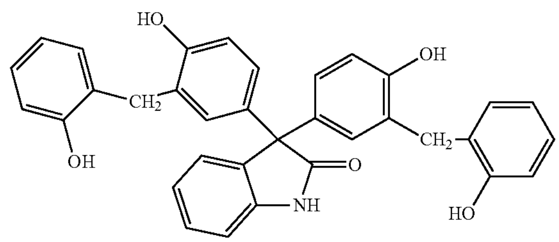

Under a nitrogen atmosphere, 245.0 g of the compound (B7), 30.0 g of the compound (C1), 1000 g of methylene chloride, and 58.8 g of methanesulfonic acid were added to form a homogeneous dispersion at room temperature. Subsequently, 2.2 g of 3-mercaptopropionic acid was added, and the reaction was allowed to proceed at room temperature for 8 hours. After completion of the reaction, 300 g of pure water and 1000 ml of toluene were added, and the methylene chloride used in the reaction was distilled off under normal pressure. After that, the separated aqueous layer was removed, the resultant was washed five times with 600 g of a 3% aqueous solution of sodium hydroxide, twice with 300 g of pure water, twice with 300 g of a 1% aqueous solution of nitric acid, and five times with 300 g of pure water in this order, and the organic layer was evaporated under reduced pressure to dry up. To the residue, 250 g of MIRK was added to form a homogeneous solution. Thereafter, a crystal was precipitated in 1000 g of hexane. The precipitated crystal was separated by filtration, washed twice with 300 g of hexane, and collected. The collected crystal was vacuum dried at 70° C. to obtain compound (A7).

When the weight-average molecular weight (Mw) and dispersity (Mw/Mn) were measured by GPC, the following results were obtained.

(A7): Mw=550, Mw/Mn=1.05

Synthesis Example 8

Synthesis of Compound (A8)

(A8)

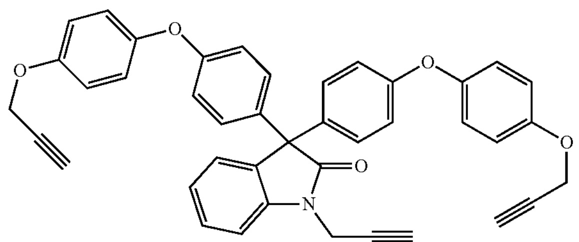

Under a nitrogen atmosphere, 20.0 g of the compound (A6), 33.0 g of potassium carbonate, and 120 g of DMF were added to form a homogeneous dispersion at an inner temperature of 50° C. 23.8 g of propargyl bromide was added slowly, and the reaction was allowed to proceed at an inner temperature of 50° C. for 16 hours. After completion of the reaction, 200 ml of MIBK was added, the resultant was washed six times with 100 ml of pure water, and the organic layer was evaporated under reduced pressure to dry up. To the residue, 80 g of MIBK was added to form a homogeneous solution. Thereafter, a crystal was precipitated in 400 g of MeOH (methanol). The precipitated crystal was separated by filtration, washed twice with 200 g of MeOH, and collected. The collected crystal was vacuum dried at 70° C. to obtain compound (A8).

When the weight-average molecular weight (Mw) and dispersity (Mw/Mn) were measured by GPC, the following results were obtained.

(A8): Mw=650, Mw/Mn=1.04

Synthesis Example 9

Synthesis of Compound (A9)

(A9)

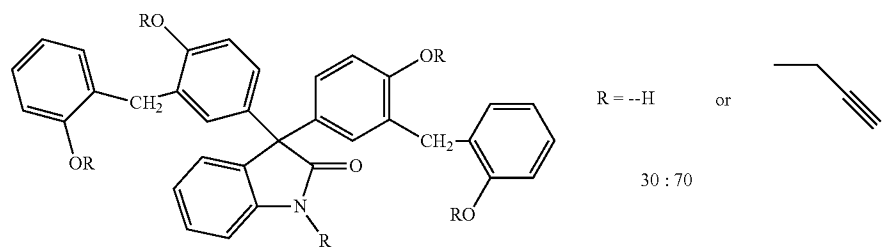

Under a nitrogen atmosphere, 10.0 g of the compound (A7), 10.4 g of potassium carbonate, and 60 g of DMF were added to form a homogeneous dispersion at an inner temperature of 50° C. 4.7 g of propargyl bromide was added slowly, and the reaction was allowed to proceed at an inner temperature of 50° C. for 16 hours. After completion of the reaction, 100 ml of MIBK was added, the resultant was washed six times with 50 ml of pure water, and the organic layer was evaporated under reduced pressure to dry up. To the residue, 40 g of MIBK was added to form a homogeneous solution. Thereafter, a crystal was precipitated in 200 g of hexane. The precipitated crystal was separated by filtration, washed twice with 100 g of hexane, and collected. The collected crystal was vacuum dried at 70° C. to obtain compound (A9).

When the weight-average molecular weight (Mw) and dispersity (Mw/Mn) were measured by GPC, the following results were obtained.

(A9): Mw=670, Mw/Mn=1.07

Synthesis Example 10

Synthesis of Polymer (A10)

(A10)

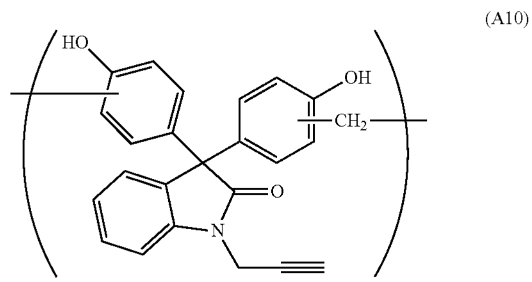

Under a nitrogen atmosphere, 20.0 g of the compound (A3), 2.7 g of the compound (D1), and 50 g of 1,2-dichloroethane were added to form a homogeneous solution at an inner temperature of 50° C. 2.0 g of methanesulfonic acid was added slowly, and the reaction was allowed to proceed at an inner temperature of 50° C. for 8 hours. After completion of the reaction, the resulting product was cooled to room temperature, 200 ml of MIBK was added, the resultant was washed six times with 50 ml of pure water, and the organic layer was evaporated under reduced pressure to dry up. To the residue, 60 g of THF was added to form a homogeneous solution. Thereafter, a crystal was precipitated in 300 g of hexane. The precipitated crystal was separated by filtration, washed twice with 100 g of hexane, and collected. The collected crystal was vacuum dried at 70° C. to obtain polymer (A10).

When the weight-average molecular weight (Mw) and dispersity (Mw/Mn) were measured by GPC, the following results were obtained.

(A10): Mw=3300, Mw/Mn=1.82

Synthesis Example 11

Synthesis of Polymer (A11)

(A11)

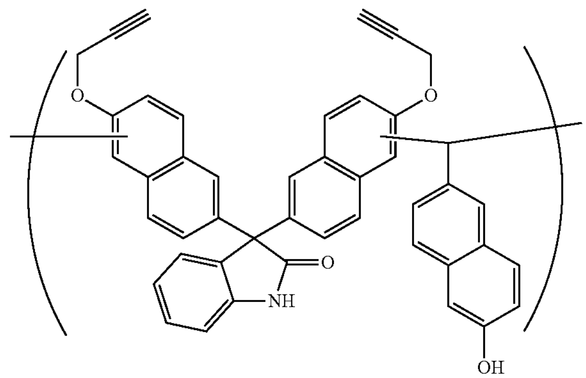

Under a nitrogen atmosphere, 20.0 g of the compound (A1), 4.2 g of the compound (D2), and 100 g of 1,2-dichloroethane were added to form a homogeneous solution at an inner temperature of 50° C. 2.0 g of methanesulfonic acid was added slowly, and the reaction was allowed to proceed at an inner temperature of 50° C. for 8 hours. After completion of the reaction, the resulting product was cooled to room temperature, 200 ml of MIBK was added, the resultant was washed six times with 50 ml of pure water, and the organic layer was evaporated under reduced pressure to dry up. To the residue, 70 g of THF was added to form a homogeneous solution. Thereafter, a crystal was precipitated in 350 g of hexane. The precipitated crystal was separated by filtration, washed twice with 100 g of hexane, and collected. The collected crystal was vacuum dried at 70° C. to obtain polymer (A11).

When the weight-average molecular weight (Mw) and dispersity (Mw/Mn) were measured by GPC, the following results were obtained.

(A11): Mw=2900, Mw/Mn=2.12

Synthesis Example 12

Synthesis of Polymer (A12)

(A12)

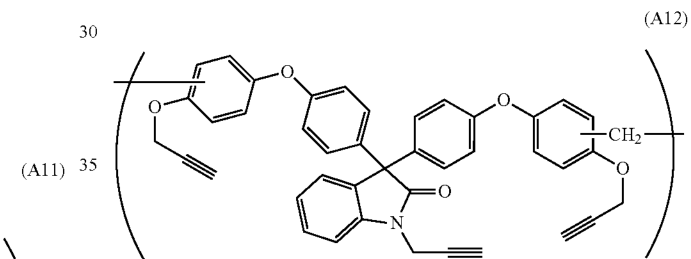

Under a nitrogen atmosphere, 10.0 g of the compound (A8), 0.7 g of the compound (D1), and 50 g of 1,2-dichloroethane were added to form a homogeneous solution at an inner temperature of 50° C. 1.0 g of methanesulfonic acid was added slowly, and the reaction was allowed to proceed at an inner temperature of 50° C. for 8 hours. After completion of the reaction, the resulting product was cooled to room temperature, 100 ml of MIBK was added, the resultant was washed six times with 30 ml of pure water, and the organic layer was evaporated under reduced pressure to dry up. To the residue, 30 g of THF was added to form a homogeneous solution. Thereafter, a crystal was precipitated in 100 g of MeOH. The precipitated crystal was separated by filtration, washed twice with 50 g of MeOH, and collected. The collected crystal was vacuum dried at 70° C. to obtain polymer (A12).

When the weight-average molecular weight (Mw) and dispersity (Mw/Mn) were measured by GPC, the following results were obtained.

(A12): Mw=2800, Mw/Mn=1.65

Synthesis Example 13

Synthesis of Polymer (A13)

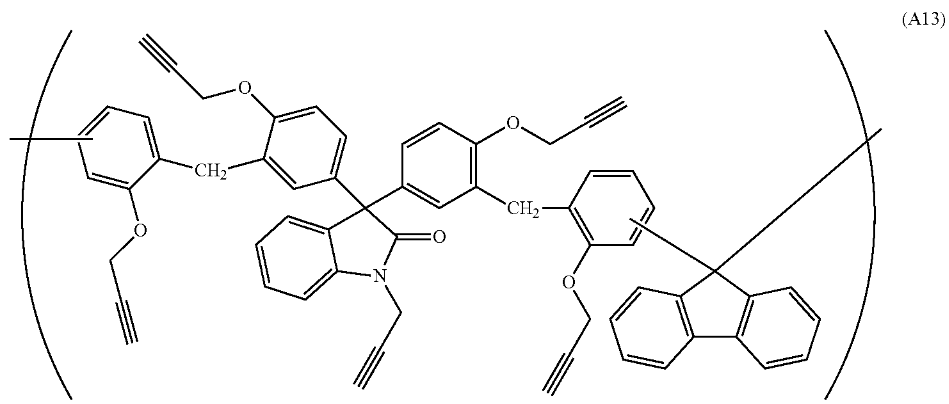

(A13)

Under a nitrogen atmosphere, 20.0 g of the compound (A7), 3.4 g of the compound (D3), and 100 g of 1,2-dichloroethane were added to form a homogeneous solution at an inner temperature of 50° C. 7.2 g of methanesulfonic acid and 0.8 g of 3-mercaptopropionic acid mixed beforehand was added slowly, and the reaction was allowed to proceed at an inner temperature of 50° C. for 12 hours. After completion of the reaction, the resulting product was cooled to room temperature, 300 ml of MTBK was added, the resultant was washed six times with 100 ml of pure water, and the organic layer was evaporated under reduced pressure to dry up. To the collected residue, 100 g of DMF and 36.5 g of potassium carbonate were added, and under a nitrogen atmosphere, a homogeneous dispersion was formed at an inner temperature of 50° C. 27.0 g of propargyl bromide was added slowly, and the reaction was allowed to proceed at an inner temperature of 50° C. for 16 hours. After completion of the reaction, 300 ml of MIBK was added, the resultant was washed six times with 200 ml of pure water, and the organic layer was evaporated under reduced pressure to dry up. To the residue, 80 g of MIBK was added to form a homogeneous solution. Thereafter, a crystal was precipitated in 400 g of MeOH. The precipitated crystal was separated by filtration, washed twice with 100 g of MeOH, and collected. The collected crystal was vacuum dried at 70° C. to obtain polymer (A13).

When the weight-average molecular weight (Mw) and dispersity (Mw/Mn) were measured by GPC, the following results were obtained.

(A13): Mw=3000, Mw/Mn=1.56

Synthesis Example 14

Synthesis of Polymer (R1)

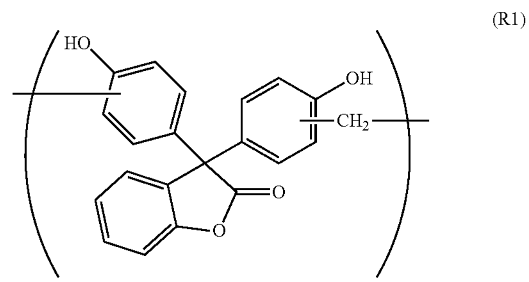

(R1)

Under a nitrogen atmosphere, 31.8 g of the compound (B8), 4.9 g of the compound (D1), 5.0 g of oxalic acid, and 50 g of dioxane were added, and the reaction was allowed to proceed at an inner temperature of 100° C. for 24 hours. After completion of the reaction, the resulting product was cooled to room temperature, 500 ml of MIBK was added, and the resultant was washed six times with 100 ml of pure water. The organic layer was collected, and at an inner temperature of 150° C., the pressure was reduced to 2 mmHg to remove the water and solvent under reduced pressure. Thus, polymer (R1) was obtained.

When the weight-average molecular weight (Mw) and dispersity (Mw/Mn) were measured by GPC, the following results were obtained.

(R1): Mw=3200, Mw/Mn=4.88

Synthesis Example 15

Synthesis of Polymer (R2)

(R2)

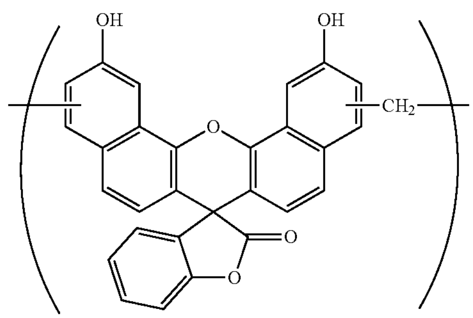

Under a nitrogen atmosphere, 42.3 g of the compound (B9), 5.7 g of the compound (D1), 5.0 g of oxalic acid, and 60 g of dioxane were added, and the reaction was allowed to proceed at an inner temperature of 100° C. for 24 hours. After completion of the reaction, the resulting product was cooled to room temperature, 500 ml of MIBK was added, and the resultant was washed six times with 100 ml of pure water. The organic layer was collected, and at an inner temperature of 150° C., the pressure was reduced to 2 mmHg to remove the water and solvent under reduced pressure. Thus, polymer (R2) was obtained.

When the weight-average molecular weight (Mw) and dispersity (Mw/Mn) were measured by GPC, the following results were obtained.

(R2): Mw=2600, Mw/Mn=3.55

Synthesis Example 16

Synthesis of Polymer (R3)

(R3)

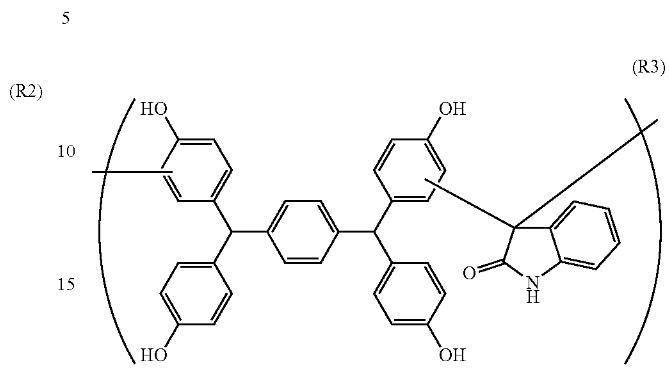

Under a nitrogen atmosphere, 3.1 g of indole-2,3-dione (C1), 10.0 g of the compound (B10), 3.0 g of methanesulfonic acid, 16.1 g of propylene glycol monomethyl ether, and 3.4 g of 3-mercaptopropionic acid were added, heated to 140° C., and the reaction was allowed to proceed under reflux for 4 hours. After completion of the reaction, the reaction solution was added dropwise to 200 g of methanol/pure water=1/1 (mass ratio), and a crystal was precipitated. The precipitated crystal was separated by filtration, washed twice with 100 g of pure water, and collected. The collected crystal was vacuum dried at 60° C. to obtain polymer (R3).

When the weight-average molecular weight (Mw) and dispersity (Mw/Mn) were measured by GPC, the following results were obtained.

(R3): Mw=8500, Mw/Mn=2.30

A list of the results for the Mw and Mw/Mn of the compounds and polymers (A1) to (A13) used in the Examples and the polymers (R1) to (R3) used in the Comparative Examples are shown in Tables 1 to 3.

TABLE 1

| Synthesis Example | Compound or polymer | Mw | Mw/Mn |
| --- | --- | --- | --- |
| 1 | 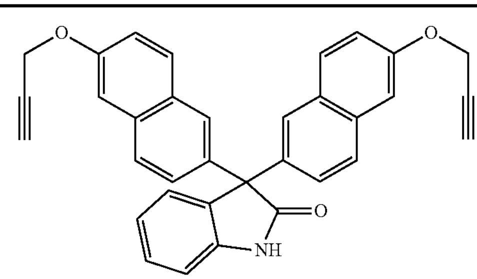 (A1) | 520 | 1.02 |

TABLE 1-continued
| Synthesis Example | Compound or polymer | Mw | Mw/Mn |
|---|---|---|---|
| 2 | 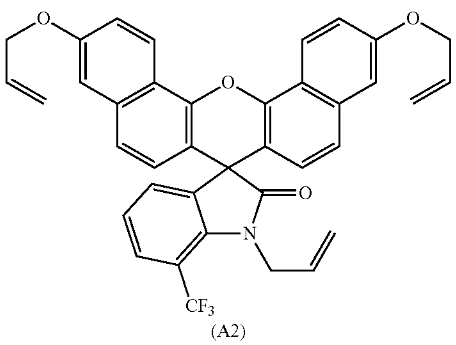 (A2) | 630 | 1.04 |
| 3 | 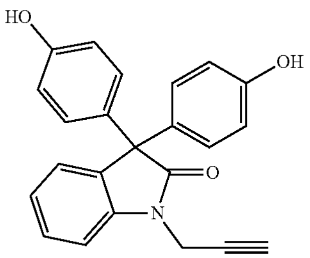 (A3) | 340 | 1.01 |
| 4 | 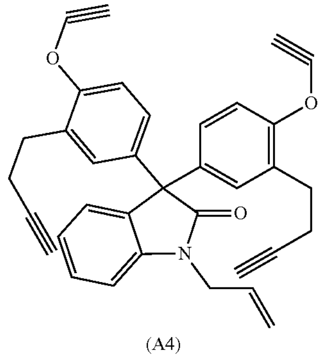 (A4) | 590 | 1.03 |
| 5 | 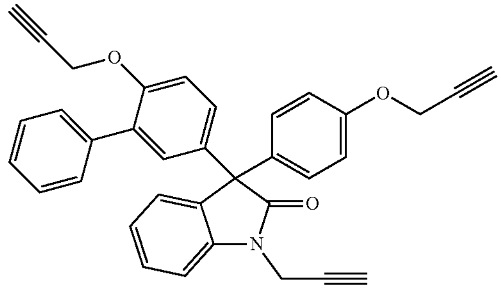 (A5) | 590 | 1. 02 |
| 6 | 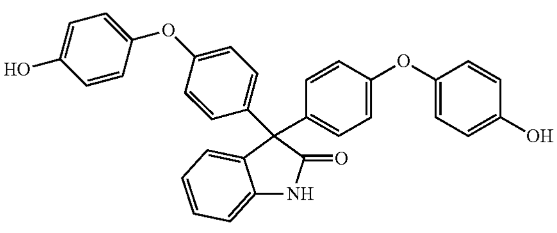 (A6) | 520 | 1.04 |

TABLE 1-continued
| Synthesis Example | Compound or polymer | Mw | Mw/Mn |
|---|---|---|---|
| 7 | 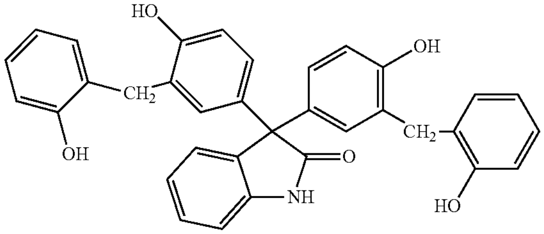 (A7) | 550 | 1.05 |
TABLE 2
| Synthesis Example | Compound or polymer | Mw | Mw/Mn |
|---|---|---|---|
| 8 | 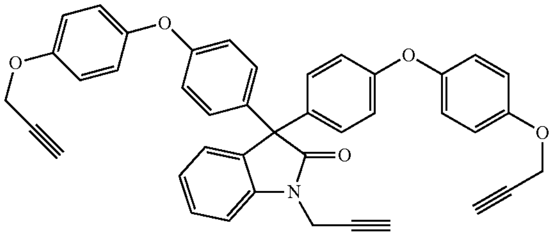 (A8) | 650 | 1.04 |
| 9 | 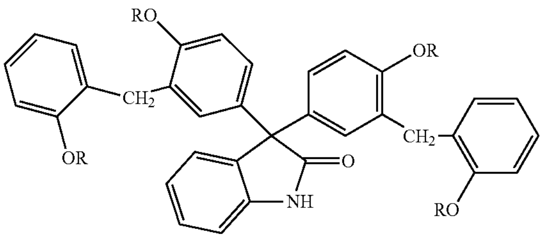 (A9) R = ----H or 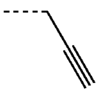 30:70 | 670 | 1.07 |
| 10 | 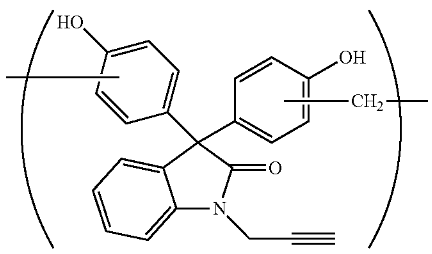 (A10) | 3300 | 1.82 |

TABLE 2-continued
| Synthesis Example | Compound or polymer | Mw | Mw/Mn |
|---|---|---|---|
| 11 | 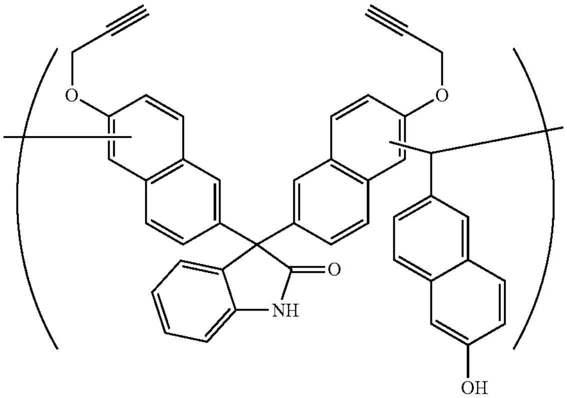 (A11) | 2900 | 2.12 |
| 12 | 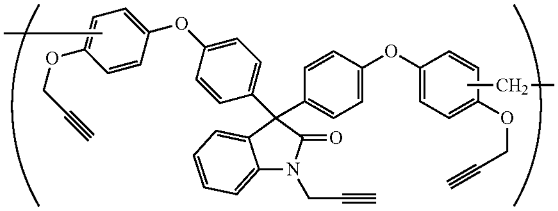 (A12) | 2800 | 1.65 |
| 13 | 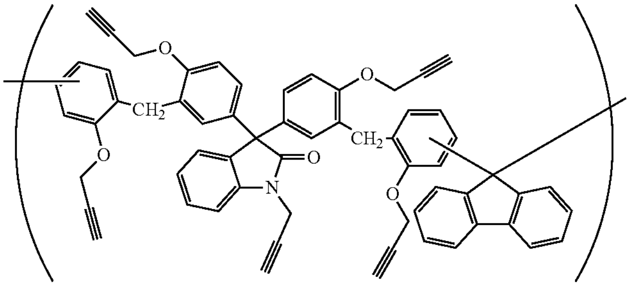 (A13) | 3000 | 1.56 |
TABLE 3
| Synthesis Example | Compound or polymer | Mw | Mw/Mn |
|---|---|---|---|
| 14 | 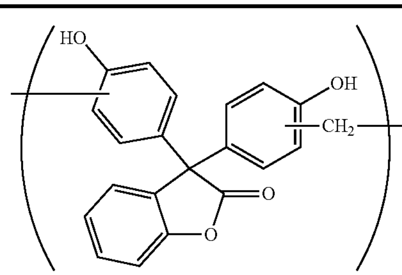 (R1) | 3200 | 4.88 |

TABLE 3-continued

| Synthesis Example | Compound or polymer | Mw | Mw/Mn |
|---|---|---|---|
| 15 | 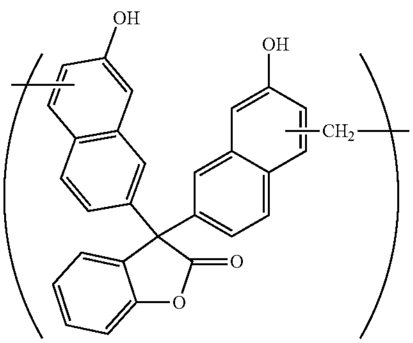 (R2) | 2600 | 3.55 |
| 16 | 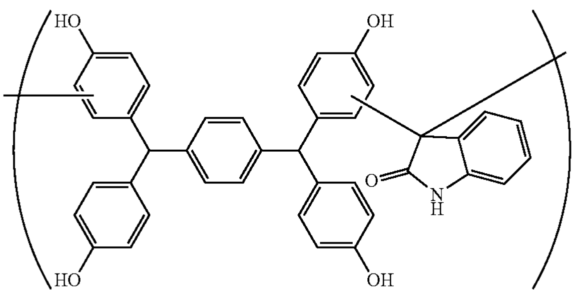 (R3) | 8500 | 2.30 |

Preparation of Compositions (UDL-1 to -18, Comparative UDL-1 to -9) for Forming Organic Film According to proportions shown in Table 4, the following were dissolved using propylene glycol monomethyl ether acetate (PGMEA) containing 0.1 mass % of PF-6320 (manufactured by Omnova Solutions, Inc.): the compounds and/or polymers (A1) to (A13) and (R1) to (R3), and the compounds (B8) and (B9) described in the Synthesis Examples; a crosslinking agent (XL); a thermal acid generator (TAG); and (S1) 1,6-diacetoxyhexane, having a boiling point of 260° C. and (S2) tripropylene glycol monomethyl ether, having a boiling point of 242° C. as high-boiling-point solvents. The resulting solutions were filtered through a 0.1-μm filter made of a fluorinated resin. Thus, compositions (UDL-1 to -18, comparative UDL-1 to -9) for forming an organic film were prepared.

Below, the structural formulae of the compounds, crosslinking agent, and thermal acid generator used in the preparation of the compositions for forming an organic film are shown.

(Compounds)

(B8)

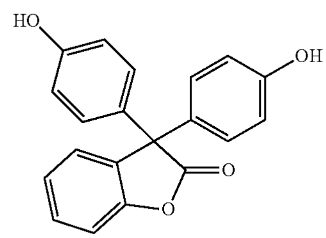

(B9)

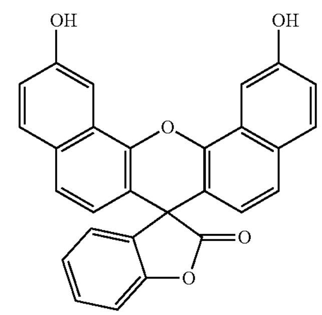

-continued (Crosslinking Agent)

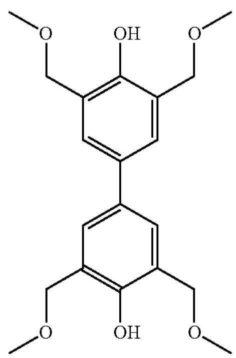

XL

-continued (Thermal Acid Generator)

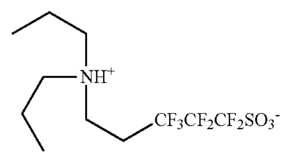

TAG

TABLE 4

| Composition for forming organic film | Compound/ polymer (parts by mass) | Crosslinking agent (parts by mass) | Thermal acid generator (parts by mass) | High-boiling-point solvent (parts by mass) | PGMEA (parts by mass) |
|---|---|---|---|---|---|
| UDL-1 | A1(10) | — | — | — | 90 |
| UDL-2 | A2(10) | — | — | — | 90 |
| UDL-3 | A3(10) | — | — | — | 90 |
| UDL-4 | A4(10) | — | — | — | 90 |
| UDL-5 | A5(10) | — | — | — | 90 |
| UDL-6 | A6(10) | — | — | — | 90 |
| UDL-7 | A7(10) | — | — | — | 90 |
| UDL-8 | A8(10) | — | — | — | 90 |
| UDL-9 | A9(10) | — | — | — | 90 |
| UDL-10 | A10(10) | — | — | — | 90 |
| UDL-11 | A11(10) | — | — | — | 90 |
| UDL-12 | A12(10) | — | — | — | 90 |
| UDL-13 | A13(10) | — | — | — | 90 |
| UDL-14 | A3(5)<br>A10(5) | — | — | — | 90 |
| UDL-15 | A6(5)<br>A12(5) | — | — | — | 90 |
| UDL-16 | A7(5)<br>A13(5) | — | — | — | 90 |
| UDL-17 | A1(10) | — | — | S1(10) | 80 |
| UDL-18 | A8(10) | — | — | S2(10) | 80 |
| Comparative UDL-1 | R1(10) | — | — | — | 90 |
| Comparative UDL-2 | R1(5)<br>B8(5) | — | — | — | 90 |
| Comparative UDL-3 | R2(10) | — | — | — | 90 |
| Comparative UDL-4 | R2(5)<br>B9(5) | — | — | — | 90 |
| Comparative UDL-5 | R3(10) | — | — | — | 90 |
| Comparative UDL-6 | R3(10) | XL(2.6) | TAG(0.25) | — | 90 |
| Comparative UDL-7 | B8(10) | — | — | — | 90 |
| Comparative UDL-8 | B9(10) | — | — | — | 90 |
| Comparative UDL-9 | B9(10) | XL(2.6) | TAG(0.25) | — | 90 |

Example 1: Solvent Resistance Test (Examples 1-1 to 1-18, Comparative Examples 1-1 to 1-9)

A silicon substrate was coated with one of the UDL-1 to -18 and comparative UDL-1 to -9 prepared above and baked in the atmosphere at the temperature shown in Table 5 for 60 seconds. Then, the film thickness was measured. A PGMEA solvent was dispensed on each film and allowed to stand for 30 seconds. The resultant was spin-dried and baked at 100° C. for 60 seconds to evaporate the PGMEA, and the film thicknesses before and after the PGMEA treatment were measured. Using the film thickness after the film formation and the film thickness after the PGMEA treatment, the film remaining percentage (b/a×100) was determined. Table 5 shows the results.

TABLE 5

| | Composition for forming organic film | Film thickness after film formation: a (Å) | Film thickness after PGMEA treatment: b (Å) | b/a × 100 (%) | Baking temperature |
|---|---|---|---|---|---|
| Example 1-1 | UDL-1 | 2003 | 2001 | 99.9 | 350° C. × 60 seconds |
| Example 1-2 | UDL-2 | 2007 | 2000 | 99.7 | 350° C. × 60 seconds |
| Example 1-3 | UDL-3 | 2013 | 1972 | 98.0 | 400° C. × 60 seconds |
| Example 1-4 | UDL-4 | 2008 | 1999 | 99.6 | 350° C. × 60 seconds |
| Example 1-5 | UDL-5 | 1996 | 1990 | 99.7 | 400° C. × 60 seconds |
| Example 1-6 | UDL-6 | 1990 | 1967 | 98.8 | 400° C. × 60 seconds |
| Example 1-7 | UDL-7 | 1992 | 1987 | 99.7 | 350° C. × 60 seconds |
| Example 1-8 | UDL-8 | 1994 | 1989 | 99.7 | 400° C. × 60 seconds |
| Example 1-9 | UDL-9 | 2014 | 2010 | 99.8 | 350° C. × 60 seconds |
| Example 1-10 | UDL-10 | 2013 | 2011 | 99.9 | 350° C. × 60 seconds |
| Example 1-11 | UDL-11 | 1990 | 1987 | 99.8 | 350° C. × 60 seconds |
| Example 1-12 | UDL-12 | 1994 | 1993 | 99.9 | 350° C. × 60 seconds |
| Example 1-13 | UDL-13 | 2000 | 1999 | 100.0 | 350° C. × 60 seconds |
| Example 1-14 | UDL-14 | 2010 | 2006 | 99.8 | 350° C. × 60 seconds |
| Example 1-15 | UDL-15 | 2013 | 2010 | 99.9 | 350° C. × 60 seconds |
| Example 1-16 | UDL-16 | 2003 | 2000 | 99.9 | 350° C. × 60 seconds |
| Example 1-17 | UDL-17 | 1995 | 1992 | 99.8 | 350° C. × 60 seconds |
| Example 1-18 | UDL-18 | 2008 | 2004 | 99.8 | 350° C. × 60 seconds |
| Comparative Example 1-1 | Comparative UDL-1 | 1995 | 1989 | 99.7 | 400° C. × 60 seconds |
| Comparative Example 1-2 | Comparative UDL-2 | 2012 | 987 | 49.1 | 400° C. × 60 seconds |
| Comparative Example 1-3 | Comparative UDL-3 | 1998 | 1990 | 99.6 | 400° C. × 60 seconds |
| Comparative Example 1-4 | Comparative UDL-4 | 2003 | 1376 | 68.7 | 400° C. × 60 seconds |
| Comparative Example 1-5 | Comparative UDL-5 | 2011 | 1267 | 63.0 | 400° C. × 60 seconds |
| Comparative Example 1-6 | Comparative UDL-6 | 2015 | 2009 | 99.7 | 350° C. × 60 seconds |
| Comparative Example 1-7 | Comparative UDL-7 | 2005 | 224 | 11.2 | 400° C. × 60 seconds |
| Comparative Example 1-8 | Comparative UDL-8 | 2002 | 320 | 16.0 | 400° C. × 60 seconds |
| Comparative Example 1-9 | Comparative UDL-9 | 2007 | 2004 | 99.9 | 350° C. × 60 seconds |

As shown in Table 5, the organic films (Examples 1-1 to 1-18) using the inventive compounds and/or polymers had a film remaining percentage after the PGMEA treatment of 98% or more in Examples 1-3 and 1-6, and 99% or more in the other Examples. This indicates that the crosslinking reaction was caused by the heat treatment, and sufficient solvent resistance was exhibited. Since Examples 1-3 and 1-6 use monomolecular compounds, and there are a few moieties that contribute to curing, the film remaining percentage was about 98% even when a treatment at 400° C. was performed. However, when combined with a polymer as in Examples 1-14 and 1-15, a solvent resistance of 99.0% or more was successfully achieved, and solvent resistance can be enhanced by combining the inventive compounds and polymers.

Meanwhile, comparing the Examples 1-1 to 1-18 with Comparative Examples 1-1 to 1-4 and 1-7 to 1-9, the inventive compounds are monomolecular, but exhibit sufficient curability. However, in Comparative Examples 1-7 and 1-8, where only the monomolecular compound was used, solvent resistance was not provided due to insufficient curability, insufficient heat resistance, or sublimation caused by a small molecular weight, and so forth. Therefore, in order to ensure solvent resistance, it was necessary to add a crosslinking agent as in Comparative Example 1-9. Meanwhile, as shown by the results of Comparative Examples 1-1 and 1-3, curability was achieved when the polymer alone was used. However, in Comparative Examples 1-2 and 1-4, where a polymer was also mixed, it can be considered that solvent resistance is not achieved due to factors such as insufficient curability, insufficient heat resistance, and sublimation as stated above. Meanwhile, in Comparative Example 1-5, even though a polymer was used, curability was not exhibited when only the polymer was used, and in order to achieve solvent resistance, it was necessary to add further, a crosslinking agent and a thermal acid generator as in Comparative Example 1-6.

Example 2: Heat Resistance Evaluation (Examples 2-1 to 2-18, Comparative Examples 2-1 to 2-9)

A silicon substrate was coated with one of the compositions (UDL-1 to -18, comparative UDL-1 to -9) for forming an organic film and baked in the atmosphere at the temperature shown in Table 6 for 60 seconds to form a coating film of about 200 nm. The film thickness A was measured. The substrate was further baked at 400° C. for 20 minutes under such a nitrogen stream that the oxygen concentration was controlled to 0.2 volume % or less. Then, the film thickness B was measured. Table 6 shows the results.

TABLE 6

| | Composition for forming organic film | Baking temperature | Film thickness after baking: A (Å) | Film thickness at 400° C.: B (Å) | Film remaining percentage % (B/A) |
|---|---|---|---|---|---|
| Example 2-1 | UDL-1 | 350° C. × 60 seconds | 2000 | 1986 | 99.3 |
| Example 2-2 | UDL-2 | 350° C. × 60 seconds | 2005 | 1979 | 98.7 |
| Example 2-3 | UDL-3 | 400° C. × 60 seconds | 1998 | 1953 | 97.7 |
| Example 2-4 | UDL-4 | 350° C. × 60 seconds | 2010 | 1992 | 99.1 |
| Example 2-5 | UDL-5 | 400° C. × 60 seconds | 2007 | 1997 | 99.5 |
| Example 2-6 | UDL-6 | 400° C. × 60 seconds | 2002 | 1958 | 97.8 |
| Example 2-7 | UDL-7 | 350° C. × 60 seconds | 2009 | 1985 | 98.8 |
| Example 2-8 | UDL-8 | 400° C. × 60 seconds | 2015 | 1995 | 99.0 |
| Example 2-9 | UDL-9 | 350° C. × 60 seconds | 1990 | 1978 | 99.4 |
| Example 2-10 | UDL-10 | 350° C. × 60 seconds | 1999 | 1990 | 99.5 |
| Example 2-11 | UDL-11 | 350° C. × 60 seconds | 1998 | 1988 | 99.5 |
| Example 2-12 | UDL-12 | 350° C. × 60 seconds | 1997 | 1987 | 99.5 |
| Example 2-13 | UDL-13 | 350° C. × 60 seconds | 1996 | 1990 | 99.7 |
| Example 2-14 | UDL-14 | 350° C. × 60 seconds | 1990 | 1976 | 99.3 |
| Example 2-15 | UDL-15 | 350° C. × 60 seconds | 2000 | 1981 | 99.1 |
| Example 2-16 | UDL-16 | 350° C. × 60 seconds | 2013 | 1998 | 99.3 |
| Example 2-17 | UDL-17 | 350° C. × 60 seconds | 2002 | 1985 | 99.2 |
| Example 2-18 | UDL-18 | 350° C. × 60 seconds | 2001 | 1988 | 99.4 |
| Comparative Example 2-1 | Comparative UDL-1 | 400° C. × 60 seconds | 1995 | 1764 | 88.4 |
| Comparative Example 2-2 | Comparative UDL-2 | 400° C. × 60 seconds | 2012 | 1420 | 70.6 |
| Comparative Example 2-3 | Comparative UDL-3 | 400° C. × 60 seconds | 1998 | 1841 | 92.1 |
| Comparative Example 2-4 | Comparative UDL-4 | 400° C. × 60 seconds | 2003 | 1536 | 76.7 |
| Comparative Example 2-5 | Comparative UDL-5 | 400° C. × 60 seconds | 2011 | 1830 | 91.0 |
| Comparative Example 2-6 | Comparative UDL-6 | 350° C. × 60 seconds | 2015 | 1921 | 95.3 |
| Comparative Example 2-7 | Comparative UDL-7 | 400° C. × 60 seconds | 2005 | 123 | 6.1 |
| Comparative Example 2-8 | Comparative UDL-8 | 400° C. × 60 seconds | 2002 | 356 | 17.8 |
| Comparative Example 2-9 | Comparative UDL-9 | 350° C. × 60 seconds | 2007 | 1811 | 90.2 |

As shown in Table 6, the organic films that the inventive compositions for forming an organic film (Examples 2-1 to 2-18) give had a film thickness decrease of less than 3% even after baking at 400° C. over a long time. This indicates that the inventive compositions were excellent in heat resistance. In particular, the compounds and polymers having a propargyloxy group introduced as a substituent provide films maintained a film remaining percentage of 99% or more, and this indicates particularly excellent heat resistance. Meanwhile, in the same manner as in the solvent resistance test of Example 1, it can be observed that with respect to Examples 2-3, 2-6, and 2-7, not only solvent resistance, but also heat resistance was also improved by combining with a polymer (Example 2-14 to 2-16).

On the other hand, in Comparative Examples 2-2, 2-4, 2-5, 2-7, and 2-8, the film remaining percentage had a low value when solvent resistance was not achieved in the results of Example 1. In Comparative Examples 2-7 and 2-8, where a monomolecular compound was used, almost no organic film remained after maintaining the temperature of 400° C., and in Comparative Examples 2-1, 2-3, and 2-6, too, where solvent resistance was achieved by adding a crosslinking agent or using a polymer, the film remaining percentage had a low value compared with the Examples of the present invention. Thus, it can be observed that the organic films formed by using the inventive compounds and polymers were excellent in heat resistance owing to the contribution of the cyclic amide structure.

Example 3: Film-Formability Evaluation (Examples 3-1 to 3-18, Comparative Examples 3-1 to 3-9)

Each of the compositions (UDL-1 to -18, comparative UDL-1 to -9) for forming an organic film prepared above were respectively applied onto each of a Bare-Si substrate, a substrate treated with hexamethyldisilazane (HMDS), and a substrate treated with SiON, shown in Table 7, and baked in the atmosphere at the temperature shown in Table 7 for 60 seconds to form an organic film having a film thickness of 100 nm. The organic films thus formed were observed with an optical microscope (ECLIPSE L200 manufactured by Nikon INSTECH CO., LTD.) to check for coating abnormality. Note that in the present evaluation, the film thickness is made thin in order to evaluate the coatability. This is a severe evaluation condition where film formation abnormality is liable to occur.

TABLE 7

| | Composition for forming organic film | Baking temperature | Bare-Si substrate | HMDS-treated substrate | SiON-treated substrate |
|---|---|---|---|---|---|
| Example 3-1 | UDL-1 | 350° C. × 60 seconds | No abnormality | No abnormality | No abnormality |
| Example 3-2 | UDL-2 | 350° C. × 60 seconds | No abnormality | No abnormality | No abnormality |
| Example 3-3 | UDL-3 | 400° C. × 60 seconds | No abnormality | No abnormality | Several pinhole defects |
| Example 3-4 | UDL-4 | 350° C. × 60 seconds | No abnormality | No abnormality | No abnormality |
| Example 3-5 | UDL-5 | 400° C. × 60 seconds | No abnormality | No abnormality | No abnormality |
| Example 3-6 | UDL-6 | 400° C. × 60 seconds | No abnormality | No abnormality | No abnormality |
| Example 3-7 | UDL-7 | 350° C. × 60 seconds | No abnormality | No abnormality | No abnormality |
| Example 3-8 | UDL-8 | 400° C. × 60 seconds | No abnormality | No abnormality | No abnormality |
| Example 3-9 | UDL-9 | 350° C. × 60 seconds | No abnormality | No abnormality | No abnormality |
| Example 3-10 | UDL-10 | 350° C. × 60 seconds | No abnormality | No abnormality | No abnormality |
| Example 3-11 | UDL-11 | 350° C. × 60 seconds | No abnormality | No abnormality | No abnormality |
| Example 3-12 | UDL-12 | 350° C. × 60 seconds | No abnormality | No abnormality | No abnormality |
| Example 3-13 | UDL-13 | 350° C. × 60 seconds | No abnormality | No abnormality | No abnormality |
| Example 3-14 | UDL-14 | 350° C. × 60 seconds | No abnormality | No abnormality | No abnormality |
| Example 3-15 | UDL-15 | 350° C. × 60 seconds | No abnormality | No abnormality | No abnormality |
| Example 3-16 | UDL-16 | 350° C. × 60 seconds | No abnormality | No abnormality | No abnormality |
| Example 3-17 | UDL-17 | 350° C. × 60 seconds | No abnormality | No abnormality | No abnormality |
| Example 3-18 | UDL-18 | 350° C. × 60 seconds | No abnormality | No abnormality | No abnormality |
| Comparative Example 3-1 | Comparative UDL-1 | 400° C. × 60 seconds | No abnormality | No abnormality | Several pinhole defects |
| Comparative Example 3-2 | Comparative UDL-2 | 400° C. × 60 seconds | Countless pinhole defects | Countless pinhole defects | Countless pinhole defects |
| Comparative Example 3-3 | Comparative UDL-3 | 400° C. × 60 seconds | No abnormality | No abnormality | Several pinhole defects |
| Comparative Example 3-4 | Comparative UDL-4 | 400° C. × 60 seconds | Countless pinhole defects | Countless pinhole defects | Countless pinhole defects |
| Comparative Example 3-5 | Comparative UDL-5 | 400° C. × 60 seconds | Countless pinhole defects | Countless pinhole defects | Countless pinhole defects |
| Comparative Example 3-6 | Comparative UDL-6 | 350° C. × 60 seconds | No abnormality | No abnormality | No abnormality |
| Comparative Example 3-7 | Comparative UDL-7 | 400° C. × 60 seconds | Countless pinhole defects | Countless pinhole defects | Countless pinhole defects |
| Comparative Example 3-8 | Comparative UDL-8 | 400° C. × 60 seconds | Countless pinhole defects | Countless pinhole defects | Countless pinhole defects |
| Comparative Example 3-9 | Comparative UDL-9 | 350° C. × 60 seconds | No abnormality | Several pinhole defects | No abnormality |

As shown in Table 7, it can be observed that the inventive compositions for forming an organic film (Examples 3-1 to 3-2, 3-4 to 3-18) had no substrate dependency, and that film-formability was achieved. In Example 3-3, a small number of pinholes were observed in the SiON substrate since a monomolecular compound was used. However, compared with the fact that in Comparative Examples 3-7 and 3-8, where a monomolecular compound (B8, B9) having a similar structure (cyclic ester) was used, it was impossible to achieve film-formability in any of the substrates due to insufficient curability and insufficient heat resistance, it can be seen that film-formability was improved. Thus, the advantageous effects of the present invention can be observed. Furthermore, as observed when comparing Example 3-3 with Example 3-14, it is also possible to improve film-formability by using polymers in combination. Meanwhile, as indicated by Comparative Examples 3-1 to 3-5 and 3-9, it was impossible to achieve film-formability depending on the substrate even when a crosslinking agent and polymer were added (Comparative Examples 3-2, 3-4, 3-9), or when the polymer was used alone (Comparative Examples 3-1, 3-3, 3-5).

From the comparison of these results, it can be conjectured that in the inventive compounds and polymers, the cyclic amide structure functions as an adhesive group, and contributes to the improvement of film-formability. As a similar tendency, this can also be conjectured from the fact that in Comparative Examples 3-5 and 3-6, where a polymer (R3) having a cyclic amide structure was used, it was impossible to achieve film-formability when the polymer having no curability and poor heat resistance was used alone (Comparative Example 3-5), but in Comparative Example 3-6, where a crosslinking agent was added to form a cured film, film-formability was improved.

As described, it can be seen that the inventive compositions for forming an organic film are capable of forming an organic film excellent in curability and heat resistance, and moreover, exhibit excellent film-formability on various substrates by containing a material for forming an organic film shown by a particular formula whether the material is a monomolecular compound, a polymer, or a mixture of one or more kinds of the compound and one or more kinds of the polymer, even when a crosslinking agent, a thermal acid generator, and so forth are not added.

Example 4: Filling Property Evaluation (Examples 4-1 to 4-18, Comparative Examples 4-1 to 4-9)

The compositions (UDL-1 to -18, comparative UDL-1 to -9) for forming an organic film prepared above were each applied onto an $SiO_2$ wafer substrate having a dense hole pattern (hole diameter: 0.16 μm, hole depth: 0.50 μm, distance between the centers of two adjacent holes: 0.32 μm) and baked in the atmosphere at the temperature shown in Table 8 for 60 seconds to form an organic film. The substrate used was a base substrate 7 ($SiO_2$ wafer substrate) having a dense hole pattern as shown in FIGS. 2 (G) (top view) and (H) (sectional view). The sectional shapes of the resulting wafer substrates were observed with a scanning electron microscope (SEM) to check whether or not the holes were filled with the organic film 8 without voids (space). Table 8 shows the results. If a composition for forming an organic film having poor filling property is used, voids occur inside the holes in this evaluation. When a composition for forming an organic film having good filling property is used, the holes are filled with the organic film without voids in this evaluation as shown in FIG. 2 (I).

TABLE 8

| | Composition for forming organic film | Baking temperature | Presence/absence of voids |
|---|---|---|---|
| Example 4-1 | UDL-1 | 350° C. × 60 seconds | Absent |
| Example 4-2 | UDL-2 | 350° C. × 60 seconds | Absent |
| Example 4-3 | UDL-3 | 400° C. × 60 seconds | Absent |
| Example 4-4 | UDL-4 | 350° C. × 60 seconds | Absent |
| Example 4-5 | UDL-5 | 400° C. × 60 seconds | Absent |
| Example 4-6 | UDL-6 | 400° C. × 60 seconds | Absent |
| Example 4-7 | UDL-7 | 350° C. × 60 seconds | Absent |
| Example 4-8 | UDL-8 | 400° C. × 60 seconds | Absent |
| Example 4-9 | UDL-9 | 350° C. × 60 seconds | Absent |
| Example 4-10 | UDL-10 | 350° C. × 60 seconds | Absent |
| Example 4-11 | UDL-11 | 350° C. × 60 seconds | Absent |
| Example 4-12 | UDL-12 | 350° C. × 60 seconds | Absent |
| Example 4-13 | UDL-13 | 350° C. × 60 seconds | Absent |
| Example 4-14 | UDL-14 | 350° C. × 60 seconds | Absent |
| Example 4-15 | UDL-15 | 350° C. × 60 seconds | Absent |
| Example 4-16 | UDL-16 | 350° C. × 60 seconds | Absent |
| Example 4-17 | UDL-17 | 350° C. × 60 seconds | Absent |
| Example 4-18 | UDL-18 | 350° C. × 60 seconds | Absent |
| Comparative Example 4-1 | Comparative UDL-1 | 400° C. × 60 seconds | Present |
| Comparative Example 4-2 | Comparative UDL-2 | 400° C. × 60 seconds | Present |
| Comparative Example 4-3 | Comparative UDL-3 | 400° C. × 60 seconds | Present |
| Comparative Example 4-4 | Comparative UDL-4 | 400° C. × 60 seconds | Present |
| Comparative Example 4-5 | Comparative UDL-5 | 400° C. × 60 seconds | Present |
| Comparative Example 4-6 | Comparative UDL-6 | 350° C. × 60 seconds | Present |
| Comparative Example 4-7 | Comparative UDL-7 | 400° C. × 60 seconds | Present |
| Comparative Example 4-8 | Comparative UDL-8 | 400° C. × 60 seconds | Present |
| Comparative Example 4-9 | Comparative UDL-9 | 350° C. × 60 seconds | Absent |

As shown by Examples 4-1 to 4-18 in Table 8, it has been revealed that every material for forming an organic film using the inventive compound and/or polymer was able to fill the hole patterns without voids, and was excellent in filling property. On the other hand, in Comparative Examples 4-1 to 4-5, 4-7, and 4-8, it can be considered that, as indicated by the results of Examples 1 and 2, filling failure occurred since solvent resistance was not achieved and heat resistance was insufficient. Meanwhile, in Comparative Example 4-6, it can be considered that thermal flowability was poor compared with monomolecular compounds, and moreover, a sudden curing reaction occurred due to the action of the thermal acid generator since a polymer was used, although solvent resistance was achieved, and that therefore, thermal flowability was insufficient, and voids due to poor filling occurred. Meanwhile, in Comparative Example 4-9, it can be observed that since a single compound was used, filling property was achieved owing to the contribution of the thermal flowability.

Example 5: Planarizing Property Evaluation (Examples 5-1 to 5-18, Comparative Examples 5-1 to 5-9)

The compositions (UDL-1 to -18, comparative UDL-1 to -9) for forming an organic film prepared above were each applied onto a base substrate 9 ($SiO_2$ wafer substrate) having a giant isolated trench pattern (FIG. 3 (J), trench width: 10 μm, trench depth: 0.1 μm) and baked in the atmosphere at the temperature shown in Table 9 for 60 seconds. Then, a step (delta 10 in FIG. 3 (K)) between the trench portion and the non-trench portion of an organic film 10 was observed with an atomic force microscope (AFM) NX10 manufactured by Park systems Corp. Table 9 shows the results. In this evaluation, the smaller the step, the better the planarizing property. Note that, in this evaluation, a trench pattern having a depth of 0.10 μm was generally planarized using an organic film having a film thickness of approximately 0.2 μm. This is a severe evaluation condition to evaluate the planarizing property.

TABLE 9

| | Composition for forming organic film | Baking temperature | Step (nm) |
|---|---|---|---|
| Example 5-1 | UDL-1 | 350° C. × 60 seconds | 35 |
| Example 5-2 | UDL-2 | 350° C. × 60 seconds | 40 |
| Example 5-3 | UDL-3 | 400° C. × 60 seconds | 55 |
| Example 5-4 | UDL-4 | 350° C. × 60 seconds | 25 |
| Example 5-5 | UDL-5 | 400° C. × 60 seconds | 30 |
| Example 5-6 | UDL-6 | 400° C. × 60 seconds | 45 |
| Example 5-7 | UDL-7 | 350° C. × 60 seconds | 55 |
| Example 5-8 | UDL-8 | 400° C. × 60 seconds | 25 |
| Example 5-9 | UDL-9 | 350° C. × 60 seconds | 45 |
| Example 5-10 | UDL-10 | 350° C. × 60 seconds | 70 |
| Example 5-11 | UDL-11 | 350° C. × 60 seconds | 70 |
| Example 5-12 | UDL-12 | 350° C. × 60 seconds | 55 |
| Example 5-13 | UDL-13 | 350° C. × 60 seconds | 70 |
| Example 5-14 | UDL-14 | 350° C. × 60 seconds | 60 |
| Example 5-15 | UDL-15 | 350° C. × 60 seconds | 50 |
| Example 5-16 | UDL-16 | 350° C. × 60 seconds | 60 |
| Example 5-17 | UDL-17 | 350° C. × 60 seconds | 30 |
| Example 5-18 | UDL-18 | 350° C. × 60 seconds | 20 |
| Comparative Example 5-1 | Comparative UDL-1 | 400° C. × 60 seconds | 90 |
| Comparative Example 5-2 | Comparative UDL-2 | 400° C. × 60 seconds | 90 |
| Comparative Example 5-3 | Comparative UDL-3 | 400° C. × 60 seconds | 95 |
| Comparative Example 5-4 | Comparative UDL-4 | 400° C. × 60 seconds | 90 |
| Comparative Example 5-5 | Comparative UDL-5 | 400° C. × 60 seconds | 90 |
| Comparative Example 5-6 | Comparative UDL-6 | 350° C. × 60 seconds | 95 |
| Comparative Example 5-7 | Comparative UDL-7 | 400° C. × 60 seconds | 100 |
| Comparative Example 5-8 | Comparative UDL-8 | 400° C. × 60 seconds | 100 |
| Comparative Example 5-9 | Comparative UDL-9 | 350° C. × 60 seconds | 85 |

As shown by Examples 5-1 to 5-18 in Table 9, every material for forming an organic film had smaller steps in the organic film between the trench portion and the non-trench portion when the inventive compounds and/or polymers were used compared with Comparative Examples 5-1 to 5-9, showing that planarizing property was excellent. In particular, the compositions containing a condensation-dehydration product of phenol or catechol and indole-2,3-dione with a propargyl group as substituents, as in Examples 5-4, 5-5, and 5-8, show excellent results. This can be considered to be because of excellent results of heat resistance achieved in the heat resistance test of Example 2, and because of reduced viscosity of the compound caused by a hydroxy group being capped by etherification. In Comparative Examples 5-2, 5-4, 5-5, 5-7, and 5-8, as indicated by the results of the heat resistance test in Example 2, heat resistance was insufficient, so that film shrinking during baking was large. It can be considered that a difference between film thickness and the step size thus occurred, and planarizing property was degraded. Meanwhile, in Comparative Examples 5-6 and 5-9, it can be considered that since a crosslinking agent was used in order to ensure solvent resistance, a sudden curing reaction occurred, so that it was impossible to receive the benefits of the thermal flowability, and planarizing property was degraded. From a comparison of Examples 5-17 and 5-18 with Examples 5-1 and 5-8, containing no high-boiling-point solvent, it can also be observed that flatness was further improved by the addition of the high-boiling-point solvent. In addition, comparing Examples 5-14 to 5-16, where an inventive compound and polymer were mixed, with Examples 5-10, 5-12, and 5-13, where only a polymer was used, planarizing property was improved. By adjusting the amount to be contained, it is also possible to improve flatness without losing various physical properties such as heat resistance, twisting resistance, and etching resistance, required in an organic film.

Example 6: Adhesiveness Test (Examples 6-1 to 6-18, Comparative Examples 6-1 to 6-4)

The compositions (UDL-1 to -16, comparative UDL-1, -3, -6, -9) for forming an organic film were respectively applied onto $SiO_2$ wafer substrates and baked using a hot plate in the atmosphere at the temperature shown in Table 10 for 60 seconds. Thus, organic films each with a film thickness of 200 nm were formed. This wafer with an organic film was cut into a 1×1 cm square, and an aluminum pin with epoxy adhesive was fastened to the cut wafer with a dedicated jig. Thereafter, the assembly was heated with an oven at 150° C. for 1 hour to bond the aluminum pin to the substrate. After cooling to room temperature, initial adhesiveness was evaluated based on the resistance force by a thin-film adhesion strength measurement apparatus (Sebastian Five-A). Note that, regarding comparative UDL-2, -4, -5, -7, and -8, where it was impossible to achieve solvent resistance in Example 1, it was impossible to perform the adhesiveness test.

FIG. 4 shows an explanatory diagram showing the adhesiveness measurement method. In FIG. 4, reference number 11 denotes a silicon wafer (substrate), 12 denotes a cured film, 14 denotes an aluminum pin with adhesive, 13 denotes a support, 15 denotes a grip, and 16 denotes a tensile direction. Each adhesive force is an average of 12 measurement points, and a larger value indicates that the adhesive film has higher adhesiveness with respect to the substrate. The adhesiveness was evaluated by comparing the obtained values. Table 10 shows the results.

TABLE 10

| | Composition for forming organic film | Baking temperature | Adhesion (mN) |
|---|---|---|---|
| Example 6-1 | UDL-1 | 350° C. × 60 seconds | 530 |
| Example 6-2 | UDL-2 | 350° C. × 60 seconds | 480 |
| Example 6-3 | UDL-3 | 400° C. × 60 seconds | 560 |
| Example 6-4 | UDL-4 | 350° C. × 60 seconds | 420 |
| Example 6-5 | UDL-5 | 400° C. × 60 seconds | 450 |
| Example 6-6 | UDL-6 | 400° C. × 60 seconds | 720 |
| Example 6-7 | UDL-7 | 350° C. × 60 seconds | 730 |
| Example 6-8 | UDL-8 | 400° C. × 60 seconds | 490 |
| Example 6-9 | UDL-9 | 350° C. × 60 seconds | 630 |
| Example 6-10 | UDL-10 | 350° C. × 60 seconds | 620 |
| Example 6-11 | UDL-11 | 350° C. × 60 seconds | 550 |
| Example 6-12 | UDL-12 | 350° C. × 60 seconds | 510 |
| Example 6-13 | UDL-13 | 350° C. × 60 seconds | 480 |
| Example 6-14 | UDL-14 | 350° C. × 60 seconds | 630 |
| Example 6-15 | UDL-15 | 350° C. × 60 seconds | 610 |
| Example 6-16 | UDL-16 | 350° C. × 60 seconds | 600 |
| Example 6-17 | UDL-17 | 350° C. × 60 seconds | 530 |
| Example 6-18 | UDL-18 | 350° C. × 60 seconds | 490 |
| Comparative Example 6-1 | Comparative UDL-1 | 400° C. × 60 seconds | 370 |
| Comparative Example 6-2 | Comparative UDL-3 | 400° C. × 60 seconds | 390 |
| Comparative Example 6-3 | Comparative UDL-6 | 350° C. × 60 seconds | 620 |
| Comparative Example 6-4 | Comparative UDL-9 | 350° C. × 60 seconds | 310 |

As shown in Examples 6-1 to 6-18 in Table 10, it can be observed that when the inventive compounds and/or polymers were used, the organic films exhibited higher adhesion than in Comparative Examples 6-1, 6-2, and 6-4. Meanwhile, in Comparative Example 6-3, high adhesion was exhibited because a similar cyclic amide structure was contained. It can also be considered from these results that adhesion was enhanced by the function of the particular hetero ring structure introduced to the inventive compounds and polymers, and excellent film-formability was exhibited as seen in the results of Example 3.

Example 7: Patterning Test (Examples 7-1 to 7-18, Comparative Examples 7-1 to 7-4)

The compositions (UDL-1 to -18, comparative UDL-1, -3, -6, -9) for forming an organic film were respectively applied onto a Bare-Si substrate having a trench pattern (trench width: 10 μm, trench depth: 0.10 μm) with an $SiO_2$ film formed, the $SiO_2$ film having a film thickness of 200 nm treated with HMDS. Then, an organic film (resist underlayer film) was formed by baking under the conditions shown in Table 14 in the atmosphere so that the film thickness on the Bare-Si substrate was 200 nm. A silicon-containing resist middle layer film material (SOG1) was applied onto the organic film and baked at 220° C. for 60 seconds to form a resist middle layer film having a film thickness of 35 nm. A resist upper layer film material (SL resist for ArF) was applied thereon and baked at 105° C. for 60 seconds to form a resist upper layer film having a film thickness of 100 nm. A liquid immersion top coat (TC-1) was applied onto the resist upper layer film and baked at 90° C. for 60 seconds to form a top coat having a film thickness of 50 nm. Note that regarding comparative UDL-2, -4, -5, -7, and -8, where it was impossible to achieve solvent resistance in Example 1, it was impossible to perform the patterning test since a silicon-containing resist middle layer film material was not applied.

The resist upper layer film material (SL resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 11; and filtering the solution through a 0.1-μm filter made of a fluorinated resin.

TABLE 11

| | Polymer (parts by mass) | Acid generator (parts by mass) | Basic compound (parts by mass) | Solvent (parts by mass) |
|---|---|---|---|---|
| Monolayer resist for ArF | RP1 (100) | PAG1 (6.6) | Amine1 (0.8) | PGMEA (2500) |

The structural formulae of the polymer (RP1), acid generator (PAG1), and basic compound (Amine1) used are shown below.

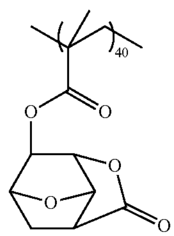

RP1

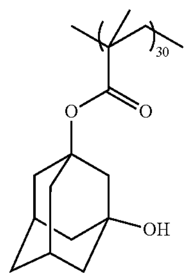

Mw7,800

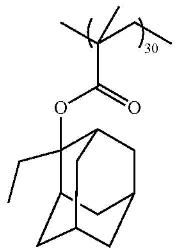

PAG1

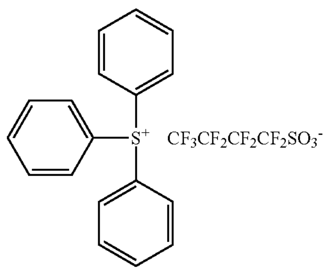

-continued

Amine1

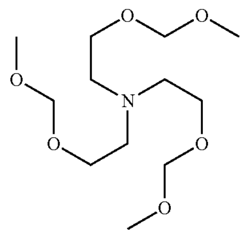

The liquid immersion top coat material (TC-1) was prepared by: dissolving a top coat polymer (PP1) into organic solvents in proportions shown in Table 12; and filtering the solution through a 0.1-μm filter made of a fluorinated resin.

TABLE 12

| | Polymer (parts by mass) | Organic solvent (parts by mass) |
|---|---|---|
| TC-1 | PP1 (100) | Diisoamyl ether (2700) 2-methyl-1-butanol (270) |

The structural formula of the used polymer (PP1) is shown below.

PP1

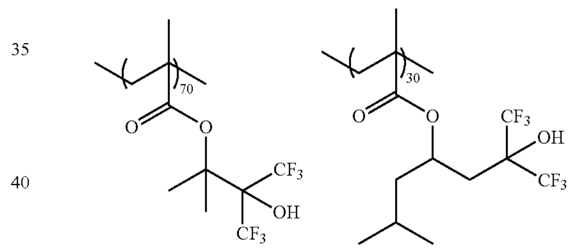

Mw8,800

The silicon-containing resist middle layer film material (SOG1) was prepared by: dissolving a polymer shown by an ArF silicon-containing middle layer film polymer (SiP1) and a crosslinking catalyst (CAT1) into an organic solvent containing 0.1 mass % FC-4430 (manufactured by Sumitomo 3M Ltd.) in proportions shown in Table 13; and filtering the solution through a filter made of a fluorinated resin with a pore size of 0.1 μm.

TABLE 13

| | Polymer (parts by mass) | Thermally crosslinking catalyst (parts by mass) | Organic solvent (parts by mass) |
|---|---|---|---|
| SOG1 | SiP1 (100) | CAT1 (1) | Propylene glycol monoethyl ether (4000) |

The structural formulae of the used ArF silicon-containing middle layer film polymer (SiP1) and crosslinking catalyst (CAT1) are shown below.

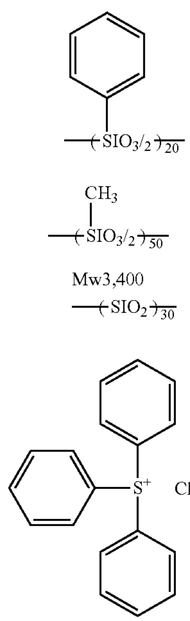

SiP1

CAT1

Next, the resulting substrate was exposed to light with an ArF liquid immersion exposure apparatus (NSR-S610C manufactured by Nikon Corporation, NA: 1.30, σ: 0.98/0.65, 35° s-polarized dipole illumination, 6% halftone phase shift mask) while changing the exposure, baked (PEB) at 100° C. for 60 seconds, and developed with a 2.38 mass % aqueous solution of tetramethylammonium hydroxide (TMAH) for 30 seconds. Thus, a positive line and space pattern was obtained with a pitch of 100 nm and a resist line width of 50 nm to 30 nm.

Next, using an etching apparatus Telius manufactured by Tokyo Electron Limited, the silicon-containing middle layer film was processed by dry etching while using the resist pattern as a mask; the organic film was processed while using the silicon-containing middle layer film as a mask; and the $SiO_2$ film was processed while using the organic film as a mask.

The etching conditions were as follows.

Conditions for transferring the resist pattern to the SOG film.

Chamber pressure: 10.0 Pa
RF power: 1,500 W
$CF_4$ gas flow rate: 15 sccm
$O_2$ gas flow rate: 75 sccm
Time: 15 sec Conditions for transferring the pattern from the SOG film to the organic film.

Chamber pressure: 2.0 Pa
RF power: 500 W
Ar gas flow rate: 75 sccm
$O_2$ gas flow rate: 45 sccm
Time: 120 sec Conditions for transferring to the $SiO_2$ film.

Chamber pressure: 2.0 Pa
RF power: 2,200 W
$C_5F_{12}$ gas flow rate: 20 sccm
$C_2F_6$ gas flow rate: 10 sccm
Ar gas flow rate: 300 sccm
$O_2$ gas flow rate: 60 sccm
Time: 90 sec The pattern cross sections were observed with an electron microscope (S-4700) manufactured by Hitachi, Ltd., the profiles were compared, and summarized in Table 14.

TABLE 14

| | Composition for forming organic film | Baking temperature | Pattern profile after etching for transferring to substrate |
|---|---|---|---|
| Example 7-1 | UDL-1 | 350° C. × 60 seconds | Vertical profile |
| Example 7-2 | UDL-2 | 350° C. × 60 seconds | Vertical profile |
| Example 7-3 | UDL-3 | 400° C. × 60 seconds | Vertical profile |
| Example 7-4 | UDL-4 | 350° C. × 60 seconds | Vertical profile |
| Example 7-5 | UDL-5 | 400° C. × 60 seconds | Vertical profile |
| Example 7-6 | UDL-6 | 400° C. × 60 seconds | Vertical profile |
| Example 7-7 | UDL-7 | 350° C. × 60 seconds | Vertical profile |
| Example 7-8 | UDL-8 | 400° C. × 60 seconds | Vertical profile |
| Example 7-9 | UDL-9 | 350° C. × 60 seconds | Vertical profile |
| Example 7-10 | UDL-10 | 350° C. × 60 seconds | Vertical profile |
| Example 7-11 | UDL-11 | 350° C. × 60 seconds | Vertical profile |
| Example 7-12 | UDL-12 | 350° C. × 60 seconds | Vertical profile |
| Example 7-13 | UDL-13 | 350° C. × 60 seconds | Vertical profile |
| Example 7-14 | UDL-14 | 350° C. × 60 seconds | Vertical profile |
| Example 7-15 | UDL-15 | 350° C. × 60 seconds | Vertical profile |
| Example 7-16 | UDL-16 | 350° C. × 60 seconds | Vertical profile |
| Example 7-17 | UDL-17 | 350° C. × 60 seconds | Vertical profile |
| Example 7-18 | UDL-18 | 350° C. × 60 seconds | Vertical profile |
| Comparative Example 7-1 | Comparative UDL-1 | 400° C. × 60 seconds | Pattern profile collapse |
| Comparative Example 7-2 | Comparative UDL-3 | 400° C. × 60 seconds | Pattern profile collapse |
| Comparative Example 7-3 | Comparative UDL-6 | 400° C. × 60 seconds | Pattern profile collapse |
| Comparative Example 7-4 | Comparative UDL-9 | 400° C. × 60 seconds | Pattern profile collapse |

As shown in Table 14, it was confirmed from the results of the inventive compositions for forming an organic film (Examples 7-1 to 7-18) that the resist upper layer film pattern was favorably transferred to the final substrate in each case, and that the inventive compositions for forming an organic film are suitably used in fine processing according to the multilayer resist method. Meanwhile, in Comparative Examples 7-1 to 7-4, pattern collapse occurred during patterning due to pinholes generated during film formation as demonstrated in the results of the film-formability test of Example 3, and it was impossible to form a pattern.

From the above, it was revealed that the inventive compositions for forming an organic film have good film-formability and excellent filling and planarizing properties. Thus, the inventive compositions are extremely useful as organic film materials used in multilayer resist methods. Moreover, the inventive patterning process using these compositions can form a fine pattern with high precision even when the body to be processed is a stepped substrate.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A composition for forming an organic film, comprising: a material for forming an organic film and an organic solvent, wherein the material for forming an organic film is a polymer having a repeating unit shown by the following general formula (4) and/or (5), (4)

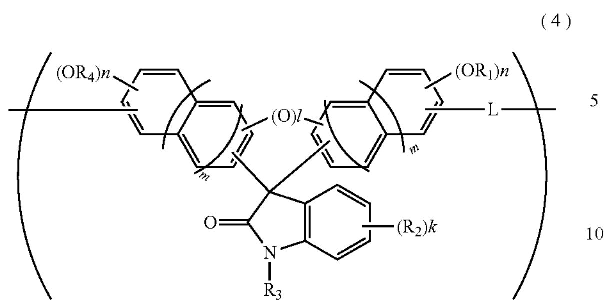

wherein $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, "k" represents an integer of 0 to 2, and L represents a divalent organic group having 1 to 40 carbon atoms, (5)

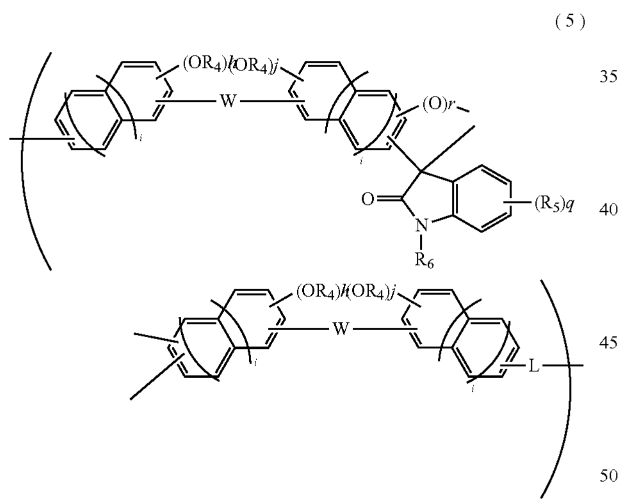

wherein $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship $1 \leq h+j \leq 4$, "r" represents 0 or 1, aromatic rings forming a cyclic ether structure with one another when r=1, W represents a single bond or any divalent group shown by the following formulae (3), and L represents a divalent organic group having 1 to 40 carbon atoms, (3)

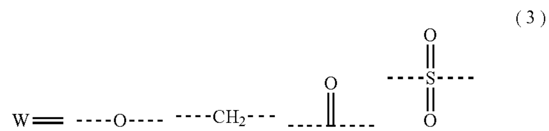

wherein a broken line represents an attachment point.

2. The composition for forming an organic film according to claim 1, wherein the L is a divalent organic group shown by the following general formula (6), (6)

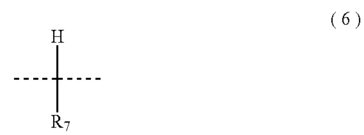

wherein $R_7$ represents a hydrogen atom or an aromatic ring-containing organic group having 1 to 20 carbon atoms, and a broken line represents an attachment point.

3. The composition for forming an organic film according to claim 1, wherein the polymer has a weight-average molecular weight of 1000 to 5000 measured by gel permeation chromatography in terms of polystyrene.

4. A composition for forming an organic film, comprising: a material for forming an organic film and an organic solvent, wherein the material for forming an organic film is a compound shown by the following general formula (1) and/or (2), (1)

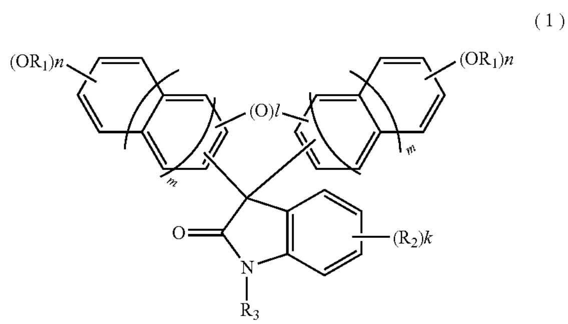

wherein $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, "k" represents an integer of 0 to 2, (2)

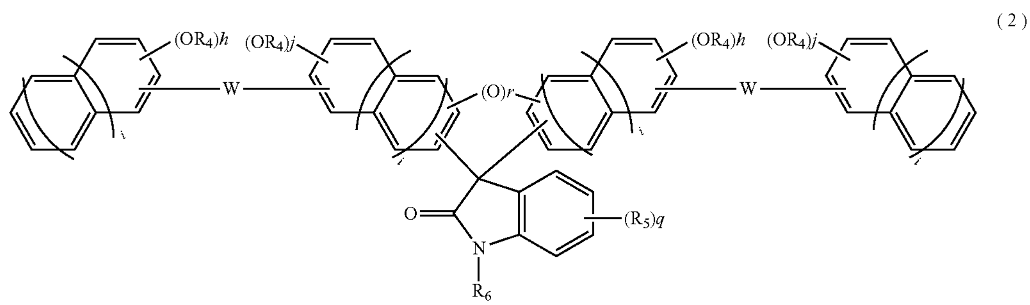

wherein $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship $1 \leq h+j \leq 4$, "r" represents 0 or 1, aromatic rings forming a cyclic ether structure with one another when r=1, and W represents any divalent group shown by the following formulae (3), (3)

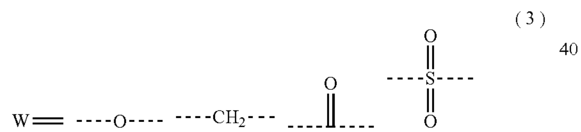

wherein a broken line represents an attachment point, and wherein the compound shown by the general formula (1) and/or (2) satisfies $1.00 \leq Mw/Mn \leq 1.10$, where Mw is a weight-average molecular weight and Mn is a number-average molecular weight measured by gel permeation chromatography in terms of polystyrene.

5. The composition for forming an organic film according to claim 4, wherein the material for forming an organic film contains one or more compounds selected from a compound shown by the following general formula (1) and/or (2) and one or more polymers selected from a polymer having a repeating unit shown by the following general formula (4) and/or (5), (I)

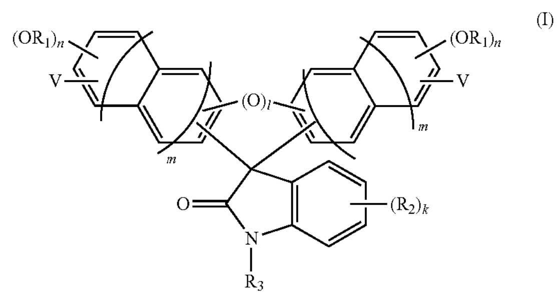

wherein $R_1$, $R_2$, $R_3$, "m", "n", "l", and "k" are as defined above, (II)

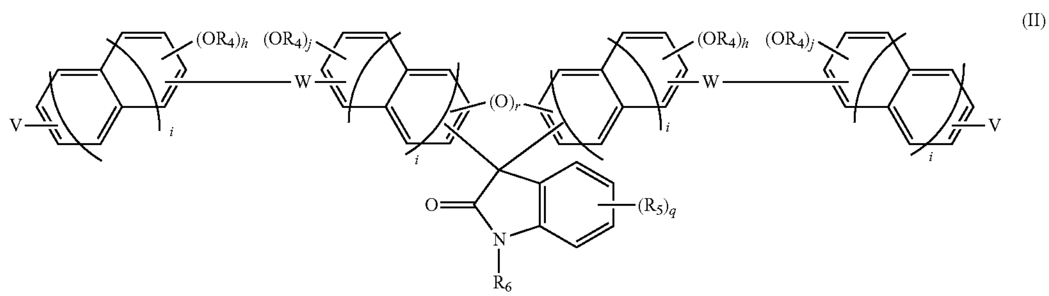

wherein $R_4$, $R_5$, $R_6$, "i", "q", "h", "j", "r", and W are as defined above, (4)

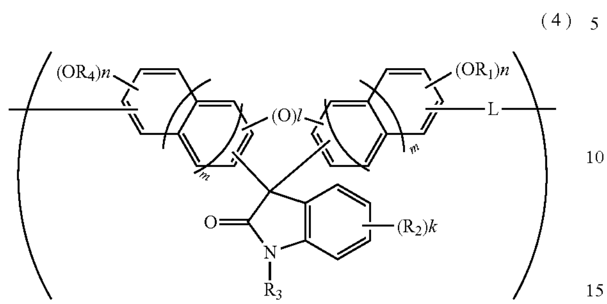

wherein $R_1$, $R_2$, $R_3$, "m", "n", "l", and "k" are as defined above, and L represents a divalent organic group having 1 to 40 carbon atoms, (5)

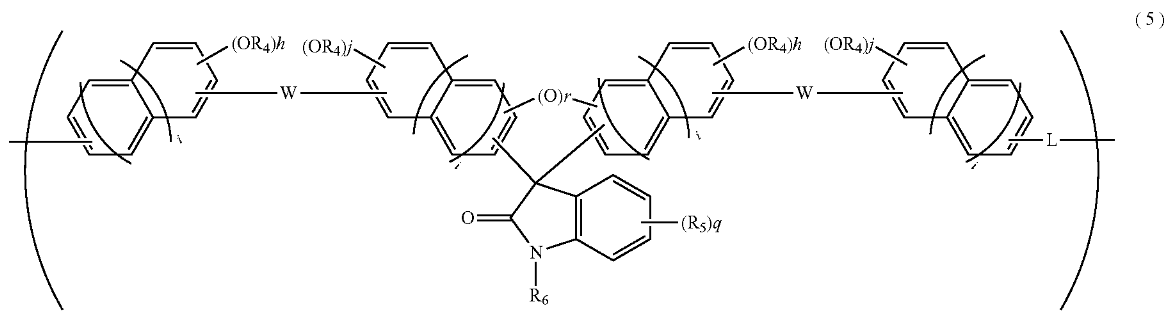

wherein $R_4$, $R_5$, $R_6$, W, L, "h", "i", "j", "q", and "r" are as defined above.

6. The composition for forming an organic film according to claim 4, wherein the organic solvent is a mixture of one or more kinds of organic solvent having a boiling point of lower than 180° C. and one or more kinds of organic solvent having a boiling point of 180° C. or higher.

7. The composition for forming an organic film according to claim 4, further comprising at least one of a surfactant and a plasticizer.

8. A patterning process comprising:

forming an organic film by using the composition for forming an organic film according to claim 4 on a body to be processed;

forming a silicon-containing resist middle layer film by using a silicon-containing resist middle layer film material on the organic film;

forming a resist upper layer film by using a photoresist composition on the silicon-containing resist middle layer film;

forming a circuit pattern in the resist upper layer film;

transferring the pattern to the silicon-containing resist middle layer film by etching while using the resist upper layer film having the formed pattern as a mask;

transferring the pattern to the organic film by etching while using the silicon-containing resist middle layer film having the transferred pattern as a mask; and further forming the pattern in the body to be processed by etching while using the organic film having the transferred pattern as a mask.

9. A patterning process comprising:

forming an organic film by using the composition for forming an organic film according to claim 4 on a body to be processed;

forming a silicon-containing resist middle layer film by using a silicon-containing resist middle layer film material on the organic film;

forming an organic antireflective coating on the silicon-containing resist middle layer film;

forming a resist upper layer film by using a photoresist composition on the organic antireflective coating, so that a 4-layered film structure is constructed;

forming a circuit pattern in the resist upper layer film;

transferring the pattern to the organic antireflective coating and the silicon-containing resist middle layer film by etching while using the resist upper layer film having the formed pattern as a mask;

transferring the pattern to the organic film by etching while using the silicon-containing resist middle layer film having the transferred pattern as a mask; and further forming the pattern in the body to be processed by etching the body to be processed while using the organic film having the transferred pattern as a mask.

10. A patterning process comprising:

forming an organic film by using the composition for forming an organic film according to claim 4 on a body to be processed;

forming an inorganic hard mask selected from a silicon oxide film, a silicon nitride film, and a silicon oxynitride film on the organic film;

forming a resist upper layer film by using a photoresist composition on the inorganic hard mask;

forming a circuit pattern in the resist upper layer film;

etching the inorganic hard mask while using the resist upper layer film having the formed pattern as a mask;

etching the organic film while using the inorganic hard mask having the formed pattern as a mask; and further forming the pattern in the body to be processed by etching the body to be processed while using the organic film having the formed pattern as a mask.

11. A patterning process comprising:

forming an organic film by using the composition for forming an organic film according to claim 4 on a body to be processed;

forming an inorganic hard mask selected from a silicon oxide film, a silicon nitride film, and a silicon oxynitride film on the organic film;

forming an organic antireflective coating on the inorganic hard mask;

forming a resist upper layer film by using a photoresist composition on the organic antireflective coating, so that a 4-layered film structure is constructed;

forming a circuit pattern in the resist upper layer film;

etching the organic antireflective coating and the inorganic hard mask while using the resist upper layer film having the formed pattern as a mask;

etching the organic film while using the inorganic hard mask having the formed pattern as a mask; and further forming the pattern in the body to be processed by etching the body to be processed while using the organic film having the formed pattern as a mask.

12. The patterning process according to claim 10, wherein the inorganic hard mask is formed by a CVD method or an ALD method.

13. The patterning process according to claim 8, wherein the pattern in the resist upper layer film is formed by a lithography using light with a wavelength of 10 nm or more to 300 nm or less, a direct drawing with electron beam, nanoimprinting, or a combination thereof.

14. The patterning process according to claim 8, wherein exposure and development are performed to form the circuit pattern in the resist upper layer film in the patterning process, and the development is alkali development or development with an organic solvent.

15. The patterning process according to claim 8, wherein as the body to be processed, a semiconductor device substrate, a metal film, a metal carbide film, a metal oxide film, a metal nitride film, a metal oxycarbide film, or a metal oxynitride film is used.

16. The patterning process according to claim 15, wherein the metal is silicon, titanium, tungsten, hafnium, zirconium, chromium, germanium, cobalt, copper, silver, gold, aluminum, indium, gallium, arsenic, palladium, iron, tantalum, iridium, manganese, molybdenum, ruthenium, or an alloy thereof.

17. A polymer having a repeating unit shown by the following general formula (4), (4)

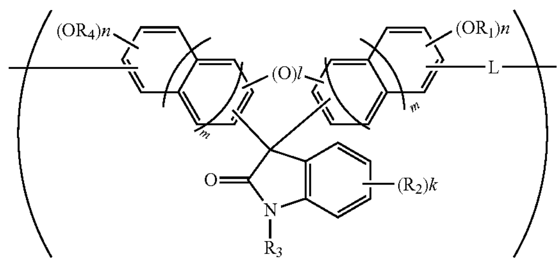

wherein $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, "k" represents an integer of 0 to 2, and L represents a divalent organic group having 1 to 40 carbon atoms.

18. The polymer according to claim 17, wherein the L is a divalent organic group shown by the following general formula (6), (6)

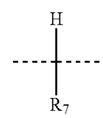

wherein $R_7$ represents a hydrogen atom or an aromatic ring-containing organic group having 1 to 20 carbon atoms, and a broken line represents an attachment point.

19. A compound shown by the following general formula (1), (1)

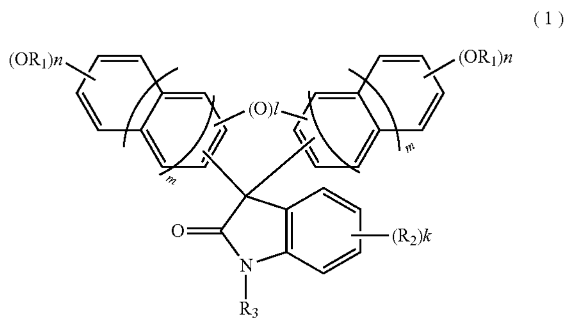

wherein $R_1$ represents a hydrogen atom, an allyl group, or a propargyl group, $R_2$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_3$ represents, an alkyl group having 1 to 4 carbon atoms, an alkynyl group having 2 to 4 carbon atoms, or an alkenyl group having 2 to 4 carbon atoms, "m" represents 0 or 1, "n" represents an integer of 1 or 2, "l" represents 0 or 1, aromatic rings forming a cyclic ether structure with one another when l=1, "k" represents an integer of 0 to 2.

20. A compound shown by the following general formula (2), (2)

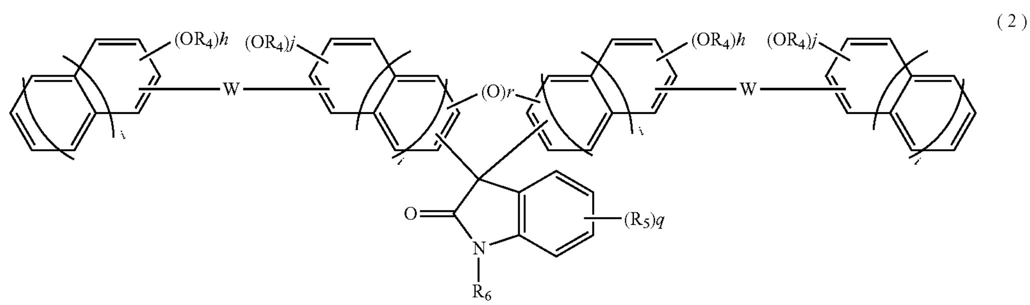

wherein $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship $1 \leq h+j \leq 4$, "r" represents 0 or 1, aromatic rings forming a cyclic ether structure with one another when r=1, and W represents any divalent group shown by the following formulae (3), (3)

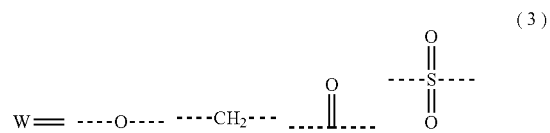

wherein a broken line represents an attachment point, and wherein the compound shown by the general formula (1) and/or (2) satisfies $1.00 \leq Mw/Mn \leq 1.10$, where Mw is a weight-average molecular weight and Mn is a number-average molecular weight measured by gel permeation chromatography in terms of polystyrene.

21. A polymer having a repeating unit shown by the following general formula (5), (5)

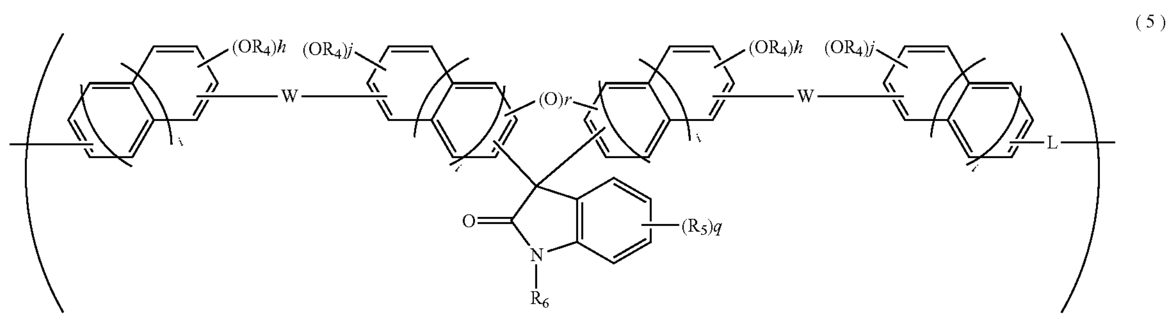

wherein $R_4$ represents a hydrogen atom, an allyl group, or a propargyl group, $R_5$ represents a nitro group, a halogen atom, a hydroxy group, an alkyloxy group having 1 to 4 carbon atoms, an alkynyloxy group having 2 to 4 carbon atoms, an alkenyloxy group having 2 to 4 carbon atoms, a linear, branched, or cyclic alkyl group having 1 to 6 carbon atoms, a trifluoromethyl group, or a trifluoromethyloxy group, $R_6$ represents an alkyl group having 1 to 4 carbon atoms, an alkynyl group having 2 to 4 carbon atoms, or an alkenyl group having 2 to 4 carbon atoms, "i" represents 0 or 1, "q" represents an integer of 0 to 2, "h" and "j" each independently represent an integer of 0 to 2 and satisfy the relationship 1≤h+j≤4, "r" represents 0 or 1, aromatic rings forming a cyclic ether structure with one another when r=1, W represents a single bond or any divalent group shown by the following formulae (3), and L represents a divalent organic group having 1 to 40 carbon atoms, (3)

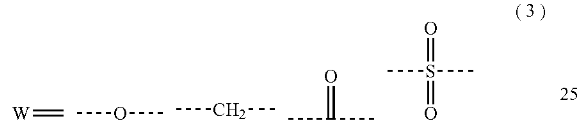

wherein a broken line represents an attachment point.

* * * * *